US005830755A

United States Patent [19]
Nishimura et al.

[11] Patent Number: 5,830,755
[45] Date of Patent: Nov. 3, 1998

[54] T-CELL RECEPTORS AND THEIR USE IN THERAPEUTIC AND DIAGNOSTIC METHODS

[75] Inventors: Michael Nishimura, Rockville; Steven A. Rosenberg, Potomac, both of Md.

[73] Assignee: The United States of America as represented by the Secretary of the Department of Health and Human Services, Washington, D.C.

[21] Appl. No.: 411,098

[22] Filed: Mar. 27, 1995

[51] Int. Cl.⁶ ........................................................ C12N 5/00
[52] U.S. Cl. ........................ 435/335; 536/23.1; 424/73.2; 530/387.7; 435/60; 435/7.23; 435/323; 435/320.1; 435/472.3; 435/69.1
[58] Field of Search .............................. 424/93.2; 435/6, 435/7.23, 325, 320.1, 172.3; 935/24, 55, 66, 62, 70, 71

[56] References Cited

U.S. PATENT DOCUMENTS

| | | | |
|---|---|---|---|
| 5,061,620 | 10/1991 | Tsukamoto et al. | 435/7.21 |
| 5,359,046 | 10/1994 | Capon et al. | 536/23.4 |
| 5,399,346 | 3/1995 | Anderson et al. | 424/93.21 |

FOREIGN PATENT DOCUMENTS

| | | |
|---|---|---|
| 203 403 | 4/1986 | European Pat. Off. . |
| 03/040793 | 5/1989 | European Pat. Off. . |
| WO 93/19163 | 9/1993 | WIPO . |
| WO 95/06409 | 3/1995 | WIPO . |

OTHER PUBLICATIONS

Dictionary of Microbiology and Molecular Biology, John Wiley & Sons Ltd., 1989, pp. 334–335 1989.

Rick Weiss, The Washington Post, Friday May 30, 1997; p. A01, 1997.

R. Wang, et al. "Limited T–Cell Antigen Receptor Repertoire in Tumore–Infiltrating Lymphocyte and Inhibition of Experimental Lung Metastasis of Murine Melanoma by Anti–TcR Antibody", *The Journal of Immunology*, vol. 154, No. 4, 1995, 1797–1803.

S. Rosenberg, "The Gene Therapy of Cancer", *Aids Research and Human Retroviruses*, vol. 10, No. Suppl. 3, 1994.

Kimura et al. (1986) J. Exp. Med. vol. 164: 739–750, Jul. 8, 1996.

Straten et al. (Jan. 1994) Int. J. Cancer:56, 78–86, Jul. 8, 1996.

Mitchel et al. (1993) Cancer Immunol Immunothol 37:15–25 Jul. 8, 1996.

Moritz et al. (1994) J. Clin. Invest. 93:1451–1457, Jul. 8, 1996.

Anderson et al. (1992) Nucleic Acid Research. vol. 20, No. 6, Jul. 8, 1996.

Boon (1993) Sci. Amer. p. 82, Mar. 1993, Jul. 8, 1996.

Yoshikai et al. (1986) J. Exp. Med. vol. 164 pp. 90–103, Jul. 8 1996.

Meo et al. (1993) J. of Immunology; vol. 151; 6110–6122, Jul. 8, 1996.

Toneguzzo et al. (1986) Proc. Nat. Acad. Sci USA 83:3496 Jul. 8, 1996.

Karlsson et al. (1986) EMBO J 5:2377 Jul. 8, 1996.

Coll et al. (1995) Gene Therapy, 2:592–593 Jul. 8, 1996.

Hynes et al. (1995) Nature Medicine; vol. 1 No. 7: 631–632, Jul. 8, 1996.

Shilyansky et al. (1994) "T–cell receptor usage by Melanoma–specific clonal and highly oligoclonal tumar–infiltrating lymphocyte lines", *Proc. Natl. Acad Sci USA*, vol. 91, pp. 2829–2833, Mar. 1994.

Treisman, et al. (1995) "Interleukin–2–transduced Lymphocytes Grow in an Autocrine Fashion and Remain Responsive to Antigen", *Blood*, vol. 35, No. 1, pp. 138–145, Jan. 1, 1995.

Herlyn, et al. (1984) "Efficient Selection of Human Tumor Growth–Inhibiting Monoclonal Antibodies", *Journal of Immunological Methods*, vol. 73, pp. 157–167, 1984.

Hwu, et al. (1995) "In vivo Antitumor Activity of T Cells Redirected with Chimeric Antibody/T–Cell Receptor Genes", *Cancer Research*, vol. 55, Aug. 1, 1995.

Lanier, et al. (1989) "Co–association of CD3 with a receptor (CD16) for IgG Fc on Human Natural killer Cells", *Nature*, vol. 342, pp. 803–804, Dec. 14, 1989.

Eshhar, et al. (1993) "Specific Activation and Targeting of cytotoix Lymphocytes Through chimeric Single Chains Consisting of Antibody–Binding Domains and the γ or subunits of the immunoglobulin and T–cell receptors", *Proc. Natl Acad. Sci. USA*, vol. 90, pp. 720–724, Jan. 1993.

Romeo, et al. (1991) "Cellular Immunity to HIV Activated by CD 4 Fused to T–Cell or Fc Receptor Polypeptides", *Cell*, vol. 64, pp. 1037–1046, Mar. 8, 1991.

Kuwana, et al., (1987) "Expression of Chimeric Receptor Composed of Immunoglobulin–Derived V Resions and T–Cell Receptor Derived C Regions", *Biochemical and Biophysical Research Communications*, pp. 960–968, vol. 149, No. 3 Dec. 1987.

Huston, et al. (1988) "Protein Engineering of Antibody Binding Sites: Recovery of Specific Activity in an Anti––Digoxtin Single Chain Fv Analogue Produced in Escherichia coli", *Proc. Natl. Acad Sci*, USA, pp. 5879–5883, Aug. 1988.

(List continued on next page.)

*Primary Examiner*—Christopher S. F. Low
*Assistant Examiner*—Dave T. Nguyen
*Attorney, Agent, or Firm*—Morgan & Finnegan, L.L.P.

[57] ABSTRACT

The present invention provides nucleic acid sequences for T-cell receptors which recognize tumor associated antigens. In particular, T-cell receptors which recognize melanoma antigens. This invention also provides T-cells expressing the antigen specific T-cell receptors. In addition, this invention provides stem cells expressing the antigen specific T-cell receptors or chimeric receptors. This invention further relates to therapeutic and diagnostic compositions and methods employing the T-cell receptors and chimeric receptors provided herein.

16 Claims, 12 Drawing Sheets

OTHER PUBLICATIONS

Gross, et al. (1989) "Generation of Effector T–Cells Expressing Chimeric T–Cell Receptor with Antibdy Type–Specificity", *Transplantation Proceedings*, Vo. 21, No. 1 (Feb.), 1989, pp. 127–130.

Becker, et al. "Expression of a Hybrid Immunoglobulin—T Cell Receptor Protein in Transgenic Mice", *Cell*, vol. 58, pp. 911–921, Sep. 8, 1989.

Goverman et al., "Chimeric Immunoglobulin T Cell Receptor Proteins Form Functional Receptors: Implications for T Cell Receptor Complex Formation and Activation", *Cell*, vol. 60, pp. 929–939, Mar. 23, 1990.

Gross et al. "Expression of Immunoglobulin T–Cell Receptor Chimeric Molecules as Functional Receptors with Antibody Type Specifity", *Proc. Natl. Acad Sci. USA*, Vo. 86, pp. 1024–10028, Dec. 1989.

DJ Cole et al. "T–Cell receptor usage and epitope mapping of HLA–A2 restricted, melanoma reactive CTL clones and oligoclonal lines", *The Faseb Journal*, Abstracts, Apr. 9–13, 1995.

Hwu, et al. (1994) "The Use of Gene–modified Tumor–Infiltrating Lymphocytes for Cancer Therapy", vol. 716, *Annals of the New York Academy of Sciences*, pp. 188–199, May 31, 1994.

Hwu, et al. (1994) "The Genetic Modification of T–Cells for Cancer therapy: An Overview of Laboratory and Clinical Trails", *Cancer Detection and Prevention*, vol. 18(1), pp. 43–50 (1994).

Hwu, et al. (1993) "Lysis of Ovarian Cancer Cells by Human Lymphocytes Redirected with a Chimeric Gene Compossed of an Antibody Variable Region and the Fc Receptor ξ Chain", *The Journal of Experimental Medicine*, vol. 178, pp. 361–366, Jul. 1993.

Hwu, et al. (1993) "Functional and Molecular Characterization of Tumor–Infiltrating Lymphocytes Transduced with Tumor Necrosis Factor α cDNA for the Gene Therapy of Cancer in Humans", *The Journal of Immunology*, Vo. 150, pp. 4104–4115, No. 9, May 1993.

Nishimura et al. (1994) "T–Cell Receptor Repertoire in Tumor–infiltrating Lymphocytes, Analysis of Melanoma–Specific Long–Term Lines", *Journal of Immunotherapy*, Vo. 16, pp. 85–94, (1994).

Cole et al. (1994) "Identification of MART–1–specific T–Cell Recepotrs: T Cells Utilizing Distrinct T–Cell Receptor Variable and Joing Regions Recognize the Same Tumar Epitope", *Cancer Research*, vo. 54, pp. 5265–5268, Oct. 15, 1994.

Cole et al. (1995) Characterization of the Functional Specificity of a Cloned T–Cell Receptor Heterodimer Recognizing the MART–1 Melanoma Antigen, *Cancer Research*, Vo. 55, pp. 748–752, Feb. 15, 1995.

FIG 1A

TIL C10-1
Vα8.2/Jα49/Cα

V gene
TACTTTTGTGCA
 Y  F  C  A

GAGAATATGATGAACACCGGTAACCGGTAACACCGGTTCTATTTTGGAACAGGAGACAAGTTTGACGGTCATTCCAA
 E  N  M  M  N  T  G  N  Q  F  Y  F  G  T  G  T  S  L  T  V  I  P  N

C region
ATATCCAGAACCCTGAC
 I  Q  N  P  D

TIL C10-1
Vα14.1/Jα32/Cα

ATGTATTTCTGTGCT
 M  Y  F  C  A

TATAGGGGCCTTGGGTGTCTACAAACAGCTCATCTTTGGAACTGGCACTCTGCTTGCTGTCCAGCAAGTAC
 Y  R  G  L  G  V  L  Q  S  S  L  F  L  G  ?  ?  ?  ?  ?  ?  ?

ATATCCAGAACCCTGAC
 I  Q  N  P  D

TIL C10-1
Vβ13.6/Dβ1.1/Jβ1.5/Cβ1

TACTTCTGTGCCAGC
 Y  F  C  A  S

CGACTACTATAAGGTCCCGTATAGCAATCAGCCCCAGCATTTGGTGATGGGACTCGACTCTCCATCCTAG
 R  P  T  T  I  ?  V  P  Y  S  N  Q  P  Q  H  F  G  D  G  T  R  L  S  I  L  E

AGGACCTGAACAAGGTG
 D  L  N  K  V

FIG 1B

TIL F2-2
Vα17/Jα42/Cα

V gene
ACCTACTTCTGTGCA
 T  Y  F  C  A

GCAAGCAAGGGAGGCAGCCAAGGAAATCTCATCTTTGGAAAATGGCACTAAACTCTGTTAAACCAA
 A  S  K  G  G  S  Q  G  N  L  I  F  G  K  G  T  K  L  S  V  K  P  N

C region
ATATCCAGAACCCTGAC
 I  Q  N  P  D

TIL 1200
Vα9/Jα16/Cα

ATGTATTACTGTGCT
 M  Y  Y  C  A

CTAATCCCAGGAGGCCAGAAGCTGCTCTTTGCTCGAGGTACCATGTTAAAGGTTGATCTCA
 L  I  P  G  G  Q  K  L  L  F  A  R  G  T  M  L  K  V  D  L  N

ATATCCAGAACCCTGAC
 I  Q  N  P  D

TIL 5
Vα1/Jα49/Cα

GAGTACTTCTGTGCT
 E  Y  F  C  A

GTGGGGGCCCACCGGTGCCTATGGGAACCAGTTCTATTTTGGGACACAGGAGACAAGTTTGACGGTCATTCCAA
 V  G  A  ?  G  N  Q  F  Y  F  G  T  G  T  S  L  T  V  I  P  N

ATATCCAGAACCCTGAC
 I  Q  N  P  D

TIL F2-2
Vβ6.5/Dβ1.1/Jβ1.5/Cβ1

ATGTACCTCTGTGCCAGC
 M  Y  L  C  A  S

TTAGTAGCTGGGACAGGGGTGGTATCAGCCCCCAGCATTTTGGTGATGGGACTCGACTCTCCAGCCTAG
 L  V  W  D  R  G  G  N  Q  P  Q  H  F  G  D  G  T  R  L  S  I  L  E

AGGACCTGAACAGGTG
 D  L  N  K  V

TIL 1200
Vβ22.1/Dβ2.1/Jβ2.1/Cβ2

ATGTACTTCTGTGCC
 M  Y  F  C  A

GCTGGGGAGACTAGCGGGGTGTCAATGAGCAGTTCTTCCGGGACCAGTTCTTCGGGCCAGGGACAAGGCTCCTGGTGCTAG
 A  G  E  T  S  G  V  S  N  E  Q  F  F  G  P  G  T  R  L  ?  V  L  E

AGGACCTGAAAAACGTG
 D  L  K  N  V

TIL 5
Vβ7.3/Dβ2.1/Jβ2.1/Cβ2

CTGTATCTCTGTGCCAGC
 ?  Y  L  C  A  S

CAAGATCTCCTGAGTTGGGATGAGCAGTTCTTCGGGCCAGGGACAGTCCTGCTAG
 Q  D  L  L  S  W  D  E  Q  F  F  G  P  G  T  R  L  T  V  L  E

AGGACCTGAAAAACGTG
 D  L  K  N  V

FIG. 2

|  | Vα region | Jα region | Cα region |
|---|---|---|---|
| TIL 1E2 Vα25/Jα54/Cα | ATCTACTTCTGTGCT I Y F C A | GGCCCGGGTAGCAACTATAAACTGACATTTGGAAAAGGAACTCTTAACCGTGAATCAA G P G S N Y K L T F G K G T L L T V N P N | ATATCCAGAACCCTGAC I Q N P D |
| TIL A42 Vα21/Jα42/Cα | GTGTACTTCTGTG V Y F C A | CCGCATATTATGGAGGAAGCCAAGGAAATCTCATCTTTGGAAAAGGCACTAAACTCTCTGTTAAACCAA A Y Y G G S Q G N L I F G K G T K L S V K P N | ATATCCAGAACCCTGAC I Q N P D |

|  | Vβ region | Jβ region | Cβ region |
|---|---|---|---|
| TIL 1E2 Vβ3.1/Dβ1.1/Jβ1.1/Cβ1 | ATGTACCTCTGTGCCAGCAGT M Y L C A S S | TTTGAAGGATTGGGCACTGAAGCTTTCTTTGGACAAGGCACCAGACTCACAGTTGTAG F E G L G T E A F F G Q G T R L T V V E | AGGACCTGAACAAGGTG D L N K V |
| TIL A42 Vβ7.3/Dβ2.1/Jβ2.7/Cβ2 | CTGTATCTCTGTGCCAGCAGC L Y L C A S S | CAAGAGGGACTAGCGGGAGCGTCGCAGTACTTCGGCCCAGGCACCAGGCTCACGGTCACAG Q E G L A G A S Q Y F G P G T R L T V T E | AGGACCTGAAAAACGTG D L K N V |

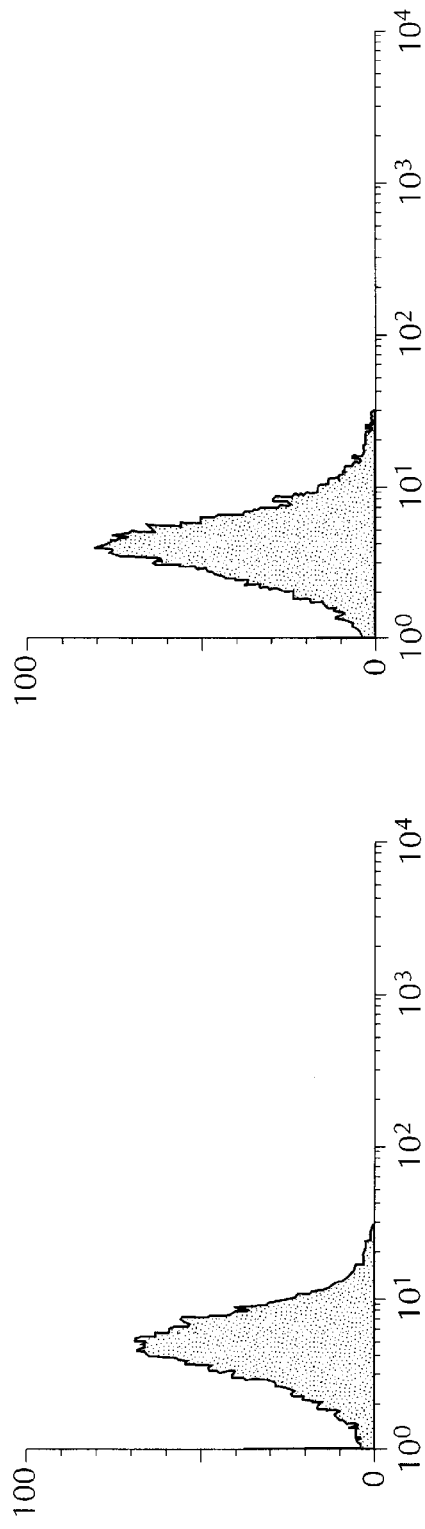
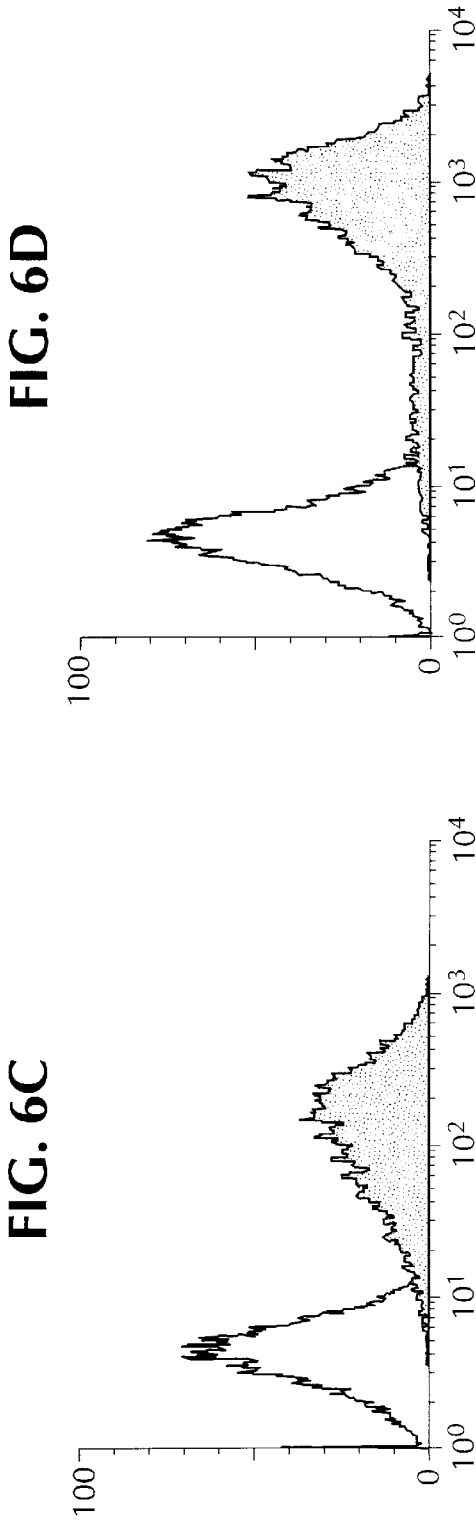

T-CELL RECEPTORS AND THEIR USE IN THERAPEUTIC AND DIAGNOSTIC METHODS

FIELD OF THE INVENTION

The field of the present invention relates generally to compositions and methods for the treatment or prevention of diseases in mammals. More specifically, this invention relates to T-cell receptors and chimeric receptors that recognize tumor associated antigens and to preventative, diagnostic and therapeutic applications which employ these T-cell receptors.

BACKGROUND OF THE INVENTION

Classic modalities for the treatment of diseases such as human cancers, autoimmune diseases, viral, bacterial, parasitic and fungal diseases include surgery, radiation chemotherapy, antibiotics or combination therapies. However, these therapies are not effective against a majority of these diseases. Alternate therapies for preventing or treating human diseases are greatly needed. In the past decade immunotherapy and gene therapy utilizing T-lymphocytes have emerged as new and promising methods for treating human disease, in particular human cancers.

T-cells play an important role in tumor regression in most murine tumor models. Tumor infiltrating lymphocytes (TIL) that recognize unique cancer antigens can be isolated from many murine tumors. The adoptive transfer of these TIL plus interleukin-2 can mediate the regression of established lung and liver metastases (Rosenberg, S. A., et al., (1986) *Science* 3233:1318–1321). In addition, the secretion of IFN-γ by injected TIL significantly correlates with in vivo regression of murine tumors suggesting activation of T-cells by the tumor antigens. (Barth, R. J., et al., (1991) *J. Exp. Med.* 173:647–658). The known ability of TIL to mediate the regression of metastatic cancer in 35 to 40% of melanoma patients when adoptively transferred into patients with metastatic melanoma attests to the clinical importance of the antigens recognized (Rosenberg, S. A., et al., (1988) *N Engl J Med* 319:1676–1680; Rosenberg S. A. (1992) *J. Clin. Oncol.* 10:180–199).

T-cell receptors on CD8$^+$ T-cells recognize a complex consisting of an antigenic peptide (9–10 amino acids for HLA-A2), β-2 microglobulin and class I major histocompatibility complex (MHC) heavy chain (HLA-A, B, C, in humans). Peptides generated by digestion of endogenously synthesized proteins are transported into the endoplastic reticulum, bound to class I MHC heavy chain and β2 microglobulin, and finally expressed in the cell surface in the groove of the class I MHC molecule.

Strong evidence that an immune response to cancer exists in humans is provided by the existence of tumor reactive lymphocytes within melanoma deposits. These lymphocytes, when isolated, are capable of recognizing specific tumor antigens on autologous and allogeneic melanomas in an MHC restricted fashion. (Itoh, K. et al. (1986), *Cancer Res.* 46:3011–3017; Muul, L. M., et al. (1987), *J. Immunol.* 138:989–995); Topalian, S. L., et al., (1989) *J. Immunol.* 142:3714–3725; Darrow, T. L., et al., (1989) *J. Immunol.* 142:3329–3335; Hom, S. S., et al., (1991) *J. Immunother.* 10:153–164; Kawakami, Y., et al., (1992) *J. Immunol.* 148:638–643; Hom, S. S., et al., (1993) *J. Immunother.* 13:18–30; O'Neil, B. H., et al., (1993) *J. Immunol.* 151:1410–1418). TIL from patients with metastatic melanoma recognize shared antigens including melanocyte-melanoma lineage specific tissue antigens in vitro (Kawakami, Y., et al., (1993) *J. Immunother.* 14:88–93; Anichini, A. et al., (1993) et al., *J. Exp. Med.* 177:989–998). Anti-melanoma T-cells appear to be enriched in TIL probably as a consequence of clonal expansion and accumulation at the tumor site in vivo (Sensi, M., et al., (1993) *J. Exp. Med.* 178:1231–1246). The transduction of T-cells with a variety of genes, such as cytokines, has been demonstrated. T-cells have been shown to express foreign gene products. (Blaese, R. M., *Pediatr. Res.*, 33 (1 Suppl):S49–S53 (1993); Hwu, P., et al. *J. Immunol,* 150:4104–415 (1993); Culver, L., et al. *Proc. Natl. Acad. Sci. USA,* 88:3155–3159 (1991)) The fact that patients mount cellular and humoral responses against tumor associated antigens suggests that identification and characterization of additional tumor antigens will be important for immunotherapy of patients with cancer.

SUMMARY OF THE INVENTION

This invention relates, in general, to nucleic acid and amino acid sequences for T-cell receptors which recognize or bind tumor associated antigens and to compositions and methods employing the same. In particular to the amino acid and nucleic acid sequences for the Variable-Joining (V/J) or Variable-Diversity-Joining (V/D/J) junctional sequences for the antigen specific T-cell receptors described herein. This invention further provides therapeutic uses for the nucleic acid and amino acid sequences for the T-cell receptors. It is also an object of this invention to provide T-cells or hematopoietic stem cells carrying these T-cell receptors or chimeric receptors and methods of using the same.

It is an object of this invention to provide isolated nucleic acid sequences encoding for T-cell receptors or parts thereof which recognize tumor associated antigens.

It is an object of this invention to provide amino acid sequences for T-cell receptors or parts thereof which recognize or bind tumor associated antigens.

It is another object of this invention to provide isolated nucleic acid sequences of T-cell receptors which recognize melanoma antigens.

It is another object of this invention to produce recombinant molecules encoding for all or parts thereof for the T-cell receptors that recognize tumor associated antigens.

It is another object of this invention to provide methods of detecting nucleic acid sequences encoding the antigen specific T-cell receptors.

It is another object of this invention to provide diagnostic methods for human disease, in particular for cancers.

It is yet another object of this invention to provide a chimeric receptor comprising an antibody variable region joined to the cytoplasmic region of CD28 from a T cell or a similar region which can provide a T cell with costimulation signals.

It is a further object of this invention to provide methods for prophylactic or therapeutic uses involving all or part of the nucleic acid sequence or amino acid sequences for the T-cell which recognize tumor associated antigens.

It is also an object of this invention to provide compositions and methods for immunotherapy employing hematopoietic stem cells or T-cells carrying the T-cell receptors or chimeric receptors.

In addition, it is another object of this invention to provide combination therapies comprising all or part of the nucleic acid sequences described herein and other T-cell receptors that recognize tumor associated antigens.

It is another object of this invention to provide a method of prophylactic or therapeutic treatment of cancers using the methods described herein.

It is a further object of this invention to provide T-cells or hematopoietic stem cells carrying receptors that recognize cancer antigens for use in immunotherapy.

DESCRIPTION OF THE FIGURES

FIGS. 1A and 1B show TCRα and TCRβ junctional sequences from melanoma specific cytotoxic T lymphocyte (CTL) clones. FIG. 1A shows that Clone C10-1 contains one functional TCRα transcript and one in frame TCRβ transcript. Although the Vα 14.1/Jα32/Cα transcript was in frame, the N (N diversity region) region sequence produced a frame shift in Jα32 resulting in the loss of the highly conserved FGXG structural motif (Koop, et al. (1993) *Genomics* 84:478–493). Splicing at an alternative site at the 3' end of the Jα32 segment resulted in the restoration of the reading frame in the C region. The TCRα gene using Vα8.2/Jα49/Cα and the TCRβ gene were productively rearranged. Boxes indicate the 3' ends of the V genes and the 5' ends of the C regions. The germline part of the J regions is underlined. The N regions are unmarked. Only the 5' end of the constant region is shown. FIG. 1B shows the alignment of the TCRα and TCRβ junctional sequences from three HLA-A2 restricted TIL. The amino acid sequence for each J region matches the sequence reported for other transcripts using the same J region. No DNA or amino acid sequence homology was observed in the N regions. Only the 5' end of the constant region is shown.

FIG. 2 shows TCR α and TCR β junctional sequences from MART-1 epitope M9-2 specific cytotoxic T-lymphocyte clones. The 3' ends of the V genes and the 5' ends of the C regions are labeled. Germline J regions are underlined, and the N regions are unmarked. The amino acid sequence for each J region matches the sequence reported for other transcripts using the same J region. Only the 5' end of the constant region is shown.

FIGS. 3A to 3L shows immunofluorescence analysis of clone 5 TCR-transfected (bulk, clone 13, and clone 22) and nontransfected (neo) Jurkat cell lines. Jurkat transfectants ($1\times10^6$) were incubated for 12 h at 37° C. with (represented by solid-line histograms) or without (represented by dotted-line histograms) 100 µl of Jurkat TCRβ chain-specific mAb C305.2 supernatant. All four cell lines were then restained with: FIG. 3A anti-CD3 mAb; FIG. 3B pan-specific anti-TCR-1 mAb; and FIG. 3C C305.2 mAb (to verify the down-modulation of endogenous TCR).

FIG. 6 shows FACS analysis with MoAb MOv18 to determine expression of folate binding protein (FBP) on various tumor lines. IGROV-1 is a human ovarian carcinoma. 24JK is a clone of the poorly-immunogenic methylcholanthrene induced murine sarcoma MCA-102. 24JK cells were retrovirally transduced with a vector containing the FBP gene to generate the 24JK-FBP cell line. 888 MEL is a human melanoma cell line. (Open graph=control antibody; Shaded graph=MOv18 antibody; y-axis=relative number of cells; x-axis log fluorescence intensity)

DETAILED DESCRIPTION OF THE INVENTION

Figure 3A:
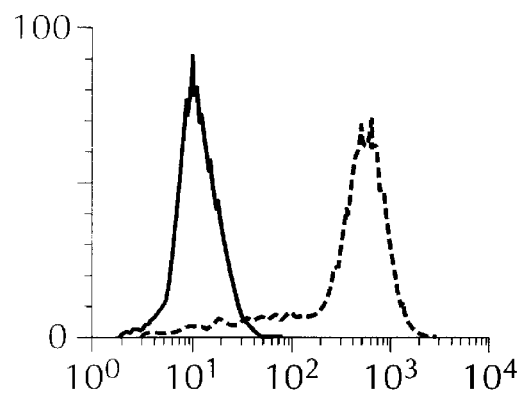

For the purpose of a more complete understanding of the invention, the following definitions are described herein. Nucleic acid sequences include, but are not limited to, DNA, RNA or cDNA. Substantially homologous as used herein refers to substantial correspondence between the nucleic acid sequence for the V-J or V-D-J junctional sequences for the α and β chains of the tumor antigen specific T-cell receptors provided herein and that of any other nucleic acid sequence. By way of example, substantially homologous means about 50–100% homology, preferably by about 70–100% homology, and most preferably about 90–100% homology between the nucleic acid sequences and that of any other nucleic acid sequence. In addition, substantially homologous as used herein also refers to substantial correspondences between the amino acid sequence of the V-J or V-D-J junctional sequences of the antigen specific T-cell receptors provided herein and that of any other amino acid sequence.

Major Histocompatibility Complex (MHC) is a generic designation meant to encompass the histocompatibility antigen systems described in different species including the human leucocyte antigens (HLA). The term cancer includes but is not limited to, melanoma, epithelial cell derived cancers, lung cancer, colon cancer, ovarian cancer, breast cancer, kidney cancer, prostate cancer, brain cancer, or sarcomas.

Such cancers in mammals may be caused by, chromosomal abnormalities, degenerative growth and developmental disorders, mitogenic agents, ultraviolet radiation (UV), viral infections, inappropriate tissue expression of a gene, alterations in expression of a gene, or carcinogenic agents. The term melanoma includes, but is not limited to, melanomas, metastatic melanomas, melanomas derived from either melanocytes or melanocyte related nevus cells, melanocarcinomas, melanoepitheliomas, melanosarcomas, melanoma in situ, superficial spreading melanoma, nodular melanoma, lentigo maligna melanoma, acral lentiginous melanoma, invasive melanoma or familial atypical mole and melanoma (FAM-M) syndrome. The aforementioned cancers can be treated, assessed or diagnosed by methods described in the present application.

T lymphocytes recognize antigen in the form of peptide fragments that are bound to class I and class II molecules of the major histocompatibility complex (MHC) locus. The T-cell receptor for antigen (TCR) is a complex of at least 8 polypeptide chains. ("Basic and Clinical Immunology" (1994) Stites, Terr and Parslow(eds) Appleton and Lange, Nenmack Conn.) Two of these chains (the α β chains) form a disulfide-linked dimer that recognizes antigenic peptides bound to MHC molecules and therefore is the actual ligand-binding structure within the TCR. The TCR α and β chains are similar in many respects to immunoglobulin proteins. The amino-terminal regions of the α and β chains are highly polymorphic, so that within the entire T-cell population there are a large number of different TCR α/β dimers, each capable of recognizing or binding a particular combination of antigenic peptide and MHC.

The α/β dimer is associated with a complex of proteins designated CD3. The CD3 molecules are involved in signal transduction by allowing the TCR to convert the recognition of antigen/MHC into intracellular signals for transduction.

To generate the diversity of TCR required to recognize a wide spectrum of antigenic determinants, the TCR α and β genes use a combinatorial strategy of DNA rearrangement similar to that of the immunoglobulin genes. The germline TCR β gene contains about 65 V (variable), 2 D (diversity), 13 J (joining) gene segments and 2 C (constant regions segments). When the TCR β gene rearranges early in T-cell development, one of the $V_\beta$ region segments becomes linked to one of the $D_\beta$ regions and to one of the $J_\beta$ segments to form a single transcriptional unit. The V-D-J splices to a constant $C_\beta$ (constant) region to form a TCR β mRNA that encodes a functional protein. Great diversity is generated by this combinatorial joining. In the TCR α locus, there are greater than 45–50 segments V segments and about 60 J segments, one C segment but no D segments. To form a functional TCR α chain gene, a $V_\alpha$ segment joins to a $J_\alpha$ segment and the V-J transcript splices to a constant region (Cα).

Diversity is further enhanced by imprecise joining of the gene segments and/or by the insertion of non-germline-encoded nucleotides (designated N regions) between segments during the rearrangement process. These mechanisms generate junctional diversity, in particular the diversity of sequences at the junctions between $V_\alpha$ and $J_\alpha$ and between $V_\beta$, $D_\beta$, and $J_\beta$ segments. The V-J and V-D-J junctional sequences are unique to each T-cell receptor clonotype and contribute to the T-cell receptor diversity In accordance with the present invention, amino acid sequences are provided for the V-J or V-D-J junctional regions or parts thereof for the alpha and beta chains of the T-cell receptor which recognize tumor associated antigens.

In general, this invention relates to T-cell receptors which recognize or bind tumor associated antigens presented in the context of MHC Class I. In a preferred embodiment the tumor associated antigens recognized by the T-cell receptors of this invention are melanoma antigens. By way of example the melanoma specific T-cell receptors of this invention may recognize melanoma antigens in the context of HLA-A2.1 or HLA-A1. Examples of melanoma antigens which are recognized by the T-cell receptors include, but are not limited to, MART-1, or peptides thereof or gp-100 or peptides thereof. In a preferred embodiment the T-cell receptor recognizes or binds to the MART-1 peptide, in particular epitopes M9-1 (TTAEEAAGI), M9-2 (AAGIGILTV), M10-3 (EAAGIGILTV), and M10-4 (AAGIGILTVI) (shown in single letter amino acid code, Examples 2 and 3) or gp-100 peptide epitopes.

The functional α chain of the heterodimeric T-cell receptors of this invention may have the following formula:

V-J-C wherein,

V is an amino acid sequence comprising the variable region of the α chain. By way of example, the V gene after rearrangement may have a 3' end encoding for a carboxy terminus sequence of Cysteine-$Xaa_n$ where n may be about 1–5 and Xaa may be any amino acid or a combination of amino acids. Preferably Xaa is Alanine or Serine. In a preferred embodiment, the 3' end of the V gene encodes for a carboxy terminus of Cysteine-Alanine. Preferred carboxy terminus for the V α gene are shown in FIGS. 1A and 1B and FIG. 2. Examples of Vα genes that be may be used in generating this region include, but are not limited to, Vα 8.2 or Vα17, Vα9, Vα1, Vα25, or Vα21.

J denotes the joining region. Examples of J genes that may be used to generate this region, include but are not limited to, Jα49, Jα42, Jα16, or Jα54. In addition the J region may also contain N regions as shown in FIGS. 1A–1B and 2. Preferred J regions for the α chains of the T-cell receptor of this invention are shown in FIG. 1A and 1B and FIG. 2. C denotes the constant region of the α chain.

Preferred V-J junctional sequences for the T-cell receptors of this invention are shown in FIGS. 1A–1B and FIG. 2.

The functional β chain of the heterodimer T-cell receptors may have the formula:

V-D-J-C wherein

V is an amino acid sequence comprising the variable region of the β chain. The V gene may have a 3' end encoding for a carboxy terminus of Cysteine-$Xaa_n$ wherein n may be about 1–5 and Xaa may be any amino acid or combination of amino acids. Preferably, Xaa is either Alanine or Serine. In a preferred embodiment, the 3' end of the V region encodes for a carboxy terminus of Cysteine-Alanine-Serine, or Cysteine-Alanine-Serine-Serine, or Cysteine-Alanine. Preferred carboxy termini for the Vβ region are shown in FIG. 1A–FIG. 1B and FIG. 2. Examples of V genes that may be used for the V region include but are not limited to Vβ13.6, Vβ6.5, Vβ22.1, Vβ7.3, or Vβ3.1.

J denotes the joining region. Examples of Jβ genes that may be used in generating the joining regions include, but are not limited to, Jβ1.5, Jβ2.1, Jβ1.1, or Jβ2.7. The joining region may also contain N regions as shown in FIGS. 1A–1B and FIG. 2. Examples of D (diversity) genes that may be used include, but are not limited to Dβ1.1, or Dβ2.1.

C denotes the constant regions of the β chain. Examples of constant regions that may be used, include, but are not limited to Cβ1 in Cβ2. Preferred V-D-J junctional sequences for the β chain of the T-cell receptors provided herein are shown in FIGS. 1A–1B and FIG. 2.

In one embodiment the T-cell receptor of this invention comprises an α chain comprising a nucleic acid sequence encoding for a variable region having a 3' encoding for a carboxy terminus of Cysteine-Xaa$_n$, a J region and a constant region in combination with a β chain comprising a nucleic acid sequence encoding for a variable region having a 3' end encoding for carboxy terminus of Cysteine Xaa$_n$, a D region and a J region and a constant region. The alpha and beta chains of the T-cell receptors form a ligand binding domain that preferably recognizes a tumor associated antigen, most preferably melanoma antigens.

In the preferred embodiments the melanoma specific T-cell receptors provided herein have the following α and β chain combinations, the tumor infiltrating lymphocyte C10-1 T-cell clonotype comprising the Vα 8.2/Jα 49/Cα chain, (SEQ ID NOS:1 and 14) having the V-J junctional sequences shown in FIG. 1A and Vβ13.6/Dβ1.1/Jβ1.5/Cβ1 (SEQ ID NOS:3 and 16) having the V-D-J junctional sequences shown in FIG. 1A; the TIL F2-2 clonotype comprising Vα 17/Jα42/Cα (SEQ ID NOS:4 and 17) having the V-J junctional sequences shown in FIG. 1B and Vβ6.5/Dβ1.1/Jβ1.5/Cβ1 (SEQ ID NOS: 7 and 20) having the V-D-J junctional sequences shown in FIG. 1B; the TIL 1200 clonotype comprising Vα9/Jα16/Cα (SEQ ID NOS: 5 and 18) having the V-J junctional sequences shown in FIG. 1B and Vβ22.1/Dβ2.1/Jβ2.1/Cβ2 (SEQ ID NOS: 8 and 21) having the V-D-J junctional sequences shown in FIG. 1B; TIL5 clonotype comprising Vα1/Jα49/Cα (SEQ ID NOS: 6 and 19) having the V-J junctional sequences shown in FIG. 1B; and Vβ7.3/Dβ2.1/Jβ2.1/Cβ2 (SEQ ID NOS:9 and 22) having the V-D-J junctional sequences shown in FIG. 1B; the TIL 1E2 clonotype comprising Vα25/Jα54/Cα (SEQ ID NOS:18 and 23) having the V-J junctional sequences shown in FIG. 2 and Vβ3.1/Dβ1.1/Jβ1.1/Cβ1 (SEQ ID NOS: 12 and 25) having the V-D-J junctional sequences shown in FIG. 2; or the TIL A42 clonotype comprising Vα21/Jα42/Cα having the V-J junctional sequences shown in FIG. 2 and Vβ7.3/Dβ2.1/Jβ2.7/Cβ2 (SEQ ID NOS: 13 and 26) having the V-D-J junctional sequences shown in FIG. 2.

The T-cell receptors of this invention may be naturally occurring or synthetically produced. The α and β chains that comprise the T-cell receptors of this invention may be produced by standard recombinant methodology known to those skilled in the art. The GENBANK Accession Numbers for examples of the Vα, Jα, Cα, Vβ, Dβ and J β genes that may be used in constructing the α and β chains of the T-cell receptors of this invention are provided below. These genes may be used as the framework for inserting the unique J-V or J-D-V junctional sequences provided herein for the T-cell receptors of this invention.

Sequences of Vα Genes
Used by Cytotoxic Lymphocyte Clones

| TIL Clone | Gene | Genbank Name | Accession Number | Clone Name |
|---|---|---|---|---|
| TIL5 | Vα1 | HUMTCRAVG | L06885 | |
| | Vα1 | HSTCRA031 | X58769 | IGRa08 |
| | Vα1 | HUMTCAZC | M17668, J02992 | AE11 |
| TIL 1200 | Vα9 | HSTCRA08 | X04942 | HAVP36 |

-continued

Sequences of Vα Genes
Used by Cytotoxic Lymphocyte Clones

| TIL Clone | Gene | Genbank Name | Accession Number | Clone Name |
|---|---|---|---|---|
| | | HUMTCAXU | M13737 | HAP36 |
| | | HUMTCRAAD | M90479 | CTL5A2 |
| TIL C10-1 | Vα8.2 | HUMTCAXT | M13736 | HAP50 |
| TIL F2-2 | Vα17 | HUMTCVJCA | M97704 | IGRa05 |
| | | HSTCRVAE | X70309 | HTA61 |
| TIL A42 | Vα21 | HUMTCAYE | M15565 | L17 |
| TIL 1E2 | Vα25 | HSTRA003 | X58738 | IGRa03 |

Sequences of Jα, Cα, Vβ, Dβ, Jβ and Cβ Genes Used By CTL Clones

| Gene | Genbank Name | Accession Number |
|---|---|---|
| Jα1 through Jα60 | HUMTCRADCV | M94081 |
| Cα | HUMTCRAC | X02883 |
| Vβ1.1 through Vβ25.1 | HUMTCRB | L36092 |
| Dβ1, Jβ1.1 through Jβ1.6 | HUMTCBJC | M14158 |
| Dβ2, Jβ2.1 through β2.7 | HUMTCBJD | M14159 |
| Cβ1 | HUMTCBCB | M14157 |
| Cβ2 | HUMTCBCC | M12510 |

This invention further includes the T-cell receptors or analogs thereof having substantially the same function or activity as the T-cell receptors of this invention which recognize or bind tumor associated antigens, in particular melanoma antigens. Such receptors or proteins include, but are not limited to, a fragment of the protein, or a substitution, addition or deletion mutant of the T-cell receptors provided herein. This invention also encompasses proteins or peptides that are substantially homologous to the T-cell receptors provided herein or retain the same activity. The term "analog" includes any protein or polypeptide having an amino acid residue sequence substantially identical to the T-cell receptors provided herein in which one or more residues have been conservatively substituted with a functionally similar residue and which displays the functional aspects of the T-cell receptor as described herein. By way of example, such receptors may recognize the tumor associated antigens, MART-1 or gp100 or peptides derived therefrom. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid or another.

The phrase "conservative substitution" also includes the use of a chemically derivatized residue in place of a non-derivatized residue. "Chemical derivative" refers to a subject polypeptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those proteins or peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Proteins or polypeptides of the present invention also include any polypeptide having one or more additions and/or deletions or residues relative to the sequence of a polypeptide whose sequence is encoded by the DNA sequences of the receptor, so long as the requisite activity is maintained. The nucleic acid sequences for the tumor antigen specific T-cell receptors provided herein represent a preferred embodiment of the invention. It is however, understood by one skilled in the art that due to the degeneracy of the genetic code variations in the nucleic acid sequences may still result in a sequence capable of encoding the tumor antigen specific T-cell receptor. Such sequences are therefore functionally equivalent to the sequences set forth here. Nucleic acid sequences which encode for a tumor antigen T-cell receptor having the functional activity of that receptor are also intended to be encompassed by this invention.

This invention also provides a recombinant DNA molecule comprising all or part of the T-cell receptor nucleic acid sequences provided herein and a vector. The nucleic acid sequences encoding the $\alpha$ and $\beta$ chains of a T-cell receptor of the present invention may be placed in a single expression vector. Alternatively the $\alpha$ chain and the $\beta$ chain may each be placed in a separate expression vector. Expression vectors suitable for use in the present invention may comprise at least one expression control element operationally linked to the nucleic acid sequence. The expression control elements are inserted in the vector to control and regulate the expression of the nucleic acid sequence. Examples of expression control elements include, but are not limited to, lac system, operator and promoter regions of phage lambda, yeast promoters and promoters derived from polyoma, adenovirus, retrovirus, cytomeglia virus (CMV), SR$\alpha$, MMLV, SV40 or housekeeping promoters such as phosphoylycerol kinase (PGK) and $\beta$ actin. Additional preferred or required operational elements include, but are not limited to, leader sequence, termination codons, polyadenylation signals and any other sequences necessary or preferred for the appropriate transcription and subsequent translation of the nucleic acid sequence in the host system. It will be understood by one skilled in the art the correct combination of required or preferred expression control elements will depend on the host system chosen. It will further be understood that the expression vector may contain additional elements necessary for the transfer and subsequent replication of the expression vector containing the nucleic acid sequence in the host system. Examples of such elements include, but are not limited to, origins of replication and selectable markers and long terminal repeats (LTR) and internal ribosomal entry site (IRES). The expression vector may also include a leader peptide sequence. It will further be understood by one skilled in the art that such vectors are easily constructed using conventional methods (Ausubel et al., (1987) in "Current Protocols in Molecular Biology", John Wiley and Sons, New York, N.Y.) or commercially available.

Another aspect of this invention relates to a host organism into which recombinant expression vector containing all or part of the nucleic acid sequences of the T-cell receptor of this invention has been introduced. The $\alpha$ and $\beta$ chains of the T-cells of this invention may be expressed independently in different hosts or in the same host. Preferably the $\alpha$ and $\beta$ chains are introduced into the same host to allow for formation of a functional T-cell receptor. The host cells transformed with all or part of the T-cell receptor nucleic acid sequences of this invention include eukaryotes, such as animal, plant, insect and yeast cells and prokaryotes, such as *E. coli*. By way of example animal cells may include JURKAT-cells, T-lymphocytes, peripheral blood cells, monocytes, stem cells, natural killer cells or macrophages. The means by which the vector carrying the gene may be introduced into the cell include, but are not limited to, microinjection, electroporation, transduction, retroviral transduction or transfection using DEAE-dextran, lipofection, calcium phosphate, particle bombardment mediated gene transfer or direct injection of nucleic acid sequences encoding the T-cell receptors of this invention or other procedures known to one skilled in the art (Sambrook et al. (1989) in "Molecular Cloning. A Laboratory Manual", Cold Spring Harbor Press, Plainview, N.Y.). The T-cell receptor produced by the expression vector may be isolated and purified and used in crystallography studies or for the generation of antibodies.

In a preferred embodiment, eukaryotic expression vectors that function in eukaryotic cells are used. Examples of such vectors include, but are not limited to, retroviral vectors, vaccinia virus vectors, adenovirus vectors, adeno associated virus (AAV) herpes virus vector, fowl pox virus vector, plasmids, such as pCDNA3 (Invitrogen, San Diego, Calif.) or the baculovirus transfer vectors. By way of example, eukaryotic expression vectors that may be used include, but is not limited to, G1EN(Treisman, J., et al., *Blood*, 85:139; Morgan, et al. (1992) *Nucleic Acids, Res.* 20:1293–1299), LXSN (Miller, A. D., et al. *Methods Enzymol.*, 217:581–599 (1993); Miller, A. D., et al., *BioTechniques*, 7:980–988 (1989); Miller, A. D., et al. *Mol. Cell. Biol.*, 6:2895–2902 (1986); Miller, A. D., Curr. Top. Microbiol. Immunol., 158:1–24 (1992)) or SAM-EN vectors (Treisman, J., et al. *Blood,* 85:139). Preferred eukaryotic cell lines include, but are not limited to, COS cells, CHO cells, HeLa cells, NIH/3T3 cells, 293 cells (ATCC# CRL1573), T2 cells, dendritic cells, monocytes, or JURKAT-cells. In a preferred embodiment the recombinant T-cell receptor protein expression vector is introduced into mammalian cells, such as NIH/3T3, COS-7, CHO, 293 cells (ATCC #CRL 1573), T2 cells, dendritic cells, T-cells, natural killer cells, hematopoietic stem cells or monocytes to ensure proper processing and modification of the receptor protein. In one embodiment the expressed recombinant T-cell receptors may be detected by methods known in the art which include Coomassie blue staining and Western blotting using antibodies specific for the specific T-cell receptor. In a further embodiment, the recombinant protein expressed by the host cells can be obtained as a crude lysate or can be purified by standard protein purification procedures known in the art which may include differential precipitation, molecular sieve chromatography, ion-exchange chromatography, isoelectric focusing, gel electrophoresis, affinity, and immunoaffinity chromatography and the like. (Ausubel et. al., (1987) in "Current Protocols in Molecular Biology" John Wiley and Sons, New York, N.Y.). In the case of immunoaffinity chromatography, the recombinant protein may be purified by passage through a column containing a resin which has bound thereto antibodies specific for the T-cell receptors of this invention (Ausubel et. al., (1987) in "Current Protocols in Molecular Biology" John Wiley and Sons, New York, N.Y.).

The nucleic acid sequence or portions thereof, of this invention are useful as probes for the detection of expression of the rearranged genes encoding for the T-cell receptors of this invention as well as the corresponding mRNA. Therefore, another aspect of the present invention relates to an assay for detecting messenger RNA or DNA encoding the T-cell receptors of this invention in a biological sample.

RNA can be isolated as whole cell RNA or as poly(A)$^+$ RNA. Whole cell RNA and polyA RNA can be isolated by a variety of methods known to those skilled in the art. (Ausubel et al., (1987) on "Current Protocols in Molecular Biology", John Wiley and Sons, New York). Standard methods for isolating DNA from a biological sample, detecting alterations in a gene and detecting complex between the nucleic acid probe and genomic DNA sequences are provided in manuals such as Sambrook et al., (eds) (1989) "Molecular Cloning, A Laboratory Manual", Cold Spring Harbor Press, Plainview, N.Y. and in Ausubel et al., (eds) (1987) in "Current Protocols in Molecular Biology" John Wiley and Sons, New York, N.Y. Conventional Methodology may be used to resolve and detect the mRNA or DNA (Sambrook et. al., (1989) in "Molecular Cloning, A Laboratory Manual", Cold Spring Harbor Press, Plainview, N.Y.; Ausubel et al., (1987) in "Current Protocols in Molecular Biology, John Wiley and Sons, New York, N.Y.). Standard techniques may be used to label the probes of this invention. Sambrook et al., (eds) (1989) "Molecular Cloning, A Laboratory Manual", Cold Spring Harbor Press, Plainview, N.Y. and in Ausubel et al., (eds) (1987) in "Current Protocols in Molecular Biology" John Wiley and Sons, New York, N.Y. Radioactive and non-radioactive labelling kits are also commercially available.

Examples of biological samples that can be used in this bioassay include, but are not limited to, tissues such as lymph node, peripheral blood lymphocytes, tumor biopsies, bone marrow, lymphoid organs, biopsy specimens, such as melanoma, pathology specimens, and necropsy specimens. In a preferred embodiment, the nucleic sequence used as probes are derived from the J-V or J-D-V junctional sequences of the region of the α or β chain comprising the T-cell receptors (FIGS. 1A–1B and FIG. 2). Preferred nucleic acid sequences to be used as probes comprise or include the N region. Alternatively the full length or parts thereof of nucleic acid sequences provided herein may be used as probes.

In another embodiment, combinations of oligonucleotide pairs based on the J-V or J-D-V junctional sequences of the α or β chains respectively shown in FIGS. 1A–1B and 2 may be used to derive Polymerase Chain Reaction (PCR) primers to detect the RNA or rearranged germ line sequences in a biological sample. These primers can be used in a method following the reverse transcriptase—Polymerase Chain Reaction (RT-PCR) process for amplifying selected RNA nucleic acid sequences as detailed in Ausubel et al., (eds) (1987) In "Current Protocols in Molecular Biology" Chapter 15, John Wiley and Sons, New York, N.Y. The oligonucleotides can be synthesized by automated instruments sold by a variety of manufacturers or can be commercially prepared based upon the nucleic acid sequence of this invention. One skilled in the art will know how to select PCR primers based on the nucleic acid sequence for amplifying RNA or rearranged germline sequences DNA in a sample. Methods for the detection of the RNA or DNA encoding the T-cell receptors provided herein may be used to assess the efficacy of or determine the course of treatment for the therapeutic methods provided herein using the T-cells receptors.

In yet another embodiment of this invention all or parts thereof of the nucleic acid sequence for the antigen specific T-cell receptors provided herein can be used to generate transgenic animals. Preferably the sequences encoding α and β the chains of the antigen specific T-cells of this invention are introduced into an animal or an ancestor of the animal at an embryonic stage, preferably at the one cell stage and generally not later than about the eight cell stage. There are several means by which transgenic animals carrying a T-cell receptor gene can be made. One method involves the use of retroviruses carrying all or part of the T-cell receptor sequences. The retroviruses containing the transgene are introduced into the embryonic animal by transfection. Another method involves directly injecting the transgene into the embryo. Yet another method employs the embryonic stem cell method or homologous recombination method known to workers in the field. Examples of animals into which the T-cell receptor transgene can be introduced include, but are not limited to, non-human primates, mice, rats or other rodents. Such transgenic animals may be useful as biological models for the study of cancer and to evaluate diagnostic or therapeutic methods for the treatment of cancers in particular melanoma.

This invention further comprises an antibody or antibodies reactive with the T-cell receptor or parts thereof of this invention. In this embodiment of the invention the antibodies are monoclonal or polyclonal in origin. The antigen specific T-cell receptors or parts thereof used to generate the antibodies may be from natural or recombinant sources or generated by chemical synthesis. The natural T-cell receptors can be isolated from mammalian biological samples. Biological samples include, but is not limited to mammalian tissues such as peripheral blood lymphocytes (PBL), blood, lymphoid organs, lymph nodes, lymph nodes, T-cells, or biopsy samples, such as from melanoma. The natural proteins may be isolated by the same methods described above for recombinant proteins. Recombinant T-cell receptor proteins or peptides may be produced and purified by conventional methods. Synthetic peptides may be custom ordered, or commercially made or synthesized by methods known to one skilled in the art (Merrifield, R. B. (1963) *J. Amer. Soc.* 85:2149) based on the amino acid sequence of the invention. If the peptide is too short to be antigenic it may be conjugated to a carrier molecule to enhance the antigenicity of the peptide. Examples of carrier molecules, include, but are not limited to, human albumin, bovine albumin and keyhole limpet hemo-cyanin ("Basic and Clinical Immunology" (1991) Stites, D. P. and Terr A. I. (eds) Appleton and Lange, Norwalk, Conn., San Mateo, Calif.).

Exemplary antibody molecules for use in the detection methods of the present invention are intact immunoglobulin molecules, substantially intact immunoglobulin molecules or those portions of an immunoglobulin molecule that contain the antigen binding site, including those portions of immunoglobulin molecules known in the art as F(ab), F(ab'); F(ab)$_2$ and F(v). Polyclonal or monoclonal antibodies may be produced by methods known in the art. (Kohler and Milstein (1975) *Nature* 256, 495–497; Campbell "Monoclonal Antibody Technology, the Production and Characterization of Rodent and Human Hybridomas" in Burdon et al. (eds.) (1985) "Laboratory Techniques in Biochemistry and Molecular Biology," Volume 13, Elsevier Science Publishers, Amsterdam). The antibodies or antigen binding fragments may also be produced by genetic engineering. The technology for expression of both heavy and light chain genes in *E. coli* is the subject of the following PCT patent applications: publication number WO 901443, WO 901443 and WO 9014424 and in Huse et al. (1989) *Science* 246:1275–1281.

The antibodies of this invention may react with native or denatured T-cell receptor protein or peptides or analogs thereof. The specific immunoassay in which the antibodies are to be used will dictate which antibodies are desirable. Antibodies may be raised against the native T-cell receptor proteins or portions thereof or against synthetic peptides homologous to the unique regions of the amino acid sequence of the T-cell receptors.

In one embodiment the antibodies of this invention are used in immunoassays to detect the antigen specific T-cell receptor proteins in biological samples. In this method the antibodies of the present invention are contacted with a biological sample and the formation of a complex between the T-cell receptors and antibody is detected. Immunoassays of the present invention may be radioimmunoassay, Western blot assay, immunofluorescent assay, enzyme immunoassay, chemiluminescent assay, immunohistochemical assay and the like. (In "Principles and Practice of Immunoassay" (1991) Christopher P. Price and David J. Neoman (eds), Stockton Press, New York, N.Y.; Ausubel et al. (eds) (1987) in "Current Protocols in Molecular Biology" John Wiley and Sons, New York, N.Y.). Standard techniques known in the art for ELISA are described in *Methods in Immunodiagnosis,* 2nd Edition, Rose and Bigazzi, eds., John Wiley and Sons, New York 1980 and Campbell et al., *Methods of Immunology*, W. A. Benjamin, Inc., 1964, both of which are incorporated herein by reference. Such assays may be direct, indirect, competitive, or noncompetitive immunoassays as described in the art (In "Principles and Practice of Immunoassay" (1991) Christopher P. Price and David J. Neoman (eds), Stockton Pres, NY, N.Y.; Oellirich, M. 1984. *J. Clin. Chem. Clin. Biochem.* 22:895–904) Biological samples appropriate for such detection assays include mammalian tissues, melanoma and lymph nodes, pathology specimens, necropsy specimens, bone marrow, peripheral blood lymphocytes and biopsy specimens. Proteins may be isolated from biological samples by conventional methods described in (Ausubel et al., (eds) (1987) in "Current Protocols in Molecular Biology" John Wiley and Sons, New York, N.Y.).

The antibodies of this invention can be used in immunoassays to detect the specific T-cell receptors of this invention or alteration in the level of expression of T-cells carrying the melanoma specific T-cell receptors in biological samples. Examples of biological samples include, but are not limited to, mammalian tissues, such as biopsy tissue samples, such as melanoma, peripheral blood lymphocytes, bone marrow, tumor biopsies lymph nodes, lymphoid organs and tissue samples. Examples of diseases that can be assessed by these immunoassays, include, but are not limited to, melanomas and tissues which are secondary sites for melanoma metastasis. The antibodies of this invention can therefore be used in an immunoassay to diagnose, assess or prognoses a mammal afflicted with the disease.

In another embodiment, antibodies of this invention may be used to purify or enrich for T-cells carrying the receptors provided herein which recognize tumor associated antigens, in particular melanoma antigens. Immunoaffinity chromatography can be performed by conventional methods known to one skilled in the art (Ausubel et al. (eds) (1987) in "Current Protocols in Molecular Biology" John Wiley and Sons, New York, N.Y.). Such T-cells can then be administered in a therapeutically effective amount to mammals, preferably humans either prophylactically or therapeutically. Alternatively, such methods can be used to assess the efficacy or determine the treatment regime of the mammal.

In another embodiment monoclonal antibodies or polyclonal antisera generated in animals against all or parts thereof, preferably the unique region of the T-cell receptor can be used in immunoassays. In a preferred embodiment, a peptide based on the unique regions of the antigen specific α or β chains peptide may be conjugated to a carrier as described in (M. Bodanszky (1984) "Principles of Peptide Synthesis," Springer Verlag, New York, N.Y.). Using conventional methods, rabbits may be immunized with the protein or peptide conjugated to carriers. The animal receives similar booster doses and antisera titer is assessed by ELISA assay. Satisfactory levels of antisera are obtained when the anti-peptide antibody titer reaches a plateau. This antibody can be used in the standard immunoassays described above.

Alternatively anti-idiotype antibodies against T-cell receptors may be used to access the level of a specific T-cell carrying the receptors of this invention in a mammal being treated with the methods described herein.

The present invention provides a method of inhibiting or preventing the growth of tumor cells by exposing tumor cells to cells expressing the antigen specific T-cell receptors or chimeric receptors provided herein. The T-cell receptors of this invention which recognize or bind tumor associated antigens may also be used for either prophylactic or therapeutic purposes. When provided prophylactically, the T-cell receptor or cells into which the T-cell receptor has been introduced is provided in advance of any evidence or symptom in the mammal due to cancer, in particular melanoma. The prophylactic use of the T-cell receptors or cells into which the antigen specific T-cell receptors have been introduced, serves to prevent or attenuate cancer, in particular melanoma, in a mammal. When provided therapeutically, the T-cell receptor or cells expressing the receptors of this invention are provided at (or shortly after) the onset of the disease in the mammal. The therapeutic administration of the T-cell receptor or cells expressing those receptors serves to attenuate the disease.

Cell-based immunotherapy currently utilizes the adoptive transfer to patients of tumor specific TIL which are expanded ex vivo [Rosenberg S. A. 1992. *J. Clin. Oncol.,* 10:80; Rosenberg S. A., et al. *N. Engl. J. Med.,* 319:1676; Hwu P., et al. 1993. *J. Exp. Med.,* 178:361]. T-cell specificity may be redirected by the in vitro transfer of the nucleic acid sequences encoding the tumor associated antigen specific T-cell receptors of this invention. By way of example, a heterogenous population of T-cells, such as TIL, may be made more effective by conferring anti-tumor reactivity to non-specific T-cell populations within the TIL, or clonal expansion of undifferentiated T lymphocytes.

Cells that can be genetically modified to express the antigen specific T-cell receptors provided include, but is not limited to, lymphocytes, cytotoxic T-lymphocytes, hematopoietic stem cells, monocytes, stem cells, peripheral blood and natural killer cells. In a preferred embodiment of this invention T-cells can be genetically modified to express the tumor antigen specific T-cell receptors provided herein. Preferred antigen specific T-cell receptors are shown in FIGS. 1A–1B and FIG. 2. Constructs containing all or parts of the nucleic acid sequences encoding the T-cell receptors of this invention may be introduced in T-lymphocytes by conventional methodology. By way of example such methods include, but are not limited to, calcium phosphate transfection, electroporations, lipofections, transduction by retroviruses, injection of DNA, particle bombardment and mediated gene transfer use of a retroviral vector, viral vectors, transduction by viral coculturing with a producer cell line. Preferably the construct or constructs carrying the nucleic acid sequences of the present invention are introduced into the T-cells by transduction with viral supernatant or cocultivation with a retroviral producer cell line. Examples of vectors that may be used include, but are not limited to, defective retroviral vectors, adenoviral vectors, vaccinia viral vectors, fowl pox viral vectors, or other viral vectors (Mulligan, R. C., (1993) *Science* 260:926–932). Eukaryotic expression vectors G1EN (Treisman, J., et al., *Blood,* 85:139; Morgan et al. (1992) *Nucleic Acids Res.* 20:1293–1299), LXSN (Miller, A. D., et al. *Methods Enzymol.,* 217:581–599 (1993); Miller, A. D., et al. *BioTechniques,* 7:980–988 (1989); Miller, A. D., et al., *Mol. Cell Biol.,* 6:2895–2902 (1986); Miller, A. D. *Curr. Top. Microbiol. Immunol.,* 158:1–24 (1992)), and SAM-EN (Treisman, J., et al., *Blood,* 85:139) may also be used. Individual constructs carrying the genes encoding for the alpha and beta chains that comprise the receptor may be introduced into the T-lymphocytes or alternatively, an individual construct carrying the nucleic acid sequences encoding for both the α and β chains of the T-cell receptor may be in a single construct. Preferably, a retroviral vector, for example a vector with the murine moloney leukemia viral LTR promoting transcription of the T-cells receptor genes is used. In a preferred embodiment nonreplicating retroviral vectors are used. Alternatively, the genes can be expressed using an internal housekeeping promoter, such as that from the phosphoglycerol kinase (PGK) gene.

The α and β chains of the T-cell receptor could either be expressed on separate retroviral vectors, or on the same retroviral vector, separated by an internal ribosomal entry site (IRES) (Treisman, J., et al., *Blood,* 85:139; Morgan, R. A., et al., *Nucleic Acids. Res.,* 20:1293–1299 (1992)). Using an IRES-containing vector, allows both T-cell receptor genes to be translated from a single RNA message. Examples of where T-lymphocytes can be isolated, include but are not limited to, peripheral blood cells lymphocytes (PBL), lymph nodes, or tumor infiltrating lymphocytes (TIL), or blood. Such lymphocytes can be isolated from the individual to be treated or from a donor by methods known in the art and cultured in vitro (Kawakami, Y. et al. (1989) *J. Immunol.* 142:2453–3461).

The T-cells may be incubated with a retroviral producer cell line carrying retroviral expression vectors or with viral supernatant. Viability of the lymphocytes may be assessed by conventional methods, such as trypan blue dye exclusion assay. The genetically modified lymphocytes expressing the desired melanoma specific T-cell receptor may then be administered to a mammal, preferably a human, in need of such treatment in a therapeutically effective amount. The dosing regimes or ranges of lymphocytes used in the conventional tumor infiltrating lymphocyte (TIL) therapy (Rosenberg, et al. (1994) *Journal of National Cancer Institute,* Vol. 86:1159 may be used as general guidelines for the doses or number of T-lymphocytes to be administered to mammal in need of such treatment. By way of example, a range of about $1\times10^{10}$ to about $1\times10^{11}$ T-cells for each cycle of therapy may be administered in the methods provided herein. Examples of how these antigen specific T-cells can be administered to the mammal include but are not limited to, intravenously, intraperitoneally or intralesionally. Parameters that may be assessed to determine the efficacy of these transduced T-lymphocytes include, but are not limited to, production of immune cells in the mammal being treated or tumor regression. Conventional methods are used to assess these parameters. Such treatment can be given in conjunction with cytokines or gene modified cells (Rosenberg, S. A. et al. (1992) *Human Gene Therapy,* 3:75–90; Rosenberg, S. A. et al. (1992) *Human Gene Therapy,* 3:57–73) chemo-therapy or active immunization therapies. One of skill in the art will appreciate that the exact treatment schedule and dosages, or amount of T-lymphocytes to be administered may need to be optimized for a given individual.

This invention also relates to stem cells expressing chimeric receptors or T-cell receptors which recognize tumor antigens, provided herein. Chimeric receptor genes comprising a single chain Fv domain of a specific antibody and a second segment encoding at least a transmembrane and cytoplasmic domain of an immune cell such as a T-cell receptor, one of the chains from the CD3 receptor complex, an Fc receptor, CD28 receptor, or IL-2 receptor or similar cytoplasmic domains. In a preferred embodiment the chimeric receptor comprises the variable domains from monoclonal antibodies (MAb) linked to the $F_c$ receptor-associated γ chain, which is capable of mediating signal transduction in T-cells (Hwu et al. (1993) *Journal of Experimental Medicine* 178:361–366; Esher, et al. (1993) *PNAS* 90 720–724; Hwu et al (1993) *Journal of Immunology* 150:4104 and WO 93/19163 which are herein incorporated by reference.) Methods of isolating, enriching and culturing of hematopoietic stem cells are known to those skilled in the art (Tskamuto et al., U.S. Pat. No. 5,061,620 and Peault, U.S. Pat. No. 5,147,784 herein incorporated by reference.

Isolation of bone marrow, a source of hematopoietic stem cells, and retroviral transduction is performed by conventional methods (Bjorkstrand, B., et al., *Hum. Gene Ther.,* 5:1279–1286 (1994); Brenner, et al., *Lancet,* 342:1134–1137 (1993); Brenner, M. K., et al., *N.Y. Acad. Sci Gene Therapy for Neoplastic Disease* (Abstract 211993), 46:711; Brenner, M. K., et al. *Lancet,* 341:85–86 (1993); Brenner, M. K., et al. *J. Hematother,* 3:33–36 (1994); Brenner, M. K., et al. *J. Hematother,* 2:7–17 (1993); Brenner, M., et al. *Hum. Gene Ther.,* 5:481–499 (1994); Brenner, M. K., et al., *Ann. N.Y. Acad. Sci.,* 716:204–14 (1994); O'Shaughnessy, J. A., et al., *Hum. Gene Ther.,* 4:331–354 (1993); O'Shaughnessy, J. A., et al., *Hum. Gene Ther.,* 5:891–911 (1994); Blaese, R. M., et al., *Human Gene Ther.,* 4:521–527 (1993); Cassel, A., et al., *Exp. Hematol,* 21:585–591 (1993); Dunbar, C. E., et al. *Ann N.Y. Acad. Sci.,* 716:216–24 (1994); Bodine, D. M., et al., *Blood,* 82:1975–1980 (1993)]. By way of example, human CD34⁺ hematopoietic stem cells can be readily isolated from peripheral blood [Barrande C., et al. 1993. *Hybridoma,* 12(2):203; Kato K., and A. Radbruch. 1993. *Cytometry,* 14(4):384], and may be used as targets for retroviral-mediated gene transfer [Cassel A., et al. 1993. *Exp. Hematol.,* 21(4):585; Bregni M., et al. 1992. *Blood,* 80:1418]. The bone marrow isolated from a mammal may be enriched for CD34+ population by using an anti-CD34+ monoclonal antibody. The CD34+ cells may be cultured in media comprising IL-3, IL-6 and stem cell factor (SCF). The cells may be exposed to retroviral supernatant, harvested and reinfused into the mammal in need of such treatment.

The constructs containing the chimeric receptors or melanoma specific T-cell receptors may be introduced into the cells by conventional methodology including, but not limited to, microinjection, electroporation, viral transduction, transduction, or transfection using DEAE-dextran, lipofection, calcium phosphate, particle bombardment mediated gene transfer or direct injection of nucleic acid sequences encoding the T-cell receptors of this invention or other procedures known to one skilled in the art. In a preferred embodiment the bone marrow containing stem cells is incubated with viral supernatant or a producer cell line carrying the retroviral construct or constructs. Examples of vectors that can be used to express the chimeric receptors or melanoma antigen specific T-cell receptors of this invention include, but are not limited to retroviral vectors, vaccinia virus vectors, adenovirus vectors, herpes virus vector, fowl pox virus vector, adeno associated virus (AAV), plasmids, such as pCDNA3 (Invitrogen, San Diego, Calif.) or the baculovirus transfer vectors. By way of example, eukaryotic expression vectors that may be used include, but is not limited to, G1EN(Treisman, J., et al., *Blood,* 85:139 Morgan, et al. (1992) *Nucl. Acids Res.:* 20 1293–1299), LXSN (Miller, A. D., et al. *Methods Enzymol.,* 217:581–599 (1993); Miller, A. D., et al., *BioTechniques,* 7:980–988 (1989); Miller, A. D., et al. *Mol. Cell. Biol.,* 6:2895–2902 (1986); Miller, A. D., *Curr. Top. Microbiol. Immunol.,* 158:1–24 (1992)) or SAM-EN vectors (Treisman, J., et al. *Blood,* 85:139).

The stem cells carrying either the chimeric receptor or melanoma reactive T-cell receptors provided herein are administered in a therapeutically effective amount to a mammal preferably a human in need of such treatment. Preferred T-cell receptors to be used in this embodiment are shown in FIGS. 1A–1B and FIG. 2. Parameters to evaluate in treating the mammal include, but are not limited to study of differentiated hematopoietic cells for their ability to become activated by or specifically bind the antigen recognized by the introduced receptor gene, DNA analysis of peripheral blood lymphocytes and other tissues for presence of the introduced receptor gene, and immunohistochemical antibody studies of expression of the receptor gene. In addition, in vivo anti-tumor responses can be evaluated. Complete tumor eradication may require repeated treatments, combinations of intraperitoneal and intravenous therapy, or combinations with other treatment approaches. Tumor therapy using a variety of chimeric receptors or T-cell receptors targeting different antigens may also be used or necessary should antigen down-regulation or in vivo immunoselection of antigen-negative cells become evident.

The therapeutic efficiency of differentiated lymphocytes derived from stem cells transduced with the chimeric receptor gene may be enhanced by the addition of other receptor types. This invention therefore also relates to a chimeric receptor comprising an antibody variable region joined to cytoplasmic region of CD28 from a T-cell or a similar region which can provide a T-cell with costimulating signals. For example the CD28 receptor is activated by the costimulatory molecule B7 (Linsley, P. S., et al., *Proc. Natl. Acad. Sci. U.S.A.,* 87:5031–5035 (1990); Chen, L., et al. *Cell,* 71:1093–1102 (1992) Stein, et al. (1994) *Mol. & Cell Biol.* 14:3392).

Coadministration of a chimeric receptor gene consisting of the variable regions of a monoclonal antibody joined to the cytoplasmic domains of the CD28 receptor (SCFV-CD28) may be coadministered with other chimeric receptors. With both SCFV-γ and SCFV-CD28 receptors a T-cell could receive both TCR activation and costimulation signals upon contact with the antibody defined antigen.

This invention also relates to pharmacological compositions comprising the T-cell receptors and chimeric receptors of this invention and to pharmacolological compositions of cells transformed or transduced with these receptor genes. In addition, pharmacological compositions comprising expression vectors which contain the genes for the receptors are also intended to be encompassed by this invention. The formulations of the present invention, both for veterinary and for human use, comprise each component individually or as a composition as described above, together with one or more pharmaceutically acceptable carriers and, optionally, other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1–2.0M), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharide, amino acids, inorganic acids, and organic acids which may be used either on their own or as admixtures. These stabilizers are preferably incorporated in an amount of 0.11–10,000 parts by weight per part by weight of each component or the composition. If two or more stabilizers are to be used, their total amount is preferably within the range specified above. These stabilizers are used in aqueous solutions at the appropriate concentration and pH. The specific osmotic pressure of such aqueous solutions is generally in the range of 0.1–3.0 osmoles, preferably in the range of 0.8–1.2. The pH of the aqueous solution is adjusted to be within the range of 5.0–9.0, preferably within the range of 6–8. In formulating each component separately or as a composition of the present invention, anti-adsorption agent may be used.

Additional pharmaceutical methods may be employed to control the duration of action. Controlled release preparations may be achieved through the use of polymer to complex or absorb the proteins or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the 9-cis-retinoic acid or derivatives thereof alone or in combination with antineoplastic agents thereof into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the component may be combined with typical carriers, such as lactose, sucrose, starch, talc magnesium stearate, crystalline cellulose, methyl cellulose, carboxymethyl cellulose, glycerin, sodium alginate or gum arabic among others.

The administration of the compositions or of each individual component of the present invention may be for either a prophylactic or therapeutic purpose. The methods and compositions used herein may be used alone in prophylactic or therapeutic uses or in conjunction with additional therapies known to those skilled in the art in the prevention or treatment of cancer. Alternatively the methods and compositions described herein may be used as adjunct therapy. Veterinary uses are also intended to be encompassed by this invention.

All books, articles, or patents referenced herein are incorporated by reference. The following examples illustrate to various aspects of the invention but are in no way intended to limit the scope thereof.

EXAMPLE 1

T-cell Receptor Usage by Melanoma Specific Clonal and Oligoclonal TIL Lines

Methods and Materials

Generation of TIL lines and clones. TIL were generated from tumor biopsies of patients with metastatic melanoma treated at the Surgery Branch of the NCI, as previously described (Rosenberg S. A., et al. (1988) *N. Engl. J. Med.* 319, 1676–1680; Topalian, S. L., et al. (1987) *Journal of Immunol. Methods.* 102, 127–141). Briefly, tissue from surgical specimens was dissociated into single cell suspensions and cultured in complete medium (CM) consisting of either RPMI-1640 (Biofluids, Rockville, Md.) with 10% human AB serum (Bio-Whittaker, Walkersville, Md.) or AIM V serum free medium (Gibco Laboratories, Grand Island, N.Y.), supplemented with 10 µg/ml of gentamicin sulfate (Bio-Whittaker, Walkersville, Md.), 50 U/ml of penicillin, 146 µg/ml of L-glutamine (Gibco Laboratories, Grand Island, N.Y.) and 6000 International Units (IU)/ml of recombinant human IL-2 (rhIL-2) (provided by Cetus Corporation, Emeryville, Calif.). Growing cultures were supplemented with fresh CM every 2–3 days and cell density was maintained below $5 \times 10^5$ cells/ml. TIL 1200 was a 45 day old bulk TIL culture used for the treatment of patient 1200 (HLA-A1,A2; B8,B44). TIL C10-1 and TIL F2-2 were isolated from 1000 T-cells/well microcultures of a tumor digest from patient 1200. TIL 5 was isolated from a 4000 lymphocytes/well microculture of a tumor digest from patient 501 (HLA-A2,A24; B18,B35). TIL F11-21 was isolated from 1 cell/well microculture of bulk TIL obtained from patient 1102 (HLA-A2,A24; B55,B62). TIL A10 was isolated from 0.3 cell/well microculture of bulk TIL obtained from patient 537 (HLA-A1,A26; B44,B70). Tumor specificity and MHC restriction of each TIL was examined by lysis of a panel of HLA matched and mismatched melanoma lines, EBV transformed B cell lines, (Surgery Branch, NIH) Daudi (ATCC) and K526 (ATCC) in standard 4 hour $^{51}$Cr release assays (Hom, S. S., et al. (1993) *Cancer Immunol. Immunother.* 36, 1–8).

RNA isolation and cDNA synthesis. Total cellular RNA was isolated using guanidine isothiocyanate/acid-phenol method (Chomczynski, P., & Sacchi, N. (1987) *Anal. Biochem.* 162, 156–159) from $15 \times 10^6$ TIL. For PCR, first strand cDNA was synthesized from 1–5 µg of total RNA using oligo-dT$_{22}$ and Moloney Murine Leukemia Virus (MMLV) reverse transcriptase (Gibco-BRL, Grand Island, N.Y.) as described (Gubler, U., & Hoffman, B. J. (1983) *Gene.* 25, 263–269).

Generation and screening of cDNA libraries. cDNA libraries were generated for the TCR analysis of TIL 5 and TIL A10. First and second strand cDNA was synthesized from 2 µg of Poly A$^+$ RNA as described (Gubler, U., & Hoffman, B. J. (1983) *Gene.* 25, 263–269). Double stranded cDNA was cloned into Eco-RI sites of λ gt10, packaged in vitro and plated (Packagene Lambda DNA packaging system, Promega, Madison, Wis.). Recombinant λ phage were screened by plaque hybridization with $^{32}$P labeled TCR Cα or Cβ region probes (Nishimura, M. et al. (1994) *Journal of Immunotherapy* V16:85–94). λ clones containing TCR cDNAs were plaque purified 3 times and full length clones were identified by PCR using λ gt10 primers which flank the cloning site (Clonetech, Palo Alto, Calif.).

PCR Primers. V gene subfamily specific PCR primer sequences were designed based upon alignments of all known TCR Vα and Vβ gene sequences. All oligonucleotides were synthesized using an ABI 392 DNA/RNA synthesizer (Applied Biosystems). The Cα, Cβ primers used for anchor PCR and the Vα and Vβ sequences and specificity controls for PCR analysis are described (Ferradini, L., et al. (1991) *Eur. J.Immunol.* 21, 927–933; Ferradini, L., et al. (1991) *Eur. J.Immunol.* 21, 935–942; and Nishimura et al., 1994 *Journal of Immunotherapy* 16:85–94.

PCR conditions. T-cell receptor DNA fragments were amplified from cDNA using the polymerase chain reaction as described with the following modifications (Choi, Y., et al. (1989) *Proc. Natl. Acad. Sci.* 86, 8941–8945). Briefly, 1% of the first strand cDNA synthesized from each TIL was subjected to amplification in a 50 µl reaction containing 1 unit of Ampli-Taq (Perkin Elmer, Norwalk, Conn.), 200 µM dNTP (Pharmacia, Piscataway, N.J.), 1 µM Vα or Vβ subfamily specific primer, and 1 µM of the corresponding Cα or Cβ constant region primer. Amplifications were performed in a Perkin Elmer 9600 DNA thermocycler (Perkin Elmer, Norwalk, Conn.) using the following cycle profile: 30 cycles of 92° C. denaturation for 1 minute, 60° C. annealing for 1 minute, and 72° C. extension for 2 minutes. PCR products were separated on 2% agarose gels along with molecular size standards. Visualization of a band of the appropriate size on an ethidium bromide stained gel indicated the presence of that T-cell receptor (TCR) subfamily.

Anchor PCR. Amplification and cloning of TCR genes was performed by anchor PCR as described (Loh, E. Y., et al. (1989) *Science.* 243, 217–220) with a few modifications. In brief, first strand cDNA was treated with RNase H and purified over a GlassMax column (Gibco-BRL, Grand Island, N.Y.). One tenth of the purified cDNA was dC tailed using terminal deoxynucleotide transferase (Gibco-BRL, Grand Island, N.Y.). The amplification reaction was performed in a 50 µl final reaction volume using 25 ng of tailed cDNA, 4 pmoles of Anchor Primer (Gibco-BRL, Grand Island, N.Y.), 2 pmoles of either TCR Cα (Ferradini, L., et al., (1991) *Eur. J.Immunol.* 21, 927–933) or Cβ (Ferradini, L., et al. (1991) *Eur. J.Immunol.* 21, 935– 942) specific primers and 0.5 units of Taq DNA polymerase (Perkin-Elmer Cetus, Norwalk, Conn.). Amplification was performed for 35 cycles at 92° for 60 seconds, 54° for 60 seconds and 72° for 120 seconds followed by a 15 minute extension period at 72°.

Cloning and Sequencing. The PCR products were separated on a low melt agarose gel (Gibco-BRL, Grand Island, N.Y.), DNA fragments were purified using the PCR DNA purification system (Promega, Madison, Wis.) and cloned into the T/A vector, PCR II (Invitrogen, San Diego, Calif.). Cloned anchor PCR products were sequenced using the dideoxynucleotide chain termination method with T7 DNA polymerase (Sequenase 2.0, USB, Cleveland, Ohio) as described in Sanger, F., et al. (1977) *Proc. Natl. Acad. Sci. USA.* 74, 5463–5467). The resultant sequences were analyzed using the Genetics Computer Group, Inc. software package (Deveraux, J., et al. (1984) *Nucleic Acids Res.* 12, 387).

Reactivity and Specificity of TIL lines. Six CD8+ TIL lines were generated from four patients with metastatic melanoma. Tumor specificity was determined by assaying in vitro lysis of a panel of melanoma cell lines (Table 1). TIL-1200, TIL-5 and TIL-F2-2 were derived from HLA-A2+ patients and lysed HLA-A2+, but not HLA-A2− melanomas. TIL-C10-1 and TIL-F11-21 lysed only HLA-A1+ and HLA-B55+ melanoma targets, respectively. TIL-A10 lysed autologous tumor and did not lyse HLA-A1+ targets. Since it was not tested against allogeneic HLA-A26+, HLA-B44+ and HLA-B70+ targets, the restriction of TIL-A10 could not be defined. None of the TIL exhibited nonspecific lysis due to lymphokine-activated killer (LAK) or natural killer (NK) activity as demonstrated by lack of lysis of Daudi and K562.

Analysis of V gene usage by TIL lines. TCR repertoire was examined by PCR with V gene subfamily specific primers, and by sequence analysis of cloned anchor PCR products (TIL-F11-21, TIL-F2-2, TIL-C10-1, TIL-1200) or sequence analysis of clones from cDNA libraries (TIL-A10, TIL-5). TCR V gene usage by the six TIL is shown in Table 2. TIL-A10 (V$\alpha$ 2.2, V$\beta$ 4), TIL-5 (V$\alpha$ 1.1, V$\beta$ 7.3), TIL-F11-21 (V$\alpha$15, V$\beta$ 15) and TIL-F2-2 (V$\alpha$ 17, V$\beta$ 6.5) each expressed a single V$\alpha$ and a single V$\beta$ indicating clonality. TIL-1200 expressed two V$\alpha$ (V$\alpha$ 2, V$\alpha$ 9) and as many as six V$\beta$ (V$\beta$ 4, V$\beta$ 5, V$\beta$ 6, V$\beta$ 13, V$\beta$ 14, V$\beta$ 22) chains when analyzed by PCR with V gene specific primers. However, analysis of 25 consecutive TCR$\alpha$ anchor PCR clones and 13 consecutive TCR$\beta$ anchor PCR clones identified only V$\alpha$ 9 and V$\beta$ 22.1. Similar analysis have shown that the frequency of TCR anchor PCR products is proportional to the frequency of each clonotype in a T-cell population (Ferradini, L., et al. (1992) *Cancer Res.* 52, 4649–4654). Therefore, TIL-1200 consisted predominantly of a single T-cell clone expressing V$\alpha$ 9 and V$\beta$ 22.1. Sequence analysis of anchor PCR clones from TIL C10-1 revealed that all 15 TCR$\beta$ cloned anchor PCR products were V$\beta$ 13.6. However, sequence analysis of 20 consecutive TCR$\alpha$ anchor PCR clones revealed two V$\alpha$ genes, V$\alpha$ 8.2 (11 of 20 cloned anchor PCR products) and V$\alpha$ 14.1 (9 of 20 cloned anchor PCR products).

Analysis of D, J, and N diversity segment usage by TIL lines. The V-J and V-D-J junctional sequences are unique to each T-cell clonotype and contribute to TCR diversity. Occasionally, TCR rearrangements result in non functional gene products. In order to determine which TCR$\alpha$ gene contributes a functional gene product in TIL-C10-1 and to define its clonality, the V-J or the V-D-J regions of the cloned TCR genes from TIL C10-1 were sequenced (FIG. 1A). All 15 TIL-C10-1 TCR$\beta$ cloned products were comprised of V$\beta$13.6/D$\beta$1.1/J$\beta$1.5. Both TCR$\alpha$ chains found in TIL-C10-1 were productively rearranged and used V$\alpha$8.2/J$\alpha$49 (11/20) and V$\alpha$14.1/J$\alpha$32 (9/20). However, the amino acid translation of these TCR cDNAs indicated that only the V$\alpha$8.2/J$\alpha$49 transcripts can produce functional TCR$\alpha$ chains. While the V$\alpha$14.1/J$\alpha$32 cDNA can produce a full length TCR$\alpha$ protein, the J region lacks the correct amino acid sequence reported for J$\alpha$32 and the highly conserved FGXG motif (Koop, B. F., et al. (1993) *Genomics.* 84, 478–493). This motif is highly conserved both among the human and the murine J$\alpha$ segments (Koop, B. F., et al. (1993) *Genomics.* 84, 478–493)). The FXGX motif was also found in previously described functional TCRs containing J$\alpha$ 32 and in the other TCR$\alpha$ gene (V$\alpha$ 8.2/J$\alpha$ 49) expressed by TIL-C10-1, suggesting that it is essential for the structural integrity of TCR$\alpha$ gene products (Klein, M. H., et al. (1987) *Proc. Natl. Acad. Sci. USA.* 84, 6884–6888). Therefore the V$\alpha$ 14.1/J$\alpha$ 32/C$\alpha$ TCR transcript in TIL-C10-1 likely encoded a non functional TCR$\alpha$ chain and the TCR$\alpha$ chain encoded by V$\alpha$8.2/J$\alpha$49/C$\alpha$ was responsible for tumor recognition.

Since the CDR3 region encoded by the V-D-J and V-J junctions of the TCRs, are believed to be involved in antigen recognition, the junctions from the three HLA-A2 restricted TIL (TIL-F2-2, TIL-1200 and TIL-5) were compared (FIG. 1B). TCR V$\alpha$ and J$\alpha$ genes utilized by TIL-F2-2, TIL-1200 and TIL-5 were: V$\alpha$ 17/J$\alpha$ 42, V$\alpha$ 9/J$\alpha$ 16 and V$\alpha$ 1.1/J$\alpha$ 49, respectively. The TCR V$\beta$, D$\beta$ and J$\beta$ genes utilized by the HLA-A2 restricted TIL were: V$\beta$ 6.5/D$\beta$ 1.1/J$\beta$ 1.5 (TIL-F2-2), V$\beta$ 22.1/D$\beta$ 2.1/J$\beta$ 2.1 (TIL-1200) and V$\beta$ 7.3/D$\beta$ 2.1/J$\beta$ 2.1 (TIL-5). No restricted V gene usage or sequence homology at the N diversity regions was detected in the TCRs from the three HLA-A2 restricted TIL.

In most prior studies, TCR V gene usage was determined in T-cells isolated from tumor biopsies or from IL-2 expanded bulk TIL cultures (Solheim, J. C., et al. (1993) *J. Immunol.* 150, 800–811; Nitta, T., et al. (1990) *Science.* 249, 672–674; Karpati, R. M., et al. (1991) *J.Immunol.* 146, 2043–2051; Ferradini, L., et al. (1992) *Cancer Res.* 52, 4649–4654). Increases in the frequency of TCR V gene subfamilies were seen but the antitumor reactivity of the T-cells bearing these receptors was unknown. Furthermore, analysis by PCR, southern blotting, or immunofluorescence alone cannot distinguish between productively and nonproductively rearranged TCRs. Thus, this type of analysis is unable to determine which TCR $\alpha/\beta$ pair mediates melanoma antigen recognition. The TIL lines reported here are clonal in nature and specifically recognize human melanoma cells indicating the TCR clonotypes identified in these clones are responsible for in vitro lysis of melanoma targets.

In contrast to other studies which describe restricted TCR V gene usage in melanoma TIL (Solheim, J. C., et al. (1993) *J. Immunol.* 150, 800–811; Nitta, T., et al. (1990) *Science.* 249, 672–674; Sensi, M., et al. (1993) *J. Exp. Med.* 178, 1231–1246), the evidence presented here in this study and others (Karpati, R. M., et al. (1991) *J.Immunol.* 146, 2043–2051; Ferradini, L., et al. (1992) *Cancer Res.* 52, 4649–4654) indicates that multiple TCR V gene segments are capable of recognizing melanoma tumor associated antigens (TAA). Among the HLA-A2 restricted, melanoma specific, CTL clones that have been examined here, three different clonotypes were identified (V$\alpha$1.1/V$\beta$7.3, V$\alpha$9/V$\beta$22.1, and V$\alpha$17/V$\beta$6.5). Alignment of junctional TCR gene sequences and polypeptide sequences from these HLA-A2 restricted clonotypes, revealed no sequence homology or common structural motifs within the (complimentary determining region or N region) (CDR3). A comparison of TCR clonotypes from the five CTL clones and one oligoclonal line to four other clones which have been described finds no common TCR V gene usage and no homology within the CDR3 region (Sensi, M., et al. (1993) *J. Exp. Med.* 178, 1231–1246). Therefore, we find no evidence for restricted TCR V gene usage in melanoma specific CTL clones.

Three of the TIL analyzed in this study (TIL-F2-2, TIL-C10-1, TIL-1200) were isolated from a single patient. TIL-F2-2 and TIL-1200 were HLA-A2 restricted while TIL-C10-1 was HLA-A1 restricted. It follows that at least two different tumor epitopes were recognized by lymphocytes within the tumor bed of this patient, one presented in the context of HLA-A1 and the other presented in the context of HLA-A2. This result is consistent with the findings that two CTL clones from a single patient are recognize different T-cell epitopes (Sensi, M., et al. (1993) *J. Exp. Med.* 178, 1231–1246). In addition, multiple CTL clonotypes may be derived from a single patient that recognize one or more tumor associated epitopes presented in the context of the same restriction element.

Analysis of patient 1200 has provided information relevant to the development of for immunotherapy based cancer treatment. First, expansion of individual T-cell clonotypes is dependant on the culture conditions since two independent expansions of TIL from the same tumor biopsy yielded different clonotypes (Vα9/Vβ22.1 T-cells in TIL 1200 and Vα8.2/Vβ15 and Vα17/Vβ6.5 T-cells in TIL C10-1 and TIL F2-2). This result suggests that the culture conditions may influence the expansion of therapeutically relevant cells. Second, patient 1200 had a partial tumor regression following treatment with TIL 1200. Therefore, it is possible that a clonal or highly oligoclonal anti-tumor CTL population can successfully treat patients with advanced cancer. Third, the antigen recognized by TIL 1200 is expressed on most melanomas since all HLA-A2+ melanomas established in the Surgery Branch, NCI are lysed by this TIL.

TABLE 1

Specificity And Reactivity of Clonal And Oligoclonal TIL Lines

| Tumor Target | HLA-A Locus | HLA-B Locus | % lysis[a] by TIL line | | | | | |
|---|---|---|---|---|---|---|---|---|
| | | | 1200[b] | F2-2[b] | 5[c] | C10-1[b] | F11-21[d] | A10[e] |
| 501 | A2,A24 | B18,B35 | ND | ND | 52 | ND | 9 | 1 |
| 526 | A2,A3 | B50,B62 | 60 | 46 | 16 | 0 | ND | ND |
| 624 | A2,A3 | B7,B14 | 68 | ND | 36 | −2 | 14 | ND |
| 1102 | A2,A24 | B55,62 | 20 | 42 | ND | 2 | 61 | ND |
| 1143 | A2,A11 | B7,B60 | 67 | 25 | ND | 3 | ND | ND |
| 888 | A1,A24 | B52,B55 | 2 | 1 | −2 | 43 | 57 | ND |
| 938 | A1,A24 | B7,B8 | 8 | ND | ND | 55 | 10 | ND |
| 397 | A1,A10 | B8,B62 | 4 | ND | −2 | 42 | 13 | 3 |
| 537 | A1,A26 | B44,B70 | ND | ND | ND | ND | 6 | 21 |
| 586 | A29,A31 | B8,B44 | 1 | 1 | 0 | −2 | ND | ND |
| K562 | ND | ND | 3 | ND | ND | 10 | ND | ND |
| Daudi | ND | ND | 11 | −6 | −1 | −1 | 1 | 0.2 |
| EBV 888 | A1,A24 | B5,B22 | 2 | 2 | 2 | 2 | 7 | ND |
| EBV 501 | A2,A24 | B18,B35 | 6 | 12 | 10 | 10 | 7 | ND |

Melanoma specific reactivity was determined by standard 4 hour $^{51}$Cr release assays. Percent lysis identified in bold characters was significantly different from background lysis. Melanoma lines were derived and HLA typed as previously described (Nitta, T. et al. (1990) Science 249:672–674). Specific lysis for each TIL line was performed at least twice and representative experiments are shown.
ND = Not done.
[a]Percent lysis is shown for an effector to target ratio of 40:1 except for TIL 5 which is an effector to target ratio of 10:1.
[b]Derived from patient 1200 (HLA-A1,A2; B8,B44).
[c]Derived from patient 501 (HLA-A2,A24; B18,B35).
[d]Derived from patient 1102 (HLA-A2,A24; B55,B62).
[e]Derived from patient 537 (HLA-A1,A26; B44,B70).

TABLE 2

TCR V Gene Usage by Melanoma Specific TIL Clones and Oligoclonal Lines.

| TIL LINE | TCR α Usage | TCR β Usage | HLA Restriction |
|---|---|---|---|
| A10 | Vα2.2[a] | Vβ4 | ND[b] |
| 5 | Vα1.1[c] | Vβ7.3[c] | A2 |
| F2-2 | Vα17[d] | Vβ6.5[e] | A2 |
| C10-1 | Vα8.2[f],Vα14.1[f] | Vβ13.6[g] | A1 |
| 1200[h] | Vα9[i] | Vβ22.1[j] | A2 |
| F11-21 | Vα15[k] | Vβ15[l] | B55 |

[a]5 of five TCRα genes cloned into λgt10 phage and sequenced corresponded to Vα2.2.
[b]Not determined. A10 lysed only autologous tumor when tested against a small panel of melanomas.
[c]6 of six TCRα and TCRβ genes cloned into λ phage and sequenced corresponded to Vα1.1, Vβ7.3 respectively.
[d]Nine of 9 cloned anchor PCR products analyzed corresponded to Vα17.
[e]ten of 10 cloned anchor PCR products analyzed corresponded to Vβ 6.5.
[f]Analysis of 20 consecutive, cloned anchor PCR products revealed that 11 corresponded to Vα 8.2 and 9 correspond to Vα 14.1.
[g]Fifteen of 15 cloned anchor PCR products analyzed corresponded to Vβ13.6.
[h]PCR with family specific primers identified 2 Vα genes (Vα 2 and Vα 9) and 6 Vβ genes (Vβ 4,5,6,13,14,22) genes, but analysis of anchor PCR products revealed only Vα 9 and Vβ 22.1.
[i]Twenty-five of 25 cloned anchor PCR products analyzed by PCR and confirmed by sequencing expressed Vα9.
[j]Thirteen of 13 cloned anchor PCR products analyzed corresponded to Vβ22.1.
[k]Sixteen of 16 cloned anchor PCR products analyzed corresponded to Vα15.
[l]Thirteen of 13 cloned anchor PCR products analyzed corresponded to Vβ15.

EXAMPLE 2

Identification of Mart-1 Specific T-cell Receptors

Materials and Methods

Generation of TIL Lines and Clones. TIL were generated from tumor biopsies of 2 patients with metastatic melanoma as previously described [Rosenberg S. A., et al. *N. Engl. J. Med.,* 319:1676–1680. 1988]. Clone A42 was established by limiting dilution at 100 cells/well, with a proliferating frequency of 1:800, and clone 1E2 was established at 1 cell/well with a proliferating frequency of 1:43. The clones were cultured in round bottom microtiter plates with Interleukin-2 (IL-2) (120 International Unit(IU)/ml) in the presence of feeders ($1 \times 10^5$ allogeneic peripheral blood lymphocytes (PBL)/well irradiated to 5000 rads) with weekly stimulation using $1 \times 10^4$ autologous irradiated tumor cells/well.

Cell Lines. Melanoma cell lines C32, Malme3M, breast carcinoma cell line MDA231 (ATCC, Rockville, Md.), Ewing's sarcoma cell line RD-ES (M. Tsokos, NIH), COS-7 cells (W. Leonard, NIH), melanoma cell lines 397mel, 501mel, 526mel, 624mel, 677mel, 705mel, 888mel (established in the SB/NCI lab as described in Topalian S. L., et al. *J. Immunol.,* 142:3714–3724. 1989 and T2 cells [Kawakami Y, et al. *J. Exp. Med.,* 180:347–352. 1994] were maintained in RPMI with 10% FCS.

Peptide Synthesis. Peptides were synthesized by a solid phase method using a multiple peptide synthesizer (model AMS 422, Gilson Co. Inc, Worthington, Ohio) and purified by HPLC on a C-4 column (VYDAC, Hesperia, Calif.) with 0.05% trifluoroacetic acid (TFA)/water-acetonitrile. The M-series peptides are located in a hydrophobic putative transmembrane domain in MART-1 (Kawakami Y, et al. *J. Exp. Med.,* 180:347–352. 1994). The 10-amino acid peptides M10-3 and M10-4 contain the M9-2 sequence, with M10-3 having an additional glutamic acid at its $NH_2$ terminus and M10-4 having an extra isoleucine at its COOH-terminus. They are labeled as follows: M9-1 (TTAEEAAGI), M9-2 (AAGIGILTV), M10-3 (EAAGIGILTV), and M10-4 (AAGIGILTVI) (Peptides are shown in single letter code). Peptide G9-280 (YLEPGPVTA) is derived from gp100 as described [Cox A. L., et al. *Science,* 264:716–719. 1994].

Transient Transfection. cDNAs encoding for the melanoma antigens MART-1 and gp100, or for the HLA-A2.1 molecule were cloned into the mammalian expression plasmid pcDNA3 (Invitrogen, San Diego, Calif.) as previously described [Kawakami Y., et al. *Proc. Natl. Acad. Sci.,* 91:3515–3519. 1994; Kawakami Y, et al. *Proc. Natl. Acad. Sci. USA.,* 91:6458–6462. 1994]. COS-7 cells were then transfected with vectors encoding either MART-1 or gp100 (with or without HLA-A2.1 cDNA) by the DEAE-dextran method [Seed B., et al. *Proc. Natl. Acad. Sci.,* 84:3365–3369. 1987].

Assessment of Antigen Recognition by TIL HLA. restricted melanoma recognition by TIL was assessed with standard 5 hour $^{51}$Cr release cytotoxicity assays performed using melanoma and non-melanoma cell lines as targets [Kawakami Y., et al. *J. Exp. Med.,* 168:2183–2191. 1988]. The analysis of the ability of MART-1 or gp100 transfected COS-7 cells to stimulate IFN-γ release from TIL was evaluated using ELISA as previously described [Gaugler B., et al. *J. Exp. Med.,* 179:921–930. 1994]. Recognition of known antigenic peptides by TIL was assessed using T2 cells pre-incubated for 2 hr with a peptide at concentrations of either 1 µg/ml or 1 ng/ml. The ability of the peptide pulsed T2 cells to stimulate IFN-γ release from TIL was then assessed by enzyme-linked immunosorbent assay (ELISA).

RNA isolation and Anchor PCR. Total cellular RNA was isolated from $5 \times 10^6$ TIL using the guanidine isothiocyanate/acid phenol method [Chomczynski P., et al. *Anal. Biochem.,* 162:156–159. 1987]. For PCR, first strand cDNA was synthesized from 1–5 ug of total RNA using $(dT)_{22}$ and molony murine leukemia virus reverse transcriptase (GIBCO/BRL, Gaithersburg, Md.) as described [Gubler U., et al. *Gene,* 25:263–269. 1983]. Amplification and cloning of TCR genes was performed by anchor PCR using 5' anchor primer as described [Loh D. Y., et al. *Science,* 243:217–220. 1989] and either 3' TCR Cα-(CCTCAGCTGGACCACAGC (SEQ ID NO:34)) [Ferradini L., et al. *Eur. J. Immunol.,* 21:927–933. 1991] or Cβ (GGCAGACAGGACCCCTTG (SEQ ID NO: 35)) [Ferradini L., et al. Eur. J. Immunol., 21:935–942. 1991] specific primers. Amplification was performed for 35 cycles at 92° C. for 60 sec, 54° C. for 60 sec, and 72° C. for 120 sec followed by a 15 min extension period at 72° C.

Cloning and Sequencing. The PCR products were separated on a low melt agarose gel (GIBCO/BRL, Gaithersburg, Md.); DNA fragments were purified using the PCR DNA purification system (Promega, Madison Wis.) and cloned into the T/A vector PCR II (Invitrogen, San Diego, Calif.). Cloned anchor PCR products were sequenced using the dideoxynucleotide chain-termination method with T7 DNA polymerase (Sequenase 2.0, USB, Cleveland, Ohio) as described [Sanger F., et al. *Proc. Natl. Acad. Sci.,* 74:5463–5467. 1977]. The resultant sequences were analyzed using the Genetics Computer Group Inc., software package [Deveraux J., Nucleic Acids Res., 12:387–395. 1984].

Reactivity and Specificity of Clonal TIL Lines. Monoclonal $CD8^+$ TIL lines were generated from two HLA-A2+ patients with metastatic melanoma and tested extensively in multiple assays (thus Table 3 is representative). Clones A42 (Table 3) and 1E2 (Table 3) lysed a variety of HLA-A2+ melanoma cell lines and did not lyse HLA-A2⁻ melanoma lines. Non-melanoma HLA-A2+ cell lines including the breast cancer cell line MDA231 and Ewing's sarcoma cell line RD-ES were not lysed in separate cytotoxicity assays performed for both clones. These clones, therefore, appeared to specifically recognize allogeneic melanoma cell lines in an HLA-A2 restricted manner and both showed identical recognition profiles.

Transient transfection into COS-7 cells of the expression vector pcDNA3 containing cDNA for either MART-1 or gp100, along with the HLA-A2.1 gene, was performed to elucidate if either melanoma TAA was being recognized by the T-cell clones. Reactivity of TIL towards the COS-7 cells was then evaluated by measuring IFN-γ release. Both clones demonstrated specific reactivity towards MART-1$^+$/HLA-A2.1$^+$ COS-7 cells (Table 4). Uncloned TIL cultures known to recognize either gp100 (TIL 1200), MART-1 (TIL 501), or both (TIL 1143) were used as positive controls [Kawakami Y., et al. *Proc. Natl. Acad. Sci.,* 91:3515–3519. 1994; Kawakami Y, et al. *J. Exp. Med.,* 180:347–352. 1994]. Both clones, therefore seemed to recognize the MART-1 antigen expressed by melanoma cell lines.

To test whether the two clones recognized the same or different epitopes in the MART-1 antigen, A42 and 1E2 were stimulated with T2 cells preincubated with different MART-1 (M9-1, M9-2, M10-3, M10-4) or gp100 (G9-280) peptides. As shown in Table 5, both clones specifically released IFN-γ in response to M9-2 and M10-3 pulsed T2 cells (in a pattern similar to uncloned TIL lines 1235 and 660 which are known have MART-1 reactivity). The amount of IFN-γ released was greatest in response to M9-2 for both clones, and greater than the bulk TIL response. This response could also be demonstrated for both peptides after a thousand fold dilution of peptide pulsed on the T2 cells.

Analysis of the TCR α and β gene usage by Clones A42 and 1E2. To determine which TCR α and β genes contribute a functional gene product, and to confirm T-cell clonality, the V-J or the V-D-J regions of the cloned TCR genes from A42 and 1E2 were sequenced. All five of the productively rearranged A42 TCR β cDNA clones were comprised of Vβ7.3/Dβ2.1/Jβ2.7/Cβ2, and all of the TCR α chains (4 of 4) were Vα21/Jα42/Cα. The 12 1E2 TCR β chain clone products were Vβ3.1/Dβ1.1/Jβ1.1/Cβ1, and the TCR α chains were Vα25/Jα54/Cα (9 of 9) (FIG. 2). Amino acid translation of all of these TCR cDNAs indicated that the transcripts can produce functional products. The TCR utilized by these two T-cell lines, therefore, demonstrated clonality, different Vα and Vβ gene usage, and no homology at the N diversity regions.

Prior TCR utilization studies have been unable to clearly delineate whether or not restricted TCR V gene usage is prevalent in T-cells reacting with setting of tumor specific antigen. Although increases in the frequencies of some TCR V gene subfamilies were seen, the specific TCR's responsible for antitumor reactivity were unknown. In contrast to reports of tumor reactive T-cell clones which noted restricted TCR V gene usage in melanoma [Sensi M., et al. *J. Exp Med.* 178:1231–1248. 1993; Sensi M., et al. *J. Immunother.,* 12:207–211.1992], this study supports recent studies which have shown that multiple TCR V gene segments are capable of recognizing melanoma tumor associated antigens [Shilyansky J, et al. *Proc. Natl. Acad. Sci.,* 91:2829–2833. 1994; Sensi M., et al. *Melanoma Res.,* 194:261–271. 1991]. The analysis of TCR V gene usage by clones A42 and 1E2 presented here demonstrates that their variable and joining regions are distinct even though they recognize the same MART-1 epitope. Therefore, not only are multiple TCR V gene segments able to recognize melanoma antigens, but more than one TCR V gene is capable of recognizing the same specific antigenic peptide.

Another HLA-A2 restricted melanoma specific T-cell clone from the same patient as A42, clone 5 (Shilyansky J., et al. *Proc. Natl. Acad. Sci.,* 91:2829–2833. 1994), utilizes the same Vβ subfamily as A42 with a unique junctional region. Jurkat cells transfected with vectors encoding for clone 5 TCR, with the data demonstrating that clone 5 and A42 recognize the same epitope of MART-1 (Example 3)

Presented here for the time are TCR sequences which are capable of recognizing a specific epitope of a known melanoma associated antigen. Although TCR usage by melanoma specific clonal T-cell lines has been previously studied, the actual tumor antigen or antigenic epitope being recognized by the T-cell was unknown (Karpati R. M., et al. *J. Immunol.,* 146(6):2043–2051. 1991; Nitta T., et al. *Science,* 249:672–674. 1990; Ferradini R. M., et al. *Cancer Res.,* 52:4649–4654. 1992). In conclusion, this study is the first report of TCR sequences which are capable of recognizing a specific epitope of the MART-1 antigen. The two T-cell clones utilize distinct V-J and V-D-J regions, and so provide direct evidence that the immune system can provide more than one T-cell-receptor (TCR) capable of recognizing a specific tumor antigenic epitope.

TABLE 3

Lysis by CTL clones of HLA-A2+ melanomas

| | | % Lysis by Effector Cells | |
|---|---|---|---|
| Target[a] | HLA-A2 | Clone A42 | LAK Cells |
| 501mel | + | 50 | 26 |
| 526mel | + | 37 | 40 |

TABLE 3-continued

Lysis by CTL clones of HLA-A2+ melanomas

| | | | |
|---|---|---|---|
| 624mel | + | 36 | 27 |
| 677mel | + | 47 | 54 |
| 705mel | + | 57 | 14 |
| Malme3M | + | 57 | 35 |
| C32 | + | 15 | 22 |
| 397mel | − | 0 | 43 |
| 888mel | − | 1 | 63 |

| | | % Lysis by Effector Cells | |
|---|---|---|---|
| Target[a] | HLA-A2 | Clone 1E2 | LAK Cells |
| 501mel | + | 44 | 68 |
| 526mel | + | 94 | 94 |
| 624mel | + | 24 | 24 |
| 677mel | + | 16 | 79 |
| 705mel | + | 45 | 44 |
| Malme3M | + | 65 | 65 |
| C32 | + | 6 | 41 |
| 397mel | − | 0 | 68 |
| 888mel | − | 4 | 34 |

[a]Two separate 5-hr $^{51}$Cr release assays performed at an effector/target cell ratio of 20:1 for Clones 1E2 and A42 and LAK cells. All targets shown were melanoma cell lines. Prior testing against non-melanoma cell lines demonstrated no lysis.

TABLE 4

MART-1 specificity of CTL clones

| | | IFN-γ Secretion (pg/ml) | | | | |
|---|---|---|---|---|---|---|
| Stimulator Cell Line | Transfected cDNA | TIL 1200 | TIL 501 | TIL 1143 | Clone A42 | Clone 1E2 |
| COS 7 | none | <10 | <10 | 13 | <10 | <10 |
| COS 7 | HLA A2.1 | <10 | <10 | 23 | <10 | <10 |
| COS 7 | MART-1 | <10 | <10 | 90 | <10 | <10 |
| COS 7 | gp100 | <10 | <10 | 86 | <10 | <10 |
| COS 7 | HLA A2.1 + MART-1 | <10 | 121 | 986 | 730 | 1341 |
| COS 7 | HLA A2.1 + gp100 | 451 | <10 | 199 | <10 | <10 |

Reactivity of TIL towards COS-7 cells transiently transfected with cDNA for either MART-1 or gp100 (with or without HLA-A2.1) was evaluated by the specific release of IFN-γ. TIL alone backgrounds have been subtracted. Uncloned TIL cell lines known to recognize either gp100 (TIL 1200), MART-1 (TIL 501), or both (TIL 1143) were used as positive controls.

TABLE 5

MART-1 epitope specificity of CTL clones

| | | | IFN-γ Secretion (pg/ml) | | | |
|---|---|---|---|---|---|---|
| Stimulator Cell Line | Peptide (μg/ml) | None | TIL 1235 | TIL 660 | Clone A42 | Clone 1E2 |
| None | none | 12 | 66 | 66 | 34 | 24 |
| 624mel | none | 10 | 852 | 585 | 772 | 2701 |
| 397mel | none | 12 | 16 | 27 | 18 | 29 |
| T2 | none | 51 | 26 | 84 | 35 | 51 |
| T2 | M9-1(1) | 14 | 11 | 21 | 16 | 18 |
| T2 | M9-1(0.001) | 8 | 10 | 13 | 13 | 13 |
| T2 | M9-2(1) | 25 | 861 | 2328 | >20000 | 16517 |
| T2 | M9-2(0.001) | 24 | 24 | 60 | 208 | 805 |
| T2 | M10-3(1) | 28 | 815 | 1116 | 765 | 5247 |
| T2 | M10-3(0.001) | 40 | 27 | 77 | 35 | 1369 |
| T2 | M10-4(1) | 11 | 24 | 52 | 22 | 24 |
| T2 | M10-4(0.001) | 8 | 11 | 32 | 12 | 11 |

TABLE 5-continued

MART-1 epitope specificity of CTL clones

| Stimulator Cell Line | Peptide (μg/ml) | IFN-γ Secretion (pg/ml) | | | | |
|---|---|---|---|---|---|---|
| | | None | TIL 1235 | TIL 660 | Clone A42 | Clone 1E2 |
| T2 | g9-280(1) | 15 | 15 | 1321 | 19 | 21 |
| T2 | g9-280(0.001) | 10 | 21 | 840 | 10 | 12 |

The ability of tumor or peptide-pulsed T2 cells to mediate IFN-γ release from TILS was assessed via enzyme-linked immunosorbent assay. As positive controls, HLA-A2 restricted TIL 1235 and 660 recognize MART-1 or MART-1 and gp100 respectively. Prior to the assay, T2 cells were incubated for 2 h with MART-1 (M9-1, 9-2, 10-3, 10-4) or gp 100 (G9-280) peptides, 642mel and 397mel are HLA-A2-positive and -negative tumor lines, respectively.

EXAMPLE 3

Characterization of the Functional Specificity of Cloned T-cell Receptor Heterodimer Recognizing the Mart-1 Melanoma Antigen Materials and Methods Cell Lines. Melanoma cell lines 397mel, 501mel, 624mel, 888mel (established in the Surgery Branch, NCI as described [Topalian S. L., et al. 1989. *J Immunol.*, 142:3714]) and T2 cells [Kawakami Y., et al. 1994. *J. Exp. Med.*, 180:347] were maintained in RPMI with 10% FCS. 624mel was cloned in limiting dilution and screened via FACS analysis using HLA-A2 specific mAb BB7.2 (ATCC, Rockville Md.) for high (624mel+) and MHC class I antigen negative (624mel−) clones. Jurkat T-cell line (ATCC, Rockville, Md.) was maintained in DMEM with 10% FCS. Three CD8+ TIL lines were generated from tumor biopsies of patients with metastatic melanoma as previously described [Rosenberg S. A. 1992. *J. Clin. Oncol.*, 10:80]. Melanoma antigen specificity for TIL 1235 (MART-1), and 1200 (gp100) have been previously described [Kawakami Y., et al. 1994. *Proc. Natl. Acad. Sci.*, 91:3515; Kawakami Y., et al. 1994. *J. Exp. Med.*, 180:347].

Peptide Synthesis. Peptides were synthesized by a solid phase method using a multiple peptide synthesizer (model AMS 422, Gilson Co. Inc, Worthington, Ohio) and purified by HPLC on a C-4 column (VYDAC, Hesperia, Calif.) with 0.05% trifluoroacetic acid (TFA)/water-acetonitrile. The MART-1 series peptides are located in a hydrophobic putative transmembrane domain in MART-1 [Kawakami Y., et al. 1994. *J. Exp. Med.*, 180:347]. The sequence of the MART-1 peptides used in this study are as follows: MART-$1_{(22-30)}$ (TTAEEAAGI (SEQ ID NO:27)), MART-$1_{(27-35)}$ (AAGIGILTV (SEQ ID NO:28)), MART-$1_{(32-40)}$ (ILTVILGVL (SEQ ID NO:30)), MART-$1_{(26-35)}$ (EAAGIGILTV (SEQ ID NO:29)), and MART-$1_{(27-36)}$ (AAGIGILTVI (SEQ ID NO: 31)). The 10-amino acid peptides MART-$1_{(26-35)}$ and MART-$1_{(27-36)}$ contain the 9-amino acid minimal determinant MART-$1_{(27-35)}$ with MART-$1_{(26-35)}$ having an additional glutamic acid at its $NH_2$ terminus and MART-$1_{(27-36)}$ having an extra isoleucine at its COOH-terminus. Peptide gp$100_{(457-465)}$ (LLDGTATLRL (SEQ ID NO:32)) and gp$100_{(280-288)}$ (YLEPGPVTA (SEQ ID NO: 33)) were derived from gp100 as described [Kawakami Y., et al. 1994. *Proc. Natl. Acad. Sci.*, 91:6458; Cox A. L., et al. 1994. *Science*, 264:716].

DNA Constructs. Full length TCR α and β genes were amplified by polymerase chain reaction (PCR) from a λ phage TIL clone 5 cDNA library [Example 1; Shilyansky J., et al. (1994). *Proc. Natl. Acad. Sci.*, 91:2829]. Vα1 5' (CTCGAGGTTCAGCCATGCTCCTGG) (SEQ ID NO:36), Cα 3' (GATGGCGGAGGCAGTCTCTG) (SEQ ID NO:37) [Hall and Finn (1992) *Biotechniques* 13:241–257], Vβ7.3 5' (CTCGAGAGCATGGGCTGCAGGCTG) (SEQ ID NO:38), and Cβ2 3' (AAAGGATCCGAGCTAGCCTCTGGAATCCTTTC) (SEQ ID NO: 39) primers were used for the amplification as described (Shilyansky J., et al. (1994). *Proc. Natl. Acad. Sci.*, 91:2829). Resultant PCR DNA fragments were then cloned into the T/A vector PCR II (Invitrogen, San Diego, Calif.). The Vα1 gene was then ligated into the pCDNA3 expression vector (Invitrogen, San Diego, Calif.) containing the neomycin resistance gene and a CMV eukaryotic promoter, and the Vβ7.3 gene was ligated into a modified pCDL expression vector containing the SRα promoter [Engel I., et al. *Science*, 256:1318]. Resultant clones were screened by PCR using TCR specific cloning primers, and sequenced using the dideoxynucleotide chain-termination method with T7 DNA polymerase (Sequenase 2.0, USB, Cleveland, Ohio) as described [Sanger F., et al. (1977). *Proc. Natl. Acad. Sci.*, 74:5463].

FACS analysis. Jurkat T-cell receptor Vβ8 specific mAb C305.2 [Weiss A., and J. D. Stobo. 1984. *J. Exp. Med.*, 160:1284] (courtesy A. Weiss, HHMI, UCSF, San Francisco Calif.), goat-anti-mouse IgG1 (Becton Dickenson, San Jose, Calif.) goat anti mouse IgG-FITC (Becton Dickenson, San Jose, Calif.), anti-Leu-4 (CD3) (Becton Dickenson, San Jose, Calif.), W6/32 (anti-HLA A,B,C) (Sera-Lab, Sussex, England), and anti-TCR-1 (Becton Dickenson, San Jose, Calif.) were used for co-modulation experiments as previously described [Geisler C., et al. 1990. *J Immunol.*, 145:1761]. Briefly, $1 \times 10^6$ Jurkat transfectants were incubated for 12 hours at 37° C. with or without 100 μl of C305.2 mAb supernatant. Subsequently, the cell lines were washed 3x with FACS buffer (PBS containing 5% FCS and 0.05% Na azide) and re-stained with C305.2 to verify the down modulation of autologous TCR. Subsequent staining was performed with anti-CD3 or anti-TCR antibody to demonstrate the presence of transfected TCR heterodimers on the cell surface. HLA-A2 specific mAb BB7.2 (ATCC, Rockville Md.) was used to identify high and low class I expressing tumor clones as described.

Transfections. Jurkat cells were transfected via electroporation (250 V, 800 mF) using 20 μg of plasmid DNA (2 μg of pCDNA3 TCRα neomycin selectable plasmid and 18 μg of pCDL TCR β plasmid) and $1 \times 10^7$ cells in a total volume of 250 μl PBS. The cells were then incubated at 37° C. in six well plates containing 5 ml DMEM and 10% FCS. After 12 hours, G418 (Gibco Grand Island, N.Y.) was added at a concentration of 1 mg/ml. Four days later, viable cells were isolated over a Ficoll gradient (Organon Teknika, Durham, N.C.) and cultured in T-75 flasks (Nunc Inc., Napierville, Ill.). The media was then changed weekly until neomycin resistant cells grew to adequate numbers for testing (approximately $1 \times 10^7$ cells at three weeks). Following initial selection the concentration of G418 was lowered to 400 μg/ml. Jurkat transfectants were cloned by limiting dilution at 1 cell/well and screened for IL-2 production by ELISA as described.

Antigen recognition assays. T2 cells pre-incubated for 2 hr with peptide were washed 2x with PBS and then added to effector cells at a 1:1 ratio for a total of $1 \times 10^6$ cells/ml in a 48 well plate. Phorbol Myristate Acetate (PMA) (5 ng/ml, Sigma, St. Louis, Mo.) was added to wells containing Jurkat effector cells. The ability of the peptide pulsed T2 cells to stimulate cytokine release from Jurkat transfectants or TIL was then assessed by ELISA (RD systems, Minneapolis, Minn.). Jurkat transfectants were assessed for recognition of melanoma tumor lines by incubating with HLA-A2 positive (501mel, 624mel+) or HLA-A2 negative (397mel, 624mel−, 888mel) tumor cells in a 48 well plate for 12 hours at a 1:1 ratio for a total of $1 \times 10^6$ cells in 1 ml of media. TIL lines 1235 and 1200 were used under similar conditions as positive controls. The ability of the tumor to stimulate cytokine release from Jurkat transfectants or TIL was then assessed by ELISA (RD systems, Minneapolis, Minn.).

Figure 3B:
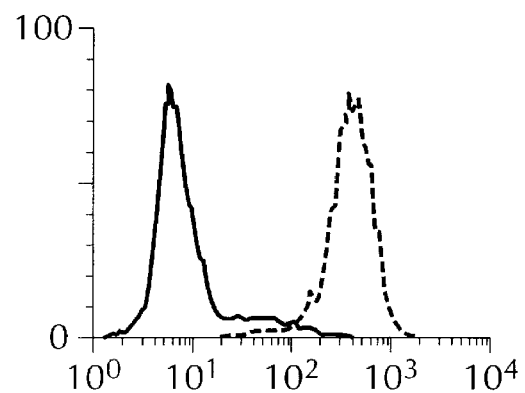
Figure 3C:
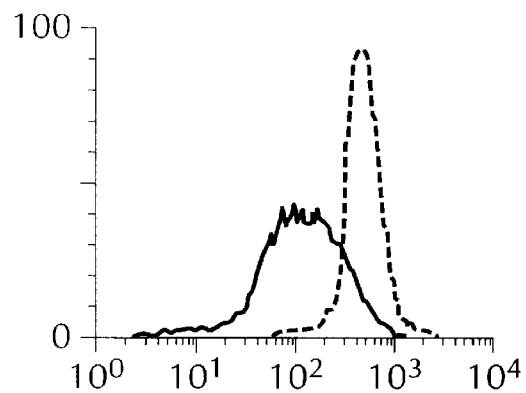
Figure 3D:
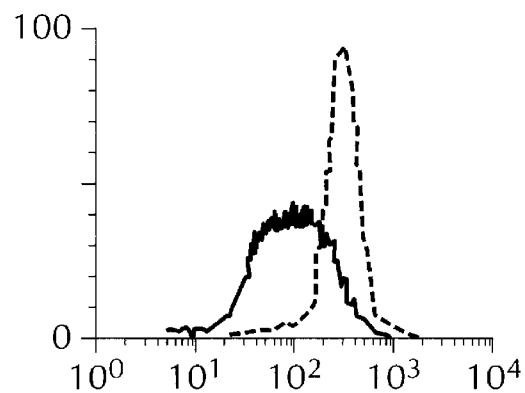
Figure 3E:
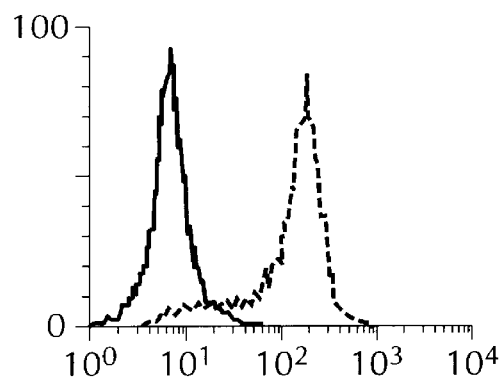
Figure 3F:
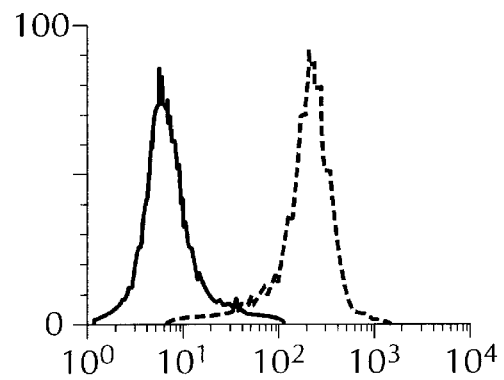
Figure 3G:
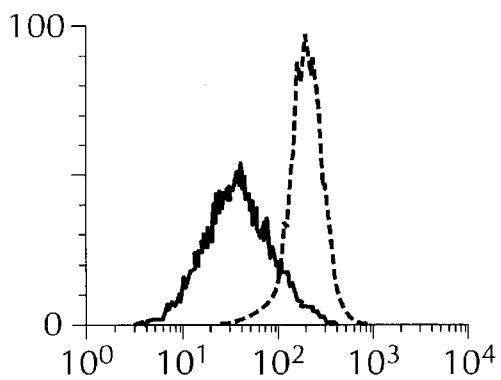
Figure 3H:
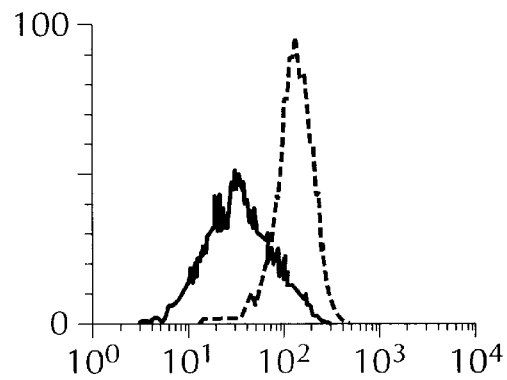
Figure 3I:
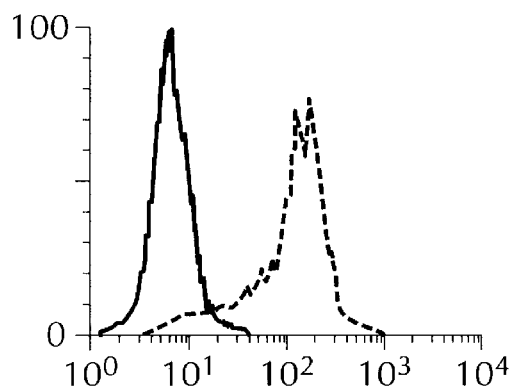
Figure 3J:
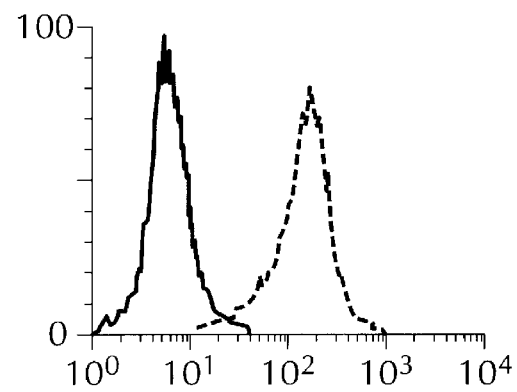
Figure 3K:
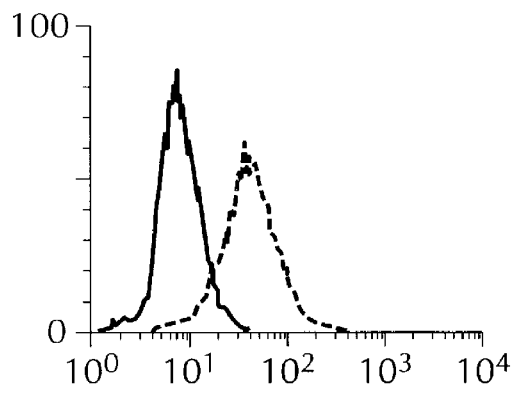
Figure 3L:
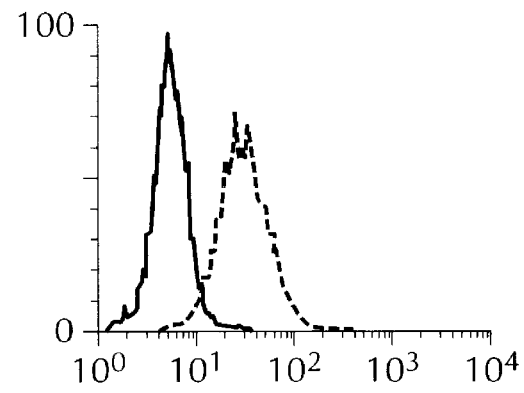

Cell Surface Expression of Clone 5 TCR. Since Jurkat cells express endogenous TCR, and no sub-family specific antibodies are currently available which specifically stain either the α or β chains of the clone 5 TCR (Vα1,Vβ7.3), a more involved method was required to demonstrate the surface expression of the transfected TCR. Jurkat clone 5 TCR bulk transfectant cell lines, and transfected Jurkat clones 13 and 22, were incubated overnight with or without Jurkat T-cell receptor β chain specific mAb C305.2 (Vβ8) to down modulate the expression of endogenous TCR. The resultant cultures were then washed at 4° C. in FACS buffer containing 0.05% azide, to prevent re-expression of the endogenous TCR, and stained with pan-specific anti-TCR-1, anti-HLA-A2, or anti-CD3 mAbs. All of the cultures incubated with C305.2 showed down-modulation of the endogenous receptor as indicated by the lack of staining with C305.2 (FIG. 3C). Comparison of the transfected to non-transfected Jurkat cell lines, after down modulation of endogenous receptor on the cell surface, demonstrated a persistent expression of both CD3 and TCR in the clone 5 TCR transfected cell lines (FIG. 3A, FIG. 3B). Pretreatment with C305 mAb had no effect on the level of MHC class I expression on any of the Jurkat lines tested. These results demonstrated the surface expression of non-endogenous TCR in Jurkat cell lines transfected with clone 5 T-cell receptor genes (TCR).

Clone 5 TCR recognition of MART-1 peptide. TIL clone 5 previously had been shown to be capable of recognizing HLA-A2$^+$ melanoma [Shilyansky J., et al. (1994)]. Proc. Natl. Acad. Sci., 91:2829]. To date every melanoma TIL culture tested has recognized either MART-1 or gp100 antigens (or both) [Kawakami Y., et al. 1994. J. Exp. Med., 180:347]. Additionally, a MART-1 specific T-cell clone, A42, derived from the same parental TIL line as clone 5 which shares the same Vβ7.3 subfamily as the clone 5 TCR (see Example 2). Initial screening was performed to determine whether the clone 5 TCR complex expressed on the cell surface was a functional heterodimer, and to elucidate which melanoma TAA it was capable of recognizing. Jurkat bulk transfectants were stimulated with T2 cells preincubated with different MART-1 (MART1$_{(22-30)}$, MART-1$_{(27-35)}$, MART-1$_{(32-40)}$, MART-1$_{(26-35)}$, MART-1$_{(27-36)}$) or gp100 (gp100$_{(457-465)}$) peptides. TIL 1235 and TIL 1200 were used as positive controls. TIL 1235 recognized MART-1$_{(27-35)}$, MART-1$_{(26-35)}$, MART-1$_{(27-36)}$, and TIL 1200 recognized gp100$_{(457-465)}$. The ability of peptide-pulsed T2 cells to stimulate IL-2 release from Jurkat cells or GM-CSF release from TIL was then assessed by ELISA. Jurkat bulk transfectant cells were cloned by limiting dilution to isolate a pure population of Jurkat TCR+ cells with 8 of 28 clones screening positive for IL-2 production. The clones with the highest level of stimulated IL-2 production (clones 13 and 22) were chosen for use in further assays.

Jurkat clone 5 TCR transfectants specifically recognized T2 cells pulsed with the MART-1$_{(27-35)}$ peptide, as shown in Table 6. Jurkat clone 5 TCR$^+$ cell line recognition patterns of MART-1$_{(27-35)}$ peptides were similar to several MART-1 specific TIL lines, including TIL 1235, which showed recognition of MART-1 peptides MART-1$_{(27-35)}$, MART-1$_{(26-35)}$, and MART-1$_{(27-36)}$ (Table 6) [Cox A. L., et al. 1994. Science, 264:716]. By contrast, TIL A42 (derived from the same parental TIL culture as clone 5) and TIL 1E2 were capable of recognizing MART-1 peptides MART-1$_{(27-35)}$, and MART-1$_{(26-35)}$, but not MART-1$_{(27-36)}$ (which contains the MART-1$_{(27-35)}$ sequence having an extra isoleucine at its COOH-terminus) [Example 2; Cole D. J., et al. 1994. Can. Res. 54:5265–5268].

Figure 4:
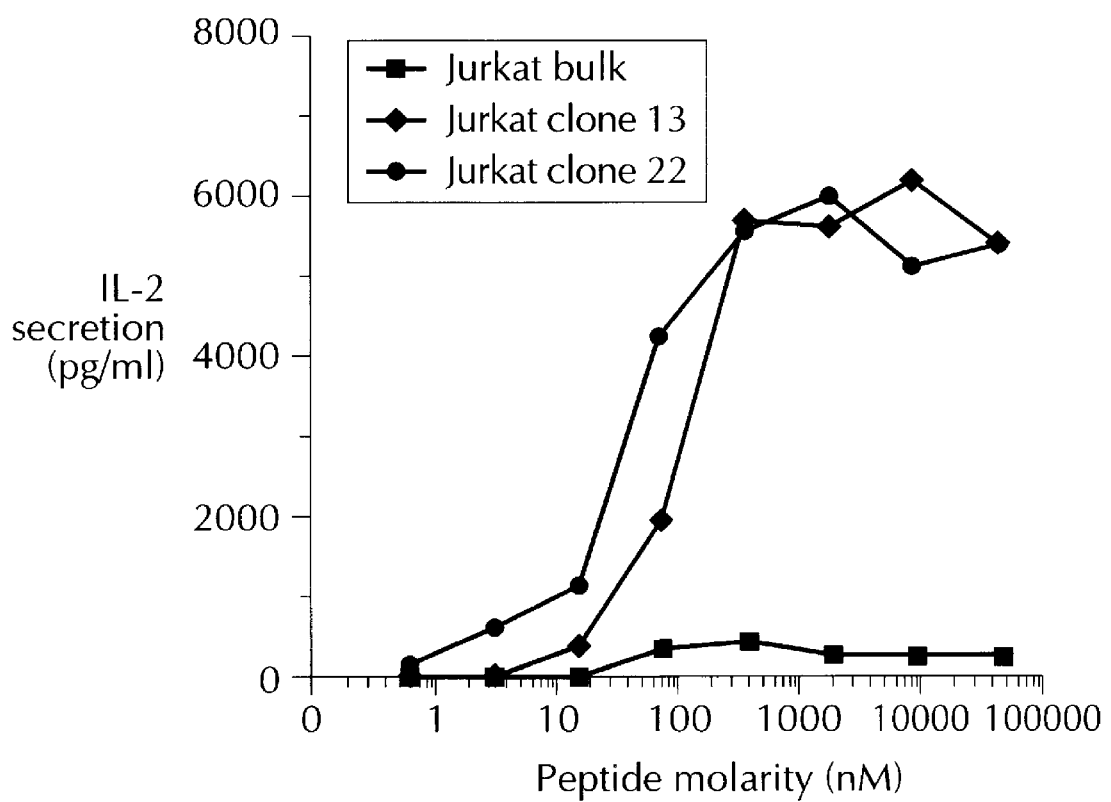
FIG. 4 shows graphic representation of IL-2 production by clone 5 TCR transfected (bulk, clone 13, and clone 22) Jurkat cell lines at varying levels of peptide concentration. The sensitivity of Jurkat TCR transfectant response to antigen stimulation was assessed by performing a series of 5×serial dilutions of the immunodominant M9-2 peptide (starting with a maximum concentration of 50 mM) pulsed on T2 cells and subsequently evaluating the ability of the T2 cells to mediate IL-2 release from the Jurkat cells. Relative sensitivity was determined from determining the concentration of peptide required to attain 50% of maximal cytokine response.

Characterization of the sensitivity of peptide recognition by the monoclonal Jurkat clone 5 TCR$^+$ cell lines was performed using T2 cells pre-incubated with a MART-1 peptide diluted over a range of 50 mM to 640 pM. The concentration of peptide required to provide 50% of maximal IL-2 stimulation in the range of 50–200 nM (FIG. 4). Both clones were more sensitive to peptide that the bulk cell line alone.

Clone 5 TCR recognition of Melanoma cell lines. Having defined the MART-1 specificity of clone 5 TCR, the ability of Jurkat clone 5 TCR$^+$ cell lines to recognize MART-1 positive melanoma tumor cells was evaluated. Monoclonal Jurkat clone 5 TCR$^+$ cells were therefore tested for their ability to recognize HLA-A2$^+$ melanoma cell lines using the same conditions for cytokine release as the T2 cell assay. Recognition of tumor by the Jurkat cell lines did not occur (Table 7). Since the level of HLA-A2 expression and amount of MART-1 peptide available on the tumor cell surface are factors which could affect the ability of Jurkat clone 5 TCR$^+$ cells to recognize tumor, the assay conditions were altered to improve these parameters. A ten-fold increase in the number of tumor cells/well or up regulation of tumor class I expression using a 48 hr pre-incubation with IFN-γ (verified by FACS analysis,) did not result in stimulation of Jurkat signaling. Only after loading the tumor cells with relevant peptide by pre-incubating them for 2 hours with MART-1$_{(27-35)}$ did a modest level of recognition by the Jurkat TCR$^+$ clones occur (Table 7). Thus, in contrast to TIL, monoclonal Jurkat clone 5 TCR$^+$ cell lines are unable to recognize endogenous MART-1 antigen on HLA A2$^+$ tumor cells as well as when it is pulsed onto T2 cells.

Several melanoma tumor associated antigen have been cloned and the epitopes recognized by TIL from melanoma patients identified [Van der Bruggen P., et al. 1991. Science, 254:1643; Brichard V., et al. 1993. J. Exp. Med., 178:489; Gaugler B., et al. 1994. J. Exp. Med., 179:921; Kawakami Y., et al. 1994. Proc. Natl. Acad. Sci., 91:3515; Kawakami Y., et al. 1994. Proc. Natl. Acad. Sci., 91:6458; Cox A. L., et al. 1994. Science, 264:716]. Since TIL are a heterogenous population of T-cells and consequently, it has been difficult to identify the T-cell clonotypes within a bulk TIL which culture recognize tumor antigen and mediates the anti-tumor responses observed in vivo [Nishimura M. I., et al. (1994). J. Immunother., 16:85–94).

This study is the first report of the reconstitution and characterization of a functional tumor antigen specific T-cell receptor heterodimer in an alternate cell line. The transfer of the TCR from a melanoma reactive clone (clone 5) to Jurkat cells has immortalized the tumor specific reactivity of clone 5 and allowed the determination of which TAA it recognized. Jurkat transfectants expressing the clone 5 T-cell receptor recognized the same MART-1 peptides as the bulk TIL (Table 6). Even though clones 5 and A42 were derived from the same patient, used the same Vβ subfamily gene (Vβ7.3), and recognized the same MART-1 9-mer (MART- $1_{(27-35)}$) [Example 3; Cole et al (1994) *Cancer Research*, 54:5265–5261], they had slightly different fine specificity. While both clones recognized the MART-1 10-mer, MART-$1_{(26-35)}$, only clone 5 recognized MART-$1_{(27-36)}$ (both 10-mers contain the core MART-$1_{(27-35)}$ minimal determinant with MART-$1_{(26-35)}$ having an extra glutamic acid at its NH2 terminus and MART-$1_{(27-36)}$ having an extra isoleucine at its COOH-terminus). Given the limited ability to expand tumor specific T-cell clones, transfer of TCR genes into Jurkat cells may provide a useful method to immortalize tumor reactive T-cell clones in order to identify and characterize the fine specificity of these clones.

Stimulation of clone 5 Jurkat cells by MART-$1_{(27-35)}$ pulsed T2 cells but not by melanoma cells indicated that there is more to T-cell activation than the TCR-peptide-MHC interaction. The level of antigenic peptide on the surface of the tumor cell appears to be important in recognition of melanoma antigens since HLA-A2$^+$ melanoma cells were able to stimulate the clone 5 Jurkat cells only after preincubation with the MART-$1_{(27-35)}$ peptide (Table 7). However, the low level of IL-2 release by peptide pulsed tumor cells relative to peptide pulsed T2 cells suggests that peptide levels alone cannot completely account for the inability of tumor cells to stimulate the Jurkat transfectants. Furthermore, the peptide concentration required for stimulation of the Jurkat transfectants is not very different from the concentration required to stimulate normal T-cells. T2 cells pulsed with MART-$1_{(27-35)}$ at concentrations as low as 5–10 nM can stimulate our Jurkat clones to secrete IL-2 (FIG. 4). Similarly, TIL clone A42 was stimulated to secrete GM-CSF by T2 cells pulsed with MART-$1_{(27-35)}$ at concentrations as low as 1 nM [Kawakami Y., et al. 1994. *J. Exp. Med.*, 180:347]. Therefore, both the TIL clone and the Jurkat transfectants require similar concentrations of peptide for stimulation.

Lack of tumor cell recognition by the clone 5 Jurkat cells is more likely due to expressing a TCR derived from an MHC class I restricted, CD8$^+$ T-cell clone in CD4$^+$ T-cell leukemia line. Lack of expression of CD8$^+$ on the Jurkat cell might account for their inability to be stimulated by tumor cells. It is also possible that T2 and melanoma cells differentially express the appropriate adhesion molecules required for efficient stimulation of the Jurkat transfectants.

TABLE 6

HUMAN CLONE 5 TCR EPITOPE MAP

| | | Responder Cells | | | | | | |
|---|---|---|---|---|---|---|---|---|
| Stimulator Cell Line | Peptide (2.5 umol) | Jurkat None[a] | Jurkat neo[a] | Jurkat bulk[a] | Jurkat Clone 13[a] | Clone 22[a] | TIL 1235[b] | TIL 1200[b] |
| None | None | <10 | <10 | <10 | <10 | <10 | <10 | <10 |
| None | MART-$1_{(22-30)}$ | <10 | <10 | <10 | <10 | <10 | 15 | <10 |
| None | MART-$1_{(27-35)}$ | <10 | <10 | <10 | <10 | <10 | <10 | 22 |
| None | MART-$1_{(32-40)}$ | <10 | <10 | <10 | <10 | <10 | <10 | <10 |
| None | MART-$1_{(26-35)}$ | <10 | <10 | <10 | <10 | <10 | <10 | 21 |
| None | MART-$1_{(27-36)}$ | <10 | <10 | <10 | <10 | <10 | <10 | <10 |
| None | gp100$_{(457-465)}$ | <10 | <10 | <10 | <10 | <10 | <10 | <10 |
| T2 | None | <10 | <10 | <10 | <10 | <10 | <10 | 21 |
| T2 | MART-$1_{(22-30)}$ | <10 | <10 | <10 | <10 | <10 | 21 | <10 |
| T2 | MART-$1_{(27-35)}$ | <10 | <10 | 944 | 1511 | 4760 | 11900 | 19 |
| T2 | MART-$1_{(32-40)}$ | <10 | <10 | <10 | <10 | <10 | <10 | <10 |
| T2 | MART-$1_{(26-35)}$ | <10 | <10 | 695 | 1150 | 4060 | 6710 | 23 |
| T2 | MART-$1_{(27-36)}$ | <10 | <10 | 11 | 84 | 469 | 614 | 19 |
| T2 | gp100$_{(457-465)}$ | <10 | <10 | <10 | <10 | <10 | 27 | 240 |

The ability of peptide-pulsed T2 cells to stimulate IL-2 release from non transfected (JRT NEO), bulk TCR clones-transfected (JRT BULK), and clone 5 TCR and clonal transfectant was assessed by ELISA. Prior to the assay T2 cells were incubated for 2 hr with MART-1 peptides (MART-$1_{(22-30)}$, MART-$1_{(27-35)}$, MART-$1_{(32-40)}$, MART-$1_{(26-35)}$, or MART-$1_{(27-36)}$) or gp100 peptide (gp100$_{(457-465)}$) at a concentration of 2.5 uM. As positive controls, HLA-A2 restricted TIL 1235 and TIL 1200 which recognize MART-1 epitopes MART-$1_{(27-35)}$, MART-$1_{(26-35)}$, MART-$1_{(27-36)}$ or gp100 epitope gp100$_{(457-465)}$ respectively were assayed for GM-CSF release.
[a]IL-2 released (pg/ml)
[b]GM-CSF released (pg/ml)

TABLE 7

CLONE 5 JURKAT TCR RECOGNITION OF TUMOR

| | | | Responder Cells | | | | |
|---|---|---|---|---|---|---|---|
| Stimulator Cell Line | Peptide (2.5 umol) | HLA A2.1 | None[a] | Jurkat neo[a] | Jurkat bulk[a] | Clone 22[a] | TIL 1235[b] |
| None | None | N/A | <10 | <10 | 23 | 49 | <10 |
| None | MART-$1_{(27-35)}$ | N/A | <10 | <10 | <10 | 66 | <10 |
| T2 | None | + | <10 | 31 | <10 | 49 | 66 |
| T2 | MART-$1_{(27-35)}$ | + | <10 | 17 | 1997 | 13502 | 1497 |
| 397 | None | − | 12 | 21 | <10 | 48 | <10 |
| 888 | None | − | 16 | <10 | <10 | <10 | <10 |
| 624− | None | − | <10 | <10 | <10 | 41 | <10 |
| 624+ | None | + | <10 | <10 | 13 | 62 | 557 |

TABLE 7-continued

CLONE 5JURKAT TCR RECOGNITION OF TUMOR

| | | | Responder Cells | | | | |
|---|---|---|---|---|---|---|---|
| Stimulator Cell Line | Peptide (2.5 umol) | HLA A2.1 | None[a] | Jurkat neo[a] | Jurkat bulk[a] | Clone 22[a] | TIL 1235[b] |
| 501 | None | + | 13 | <10 | <10 | 61 | 486 |
| 397 | MART-1$_{(27-35)}$ | − | <10 | <10 | <10 | 99 | <10 |
| 888 | MART-1$_{(27-35)}$ | − | 20 | <10 | <10 | 75 | 35 |
| 624− | MART-1$_{(27-35)}$ | − | <10 | <10 | <10 | 14 | 24 |
| 624+ | MART-1$_{(27-35)}$ | + | <10 | <10 | <10 | 428 | 448 |
| 501 | MART-1$_{(27-35)}$ | + | <10 | <10 | <10 | 540 | 635 |

The ability of peptide-pulsed T2 cells to mediate cytokine release from nontransfected release from non-transfected (JRT NEO), bulk TCR clones-transfected (JRT BULK) and clone 5 transfectant TCR + clonal (clone 13 and cline 22) Jurkat cells was assessed by ELISA. Prior to the assay T2 or tumor cells were incubated for 2 hr with MART-1$_{(27-35)}$ peptide at a concentration of 2.5 uM. As a positive control, HLA-A2 restricted TIL 1235 which recognizes MART-1$_{(27-35)}$ was assayed by GM-CSF release.
[a]IL-2 released (pg/ml)
[b]GM-CSF released (pg/ml)

EXAMPLE 4

Figure 5A:
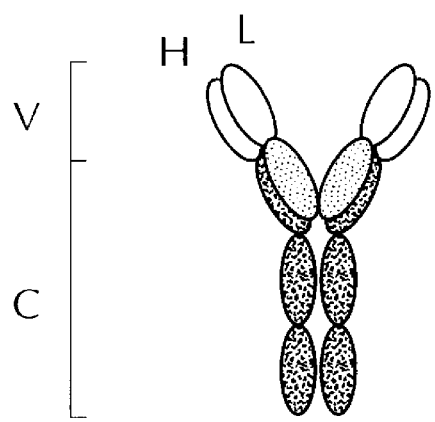
FIG. 5 shows the chimeric antibody/T-cell receptor which allows TCR signal transduction via antibody-antigen recognition. Single-chain antibody variable regions (scFv) are joined to TCR signaling chains, such as the γ chain of the Fc receptor, which shares homology with the TCR-ζ chain and is capable of mediating TCR signal transduction (Orloff, D., et al. *Nature*, 347:189–191, 1990, Letourneur, F. and Klausner, R. D. *Proc Natl Acad Sci* USA, 88:8905–8909, 1991, Romeo, C., et al. *Cell*, 68:889–897, 1992, Romeo, C. and Seed, B. *Cell*, 64:1037–1046, 1991, Irving, B. A. and Weiss, A. *Cell*, 64:891–901, 1991).
Figure 5C:
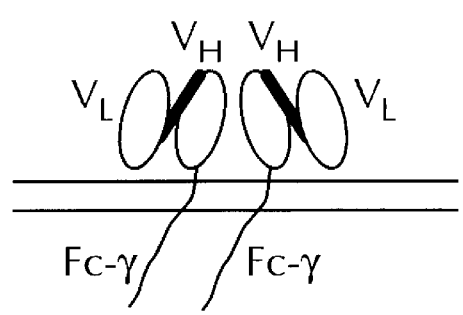
Figure 5B:
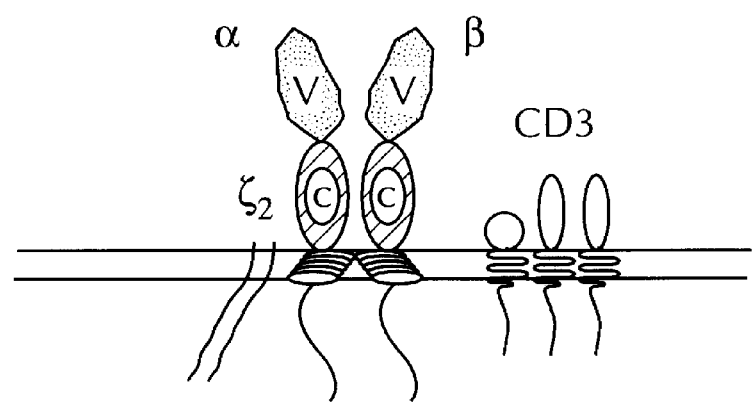

In Vivo Anti-Tumor Activity Of T-cells Redirected With Chimeric Antibody/T-cell Receptor Genes Materials and Methods Construction of chimeric receptor genes. Chimeric receptor genes composed of single chain variable regions (scFv) from monoclonal antibodies (MoAb) joined to the Fc receptor γ chain, which is capable of mediating T-cell receptor signal transduction (Orloff, D., et al. *Nature,* 347:189–191, 1990., Letourneur, F. and Klausner, R. D. *Proc Natl Acad Sci USA,* 88:8905–8909, 1991, Romeo, C., et al. *Cell,* 68:889–897, 1992, Romeo, C. and Seed, B. *Cell,* 64:1037–1046, 1991, Irving, B. A. and Weiss, A. *Cell,* 64:891–901, 1991), were constructed as previously described (FIG. 5; PCT WO93/19163 Hwu, P., et al. J Exp Med, 178:361–366, 1993, Eshhar, Z., et al. Proc Natl Acad Sci USA, 90:720–724, 1993). Chimeric receptors derived from MOv18 (Coney, L. R., et al. *Cancer Res,* 51:6125–6132, 1991, Miotti, S., et al. *Int J Cancer,* 39:297–303, 1987), a MoAb which binds a 38 kD folate binding protein (FBP) highly expressed on most ovarian adenocarcinomas and Sp6 (Kohler, G. and Milstein, C., et al. *Eur J Immunol,* 6:511–519, 1976, Ochi, A., Hawley, R. G., et al. *Proc Natl Acad Sci* USA, 80:6351–6355, 1983), an anti-2,4,6 TNP MoAb were engineered as described (PCT WO93/19163, Hwu, P., et al. *J Exp Med,* 178:361–366, 1993.) (MOv-γ and Sp-γ receptors, respectively).

Retroviral vectors. The MOv-γ or Sp-γ chimeric receptor genes were cloned into the LXSN or GLEN (Hwu, P., et al. *J Exp Med,* 178:361–366, 1993., Miller, A. D. and Rosman, G. J. *BioTechniques,* 7:980–988, 1989) Treisman, et al. *Blood* (1994) retroviral backbones under the transcriptional control of the LTR from Moloney murine leukemia virus. The retroviral constructs also contained the neomycin phosphotransferase gene (Neo[R]) as a selectable marker.

The gene encoding folate binding protein (FBP) was obtained from L. Coney (Apollon, Malvern, Pa.) and cloned into the LXSN retroviral backbone. The retroviral constructs were then transfected using CaPO4 into the PA317 amphotropic packaging cell line as previously described (Hwu, P., et al. *J Exp Med,* 178:361–366, 1993., Miller, A. D. and Buttimore, C. *Mol Cell Biol,* 6:2895–2902, 1986).

Tumor transduction and cell culture. Tumor cell lines were cultured in RPMI 1640 with 10% heat-inactivated FCS and glutamine (all from Biofluids, Rockville, Md.). 24JK tumor cells, a clone from the 3-methylcholanthrene-induced poorly immunogenic MCA 102 murine sarcoma (Shiloni, E., et al. Cancer Immunol Immunother, 37:286–292, 1993, Karp, S. E., et al. J Immunol, 150:896–908, 1993), were transduced with the FBP gene by incubation in retroviral supernatant in the presence of 8 μg/ml polybrene (Aldrich Chemical Co., Milwaukee, Wis.) to yield the 24JK-FBP tumor line. Media was replaced with fresh retroviral supernatant and polybrene every 12 hours for 3 days. Seventy-two hours after the final supernatant change, tumor cells were selected in 400 μg/ml of the neomycin analog G418 (Gibco, Grand Island, N.Y.). Following G418 selection, successful transduction was demonstrated by FACS analysis of tumor cells with MOv18 MoAb.

Lymphocyte transduction and cell culture. Murine TIL, derived from the diphenylhydrazine-induced MC38 murine colon adenocarcinoma, were grown in IL-2 as described (Yang, J. C., et al. *J. Biol. Resp. Modif.,* 9:149–159, 1990). For retroviral transduction with MOv-γ and Sp-γ chimeric receptor genes, (to generate MOv-TIL and TNP-TIL, respectively) antigen-stimulated TIL were pelleted and resuspended at 3×10⁵ TIL/ml in retroviral supernatant containing 30 IU/ml human recombinant IL-2 and 20 μg/ml protamine sulfate (Eli Lilly & Co., Indianapolis, Ind.). Media was partially exchanged with fresh retroviral supernatant containing IL-2 and protamine sulfate every 12 hours for 1–2 additional exposures. Forty-eight hours following the final supernatant change, TIL were selected in 0.3 mg/ml G418 for 5 days. This was followed by one week of expansion without G418, and then another 5-day selection in 0.3 to 1 mg/ml G418. Following G418 selection, successful transduction was confirmed by Northern analysis of total RNA as described (Hwu, P., et al. *J Immunol,* 150:4104–4115, 1993).

mIFN γ ELISA. 5×10⁵ TIL and 5×10⁵ stimulator cells were cocultured for 24 hours at 37° C. in a final volume of 1 ml RPMI with 10% FCS and 30 IU/ml of IL-2. Supernatants were then aspirated, centrifuged at 2000 rpm to remove cells, decanted and frozen at −70° C. Thawed aliquots were tested by ELISA for murine IFN γ. The ELISA employed a solid phase rat IgG$_{2A}$ MoAb specific for murine IFN-γ (Life Technologies, Gaithersburg, Md.). After addition of either sample or recombinant IFN-γ standard, a biotinylated rat IgG$_1$ MoAb specific for IFN-γ (PharMingen, San Diego, Calif.) was used, followed by avidin-peroxidase. Color reaction was performed with the addition of $H_2O_2$ and ABTS substrate (2,2'-Azino-bis[3-ethylbenzthiazoline-6-sulfonic acid]; Sigma Chemical Co., St. Louis, Mo.). The plates were then read at an OD of 405 nm.

Mice. C57BL/6 mice were obtained from Charles River (Raleigh, N.C.) and the Frederick Cancer Research Facility (Frederick, Md.) and used at 8–16 weeks of age. Athymic nude mice were obtained from the Frederick Cancer Research Facility, maintained in laminar flow housing and used at 6 to 12 weeks of age.

Pulmonary Metastasis Tumor Therapy Model. C57BL/6 mice received 500 cGy total-body irradiation (to minimize any host anti-tumor immune response), followed by IV injection of $5 \times 10^5$ to $1 \times 10^6$ 24JK or 24JK-FBP tumor cells. On day 3, mice were treated intravenously with $2-3 \times 10^7$ transduced or nontransduced TIL cells derived from the MC38 tumor, followed by 30,000 to 60,000 IU IL-2 i.p. three times a day for nine doses. Eleven to 16 days following initial tumor injection, mice were ear tagged and randomized and the lungs were removed; the number of pulmonary metastases was evaluated in a coded, blinded fashion as described previously (Mule, J. J., et al. *Science*, 225:1487–1489, 1984). Lungs with >250 metastases were scored as $\leq 250$ because this was the largest number that could be accurately counted. Numbers presented are the mean numbers of pulmonary metastases plus or minus the standard error. The significance of differences between groups was determined with the Wilcoxin Rank Sums test. All p values are two-tailed.

Intraperitoneal tumor therapy model. IGROV-1 human ovarian cancer cells (Alberti, S., et al. *Biochem Biophys Res Commun*, 171:1051–1055, 1990, Bénard, J., et al. *Cancer Res*, 45:4970–4979, 1985) were adapted in vivo by serial intraperitoneal passages in nude mice until the line consistently grew as ascites. For the intraperitoneal tumor model, $2.5 \times 10^6$ IGROV-1 fresh ascites cells were washed and injected intraperitoneally into nude mice. Three days later, the peritoneal tumor burden was evaluated in sample mice and the remainder were treated with a single intraperitoneal injection of $1-3 \times 10^7$ nontransduced or transduced MC38 TIL cells. Mice were then ear-tagged and randomized to avoid cage-effects, and followed for survival.

Gene transfer of FBP antigen into nonimmunogenic murine sarcoma. The nonimmunogenic murine fibrosarcoma 24JK was retrovirally transduced with the gene encoding folate binding protein (FBP), the antigen recognized by MOv18. Following selection with the neomycin analog G418, FBP-transduced 24JK tumor (24JK-FBP) displayed high levels of FBP as did the human ovarian carcinoma IGROV-1 as measured by FACS analysis with MOv18 (FIG. 6).

In vitro function of murine TIL transduced with chimeric receptor genes. Murine TIL derived from the MC38 colon adenocarcinoma (38 TIL) were transduced with chimeric receptor genes derived from either the anti-ovarian cancer MoAb MOv18 (MOv-γ) or the anti-TNP MoAb Sp6 (Sp-γ) (Hwu, P., et al. *J Exp Med*, 178:361–366, 1993;), and selected in G418. To assess in vitro activity, transduced, G418-selected TIL were co-cultured with tumor lines for 16–24 hours. Supernatants were then harvested and analyzed for mIFN-γ by ELISA. All TIL cultures produced large amounts of mIFN-γ when co-cultured with MC38 tumor cells (their native antigen) or in anti-CD3 coated plates. When co-cultured with IGROV-1 or 24JK-FBP tumor cells, both expressing large amounts of folate binding protein, mIFN-γ production by MOv-γ transduced TIL (MOv-TIL) increased by 54-fold and 14-fold, respectively, compared to MOv-TIL alone. In contrast, mIFN-γ production by non-transduced (NV) TIL and TIL transduced with the anti-TNP Sp-γ receptor (TNP-TIL) increased by only 2–4 fold upon co-culture with the FBP-expressing cell lines, and was not different compared to co-culture with the FBP non-expressing cell lines. None of the TIL cultures produced substantial amounts of mIFN-γ upon co-culture with non-transduced 24JK cells or 888 human melanoma cells (Table 8). These data indicate that the MOv-γ receptor gene can confer to murine TIL the capability to specifically recognize FBP-expressing tumor cells.

Figure 7:
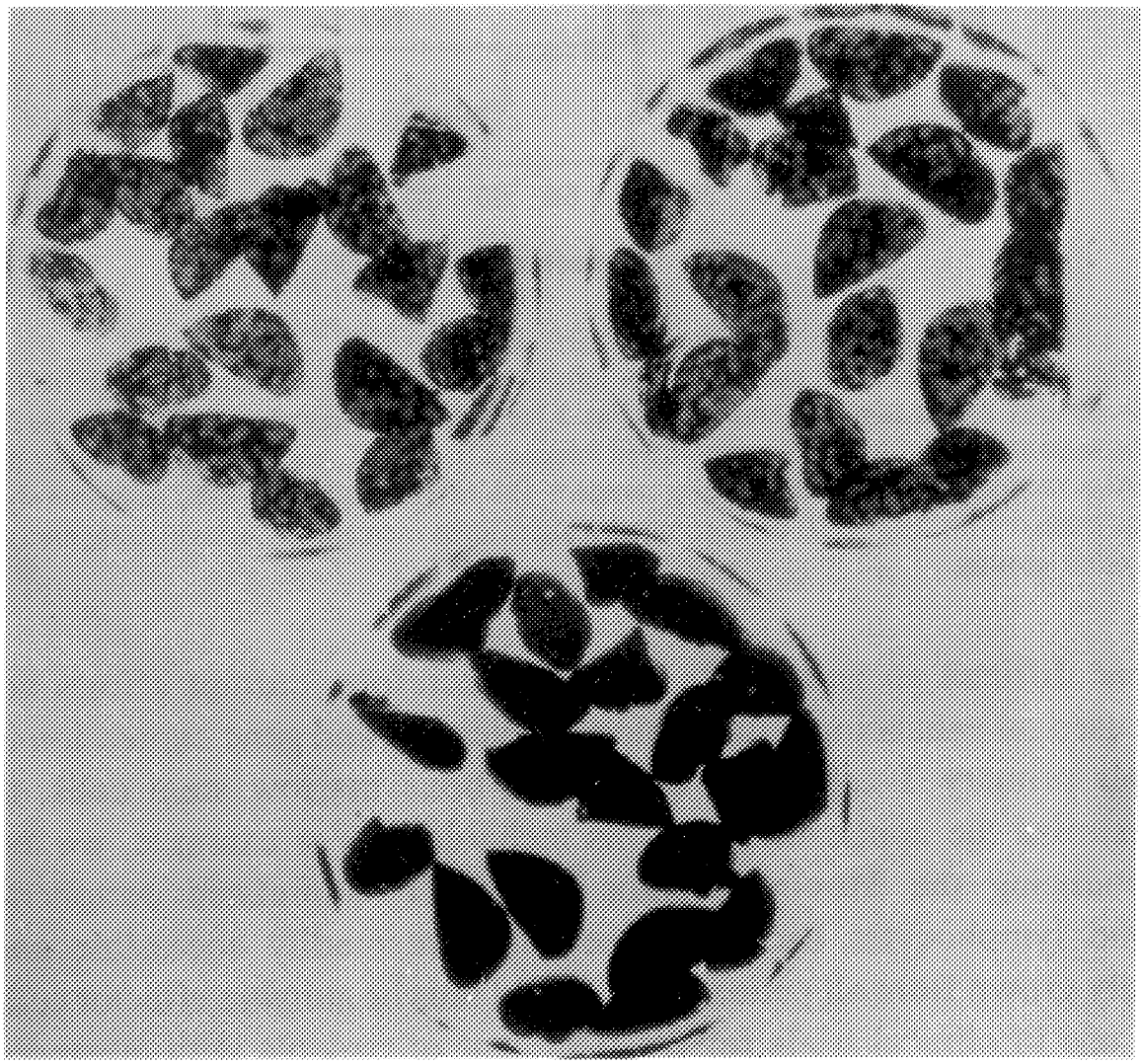
FIG. 7 shows appearance of lungs at 11 days after injection of 24JK-FBP cells. On day 3 after tumor injection, mice began therapy with either IL-2 (upper left), unmodified TIL+IL-2 (upper right), or MOv-γ transduced TIL+IL-2 (lower) as described in Materials and Methods of Example 4. Lungs were harvested after injection of india ink into trachea. Lungs were bleached with Fekete's solution to produce white metastases on a black background. A substantial reduction in metastases was seen in mice receiving MOv-γ transduced TIL+IL-2, compared to the other groups.

Treatment of Pulmonary Metastases. To determine whether MOv-TIL had antitumor activity in viva, C57BL/6 mice were injected via the tail vein with $1 \times 10^6$ 24JK tumor cells that were either non-transduced or transduced with the FBP gene. Three days later, mice were treated with $2.7 \times 10^7$ TIL, followed by 60,000 IU IL-2 every 8 hours for 9 doses. Eleven days following the initial injection of tumor cells, mice were sacrificed and lung metastases were counted. Only treatment with MOv-TIL in combination with IL-2 resulted in a significant reduction in lung metastases ($P_2<0.0004$ compared to all other treatment groups), whereas treatment with IL-2 alone or nontransduced (NV) TIL in combination with IL-2 did not significantly reduce the number of 24JK-FBP pulmonary metastases. MOv-TIL did not reduce the number of non-transduced 24JK tumor cells (Table 9 and FIG. 7), thus demonstrating their specificity for FBP-expressing tumors. These findings were corroborated in 2 replicate experiments.

Figure 8:
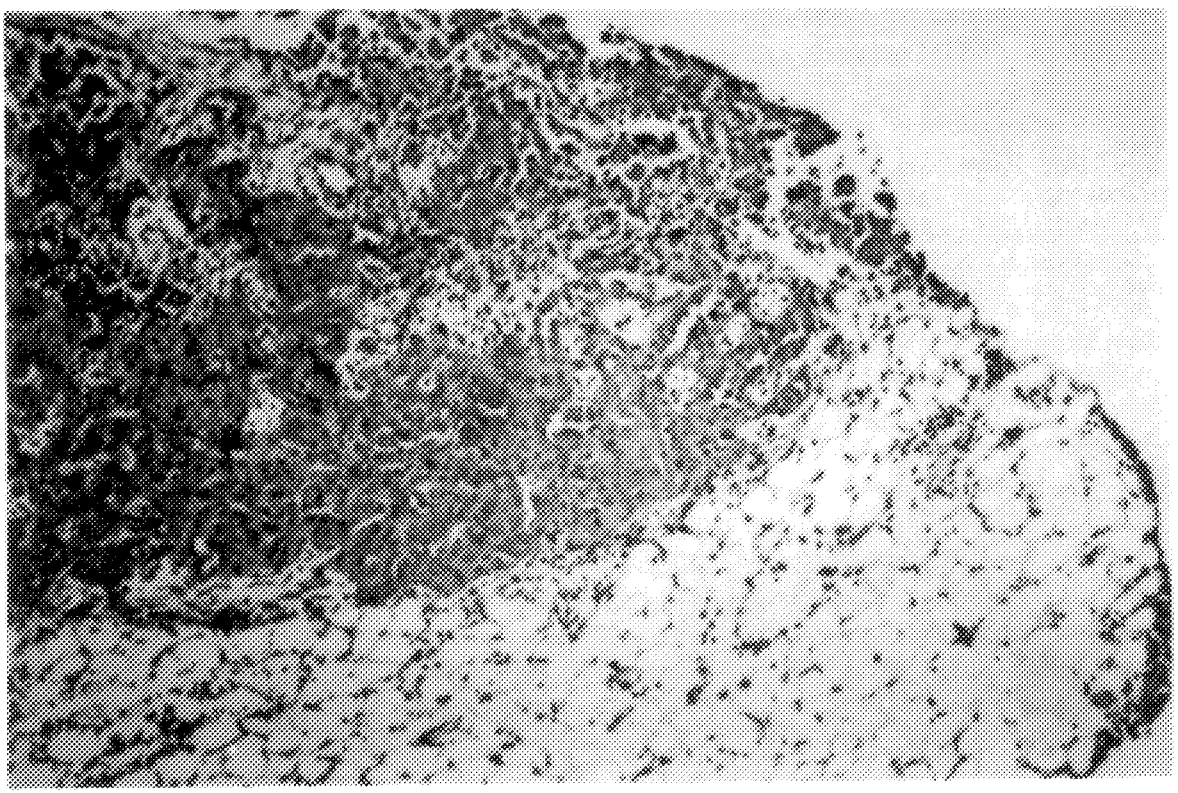
FIG. 8 shows histopathologic evaluation of peritoneal cavity 3 days following intraperitoneal injection of $2.5\times10^6$ human ovarian cancer IGROV cells into nude mice. Ovarian cancer cells can be seen invading the murine omentum.
Figure 9:
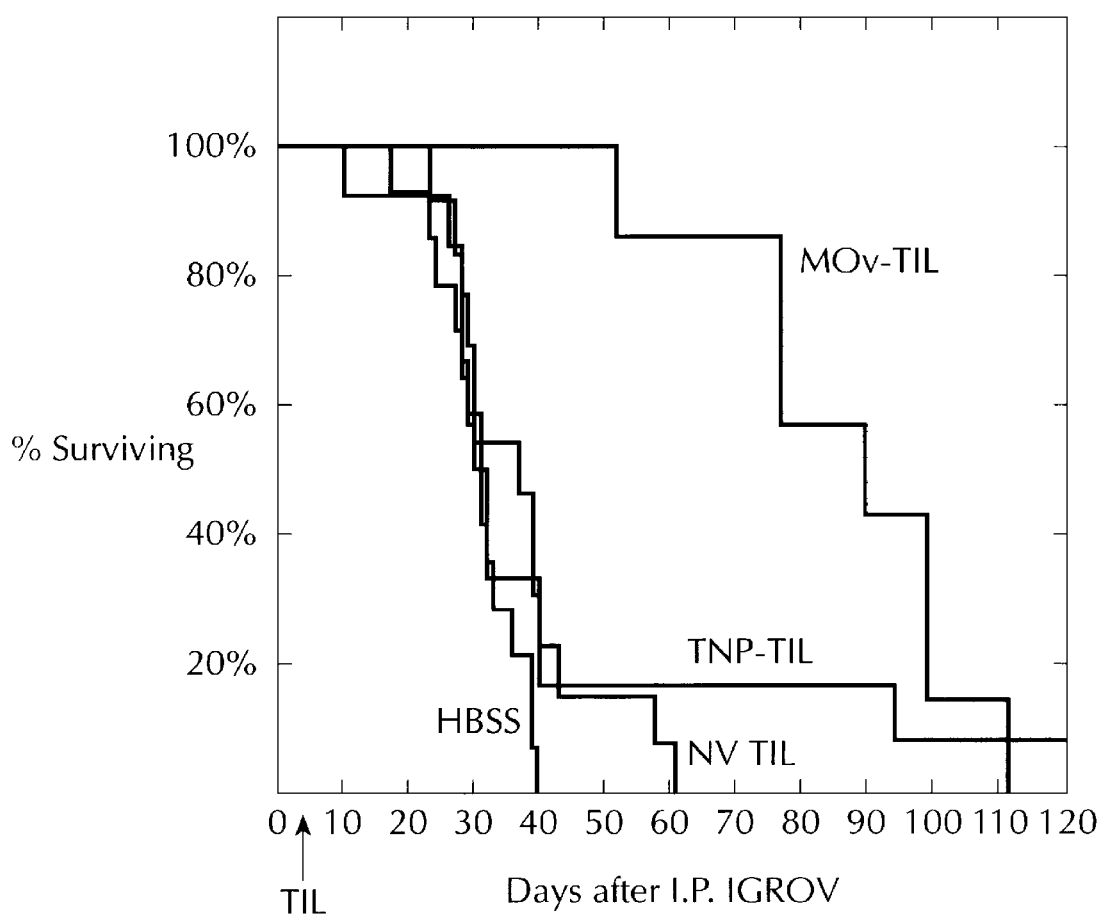
FIG. 9 shows survival of nude mice following intraperitoneal injection with human ovarian cancer (IGROV) cells. On day 3 following tumor injection (see FIG. 8, for histopathologic evaluation on day 3), mice were treated with HBSS, unmodified (NV) murine TIL, or TIL transduced with either the MOv-γ receptor or the control Sp-γ receptor (MOv-TIL and TNP-TIL, respectively). Mice treated with MOv-TIL demonstrated a significant increase in survival compared to the other groups.

Treatment of human ovarian cancer cells in nude mice. To assess whether MOv-TIL had significant in vivo activity against human ovarian carcinoma cells, nude mice were intraperitoneally implanted with $2.5 \times 10^6$ IGROV-1 cells from fresh ascites. Three days later, mice were treated with a single i.p. injection of TIL and then followed for survival. Histopathologic evaluation of sample mice at the time of treatment revealed that significant amounts of disease were present and invading structures within the murine peritoneal cavity 3 days after tumor injection (FIG. 8). Mice treated with MOv-TIL had significantly increased survival (median survival=90 days, $p_2<0.002$) compared to mice treated with saline only, nontransduced TIL or TNP-TIL (median survivals=31, 37, 31 days respectively; FIG. 9). This study was repeated with similar results.

Specific patterns of cytokine production by T-cells, such as TH1 versus TH2 cells, have been shown to dictate different immunologic responses and therapeutic outcomes (Romani, L., et al. *Infect. Immun.*, 59:4647–4654, 1991, Del Prete, G. and Romagnani, S. *Trends. Microbiol.*, 2:4–6, 1994, Reiner, S. L., et al. *Science*, 259:1457–1460, 1993, Locksley, R. M. and Scott, P. *Immunol Today*, 12:A58–61, 1991, Street, N. E. and Mosmann, T. R. *FASEB J.*, 5:171–177, 1991).

This study demonstrated that T-cells transduced with chimeric receptor genes are active in vivo against tumor cells bearing the receptor-defined antigen. Previous studies using nontransduced murine and human TIL (Barth, R., et al. *J Exp Med*, 173:647–658, 1991, Schwartzentruber, D. J., et al. *J Clin Oncol*, 12:1475–1483, 1994) have correlated specific cytokine production in vitro with function in vivo against tumor cells bearing native tumor-associated antigens. The present results, using T-cells expressing chimeric receptors, also demonstrate that T-cells that are therapeutically effective in vivo specifically secrete cytokines in vitro.

Because antibody-based recognition of tumor is dependent upon expression of tumor-associated antigens, one potential escape mechanism for tumor cells is the down-regulation of antigen expression. In the present study, intraperitoneal injection of IGROV tumor cells into nude mice followed by intraperitoneal therapy with MOv-TIL resulted in a significant increase in survival. Although survival was enhanced 3-fold, all mice eventually died from tumor ascites. FACS analysis of these tumor cells showed continued presence of FBP expression, unchanged from ascites in control mice. This suggests that antigen down-regulation was not the mechanism of escape in this particular model.

An intraperitoneal tumor model is particularly appropriate for ovarian cancer, since the most common and earliest mode of dissemination of this disease in cancer patients is by exfoliation of cells that implant along the surfaces of the peritoneal cavity (Berek, J. S. *Epithelial Ovarian Cancer.* In: J. S. Berek and N. F. Hacker (eds.), Practical Gynecologic Oncology, pp. 327–375, Baltimore: Williams and Wilkins. 1994).

TABLE 8

Interferon-γ release by MOv-γ transduced TIL[1]

Stimulator
[pg mIFN-γ/ml/5 × $10^5$ cells/16 hours]

| Responder | None | 38 Tumor | 24 JK | 24 JK FBP | IGROV | 888 MEL | 2C11[2] |
|---|---|---|---|---|---|---|---|
| None | 173 | 261 | 477 | 189 | 261 | 414 | 1483 |
| 38 TIL NV | 453 | 47,500 | 1220 | 1708 | 1642 | 688 | >50,000 |
| 38 TNP-TIL | 387 | 34,315 | 946 | 1045 | 1006 | 721 | >50,000 |
| 38 MOv-TIL | 299 | 41,195 | 891 | 4324 | 15,999 | 612 | >50,000 |

[1]In each ml, 5 × $10^5$ TIL were cocultured for 16 hrs at 37° C. with nothing, or 5 × $10^5$ target cells (eg, IGROV, 888 MEL), or 2C11 (anti-CD3) antibody.
[2]2C11 used at 4 μg/ml, coated with HCO3— buffer, O.N. at 4° C.

TABLE 9

Treatment of Pulmonary Metastases with MOv-TIL

| Tumor | Treatment | n | mean # lung metastases/mouse[3] | SEM |
|---|---|---|---|---|
| 24JK-FBP | HBSS | 8 | 229 | 18.6 |
|  | IL-2[1] | 10 | 232 | 11.0 |
|  | Normal TIL[2] + IL-2 | 10 | 195 | 16.3 |
|  | MOvTIL[2] + IL-2 | 7 | 13[4] | 3.0 |
| 24JK | HBSS | 5 | 240 | 9.6 |
|  | IL-2[1] | 9 | 221 | 11.0 |
|  | MOv TIL[2] + IL-2 | 5 | 223 | 7.6 |

[1]IL-2 was given beginning on day 3 after tumor injection at 60,000 IU ip three times a day for nine doses.
[2]2.7 × $10^7$ TIL (either unmodified or transduced with the MOv-γ chimeric receptor) were given once on Day 3 after tumor injection and followed by systemic IL-2 given as described above.
[3]Mice were sacrificed on Day 11 after tumor injection and lung metastases were counted in a blinded fashion. Metastases which were too numerous to count are arbitrarily designated as ≧250.
[4]Significantly less compared to other groups, $p_2 < 0.0004$.

EXAMPLE 5

Transduction of Stem Cells with Chimeric T-cell Receptor Genes

In order to combine the effector function of T-cells with the anti-tumor specificity of antibodies, chimeric receptor gene constructs containing the variable region domains from monoclonal antibodies (mAb) linked to the Fc receptor-associated γ chain, which has been shown to be capable of mediating signal transduction in T-cells were constructed. Chimeric receptor genes were made using single-chain VL/VH domains (scFv) from an anti-trinitrophenyl mAb as well as from MOv18, a mAb which binds the 38 kD folate binding protein highly expressed on most ovarian adenocarcinomas.

T-cells transduced with these chimeric receptor genes can specifically lyse and secrete cytokine in response to the antibody-defined antigen (Hwu, P., *J Exp Med.* 178:361–366, 1993). MOv-γ transduced T-lympnocytos lysed human ovarian cells and released GM-CSF upon co-culture with the ovarian cells. These Chimeric T-cell receptors have also been shown to be functional against tumors in vivo (Example 4).

The use of these chimeric antibody/T-cell receptor genes in hematopoietic stem cells is demonstrated here. Transduction of hematopoietic stem cells with chimeric receptor genes or antigen specific T-cell receptors allows for a permanent, regenerating in vivo supply of immune cells expressing the anti-tumor receptors, the generation of a wide variety of gene-modified cells (i.e. T-cells, macrophages, NK cells, and neutrophils.) and improved trafficking to tumor sites by transduced stem cells which differentiate and expand naturally in vivo. Tumor specific T-cell receptors may also be used in these methods.

Materials and Methods

Bone marrow transduction was performed as described (Bodine, D. M., *Proc Natl Acad Sci* USA 86:8897–8901, 1989). Briefly, donor mice were injected with 5FU to increase the percentage of stem cell recovery. Forty-eight hours later, mice were sacrificed and bone marrow cells (BMC) were harvested from the femur and tibia. The BMC were then cultured for 48 hours in 200 Units/ml of IL1, IL3, IL6 and 10% Wehi supernatant. The BMC were then cocultured on irradiated, chimeric receptor retroviral producer cells for 48 hours. Nonadherent BMC were then isolated and injected intravenously into recipient mice which were lethally irradiated with 950 rad prior to injection.

Other methods of bone marrow isolation and transduction with chimeric receptors may be used, including but not limited to, the use of more purified stem cell preparations, supernatant transductions, or support of stem cells using other growth factors and cytokines.

Murine hematopoietic tissues were analyzed at several times points for several months following the reconstitution. Fresh splenocytes from reconstituted mice were co-cultured with tumor cells, and supernatants were assayed for murine IFN-γ. In addition, splenocytes were activated with Con A, and assayed for cytokine release in a similar fashion 10 days later.

Figure 10A:
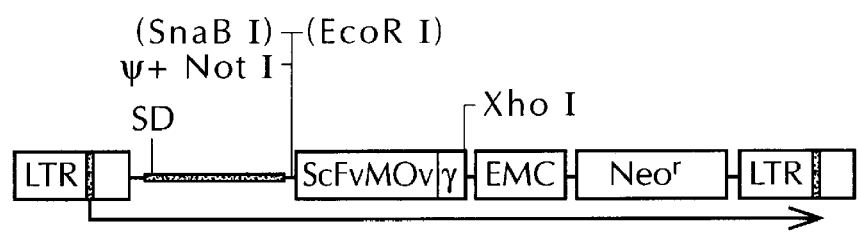
FIG. 10 shows retroviral constructs LMovγEN and LPMovγ containing receptor genes, used to transduce hematopoietic stem cells.
Figure 10B:
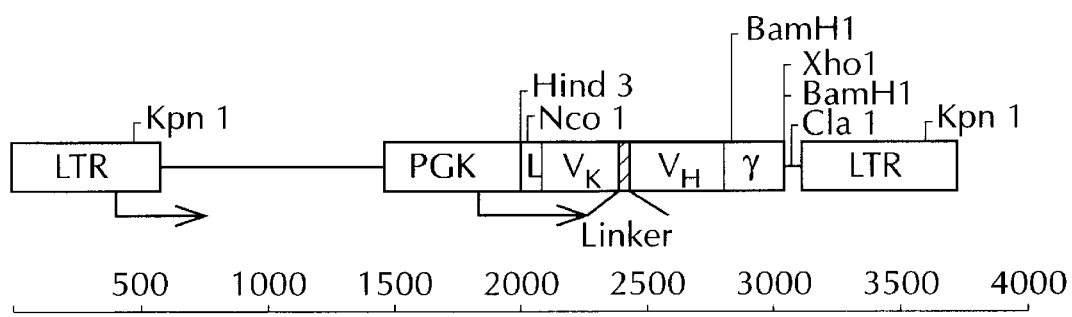

Vectors used: Two retroviral vectors expressing chimeric receptor genes have been utilized (FIG. 10). In one, the chimeric receptor gene is under the transcriptional control of the MMLV LTR. In the other vector, the pgk housekeeping gene promoter was used to ensure in vivo expression. In the data presented, a chimeric receptor gene (MOv-γ) derived from an anti-ovarian cancer monoclonal antibody was utilized, which binds to a folate binding protein (FBP) which is overexpressed on most ovarian adenocarcinomas. Chimeric receptors against other antigens may be used as well. In addition, other retroviral vector systems, AAV vectors (Muzyczka, N. *Curr. Top. Microbiol. Immunol*, 158:97–129, 1992), gene particle bombardment, or a variety of other gene transduction systems may be used to insert the recombinant constructs into the cells.

Northern: Northern blot analysis of total RNA from splenocytes, bone marrow cells, and thymocytes of reconstituted mice showed that those cells were positive for expression of the chimeric receptor gene.

Cytokine release: Fresh splenocytes derived from 3 normal mice and 3 MOv-γ reconstituted mice were cocultured with murine tumor cells. Murine tumor cells used were 24 JK non immunogenic methyl cholanthrene (MCA) induced sarcoma cells transduced to express the costimulatory molecule B7-1, or the folate binding protein (FBP) recognized by MOv-18 or both the B7-1 and FBP proteins. Significant levels of murine IFN-γ were detected from MOv-γ splenocytes cocultured with 24JK B7-FBP cells (Table 10). Significant cytokine secretion by fresh Mov-γ splenocytes was not seen upon co-culture with 24 JK cells expressing the FBP protein alone. Therefore, both B7 and FBP expression may be necessary for stimulation of fresh splenocytes from MOv-γ reconstituted mice. ConA stimulation was done as a positive control.

Activated splenocytes (Table 11) from MOv-γ reconstituted mice were capable of producing murine IFN-γ in response to both 24JK FBP and 24JK B7-FBP cells. Thus, stimulation of activated splenocytes from MOv-γ reconstituted mice seems to be independent of B7 expression on the target cells.

Fresh splenocytes required the expression of both B7 and the specific antigen on tumor cells for stimulation, as measured by mIFN-γ release. Because tumor cells do not normally express B7 on their surface, further additions may be added for the chimeric receptor to function in naive splenocytes derived from transduced bone marrow cells. For example, because B7 works by stimulating the CD28 receptor on T-cells, a chimeric receptor that uses the scFv antibody region joined to the CD28 signaling chain may be used in conjunction with the other chimeric receptors. T-cells expressing both the scFv-γ and scFv-CD28 receptors would provide both TCR stimulation and costimulation signals upon antigen binding. Since activated splenocytes did not require B7 for stimulation an alternative approach in patients may include ex vivo activation of peripheral blood lymphocytes following bone marrow transplant with the transduced stem cells.

These studies show that hematopoietic bone marrow cells can be stably modified genetically with chimeric T-cell receptors, and that their progeny can be redirected against new antigens, defined by monoclonal antibodies. Examples of disease that may be treated by the immune cells derived from stem cells transduced with chimeric receptors include but are not limited to cancers, such as melanoma and ovarian cancer. Other diseases, including but not limited to, infectious diseases such as HIV, bacterial infections, or fungal infection may also be treated with the stem cells transduced with chimeric receptors or native T-cell receptors.

Alternatively, the antigen specific T-cell receptors of this invention, preferably the melanoma specific T-cell receptors may be introduced into the stem cells by retroviral transduction and used to treat mammals afflicted with a disease, therapeutically or prophylactically. Immunotherapy employing stem cells expressing antigen specific T-cell receptors against viral or bacterial antigens or parasites may also be used in the methods described herein.

TABLE 10

Fresh Splenocytes from pgk MOv-γ
Reconstituted Mice Release mIFN-γ upon Stimulation
with Tumors Expressing Both B7 and FBP Stimulator
[pg/1.5 × $10^6$ splenocytes/ml/48 hrs]

| Responder | None | 24JK NV | 24JK FBP | 24JK B7 | 24JK B7-FBP | ConA |
|---|---|---|---|---|---|---|
| None | 76 | 17 | 4 | 166 | 26 | 0 |
| NV-1 | 41 | 268 | 158 | 162 | 92 | 12,071 |
| NV-2 | 50 | 127 | 96 | 103 | 63 | 13,916 |
| NV-3 | 30 | 96 | 37 | 166 | 193 | 12,909 |
| MOv-γ 1 | 19 | 98 | 95 | 27 | 902 | 13,664 |
| MOv-γ 2 | 48 | 319 | 48 | 106 | 1078 | 11,584 |
| MOv-γ 3 | 76 | 188 | 65 | 157 | 1064 | 12,794 |

● 1.5 × $10^6$ splenocytes + 5 × $10^5$ tumor cells/ml cocultured for 48 hours.

TABLE 11

Activated Splenocytes from pgk MOv-γ
Reconstituted Mice Release mIFN-γ upon Stimulation
with FBP-Expressing Tumors Stimulator
[pg/1.5 × $10^6$ splenocytes/ml/18 hrs]

| Responder | None | 24JK NV | 24JK FBP | 24JK B7 | 24JK B7-FBP | ConA |
|---|---|---|---|---|---|---|
| None | 0 | 0 | 0 | 0 | 0 | 0 |
| NV-1 | 252 | 27 | 36 | 54 | 64 | 6376 |
| NV-2 | 108 | 68 | 67 | 58 | 85 | 1988 |
| NV-3 | 8 | 60 | 0 | 82 | 0 | 1388 |
| MOv-γ 1 | 64 | 101 | 1249 | 93 | 2289 | 2797 |
| MOv-γ 2 | 144 | 130 | 1377 | 234 | 1804 | 8541 |
| MOv-γ 3 | 143 | 127 | 2832 | 162 | 3741 | 9096 |

● 1.5 × $10^6$ splenocytes + 5 × $10^5$ tumor cells/ml cocultured for 18 hours.

EXAMPLE 6

Use Of Lymphocytes Expressing T-cell Receptors Which Recognize Melanoma Antigens For Therapeutically Treating Mammals Afflicted With Melanoma T-lymphocytes expressing the T-cell receptors provided herein to the melanoma antigen may be effective in therapeutically treating mammals afflicted with melanoma. A retroviral expression vector carrying both the α and β chain of the melanoma antigen specific T-cell receptors may be introduced into a retroviral packaging cell line. Alternatively, the alpha chain and beta chain may each be placed in a separate retroviral expression vector and introduced into the retroviral packaging cell line. By way of example T-lymphocytes are isolated from peripheral blood or melanoma tumor suspensions and cultured in vitro (Kawakami, Y. et al. (1988) *J. Exp. Med.* 168:2183–2191). The T-lymphocytes or TIL are resuspended in media and exposed to retroviral supernatants (Hwu et al. (1993) *J. of Immunol.* 150:4104–4115. Retroviral supernatants may be supplemented with protamine sulfate and IL-2. The T-lymphocytes expressing the T-cell receptor may then be transfused into the patient in need of such treatment. The lymphocytes may be administered either intravenously, intraperitoneally or intralesionally. This treatment may be administered concurrently with other therapeutic treatments such as cytokines, radiotherapy, surgical excision of melanoma lesions and chemotherapeutic drugs, active immunization, adoptive T lymphocyte therapy.

The present invention is not to be limited in scope by the nucleic acid sequences disclosed or deposited, since the deposited embodiment is intended as a single illustration of one aspect of the invention and any sequences which are functionally equivalent are within the scope of this invention. Indeed, various modifications of the invention in addition to those shown and described herein will become apparent to those skilled in the art from the foregoing description and accompanying drawings. Such modifications are intended to fall within the scope of the claims appended hereto.

We claim:

1. A composition comprising two isolated polynucleotides wherein the first polypeptide encodes an α chain and the second polynucleotide encodes a β chain of a T cell receptor wherein said first and second polynucleotides encode a T-cell receptor being selected from the group consisting of (a) Vα8.2/Jα49/Cα chain, having the V-J junctional sequences shown in FIG. 1A (SEQ ID NO.:1) and Vβ13.6/Dβ1.1/Jβ1.5/Cβ1 having the V-D-J junctional sequences shown in FIG. 1A (SEQ. ID. NO:3); (b) Vα 17/Jα42/Cα having the V-J junctional sequences shown in FIG. 1B (SEQ. ID. NO: 4) and Vβ6.5/Dβ0.1/Jβ0.5/Cβ having the V-D-J junctional sequences shown in FIG. 1B (SEQ. ID. NO:7); (c) Vα9/Jα16/Cα having the V-J junctional sequences shown in FIG. 1B (SEQ. ID. NO: 5) and Vβ22.1/Dβ2.1/Jβ2.1/Cβ2 having the V-D-J junctional sequences shown in FIG. 1B (SEQ. ID. NO:8); (d) Vα1/Jα49/Cα having the V-J junctional sequences shown in FIG. 1B (SEQ. ID. NO:6); and Vβ7.3/Dβ2.6/Jβ2.1/Cβ2 having the V-D-J junctional sequences shown in FIG. 1B (SEQ. ID. NO:9); (e) Vα25/Jα54/Cα having the V-J junctional sequences shown in FIG. 2 (SEQ. ID. NO: 10) and Vβ3.1/Dβ1.1/Jβ1.1/Cβ1 having the V-D-J junctional sequences shown in FIG. 2 (SEQ. ID. NO:12); (f) Vα21/Jα42/Cα having the V-J junctional sequences shown in FIG. 2 (SEQ. ID. NO:11) and Vβ7.3/Dβ2.1/Jβ2.7/Cβ2 having the V-D-J junctional sequences shown in FIG. 2 (SEQ. ID. NO:13); and (g) nucleic acid sequences encoding said T-cell receptor which retain the antigen recognition function of said T-cell receptor encoded by (a)–(f).

2. An expression vector comprising polynucleotide sequences encoding a T-cell receptor according to claim 1.

3. A cultured host cell containing an expression vector according to claim 2.

4. The host cell of claim 3 wherein said host cell is selected from the group consisting of T-lymphocytes, natural killer cells, monocytes, or mammalian hematopoietic stem cells.

5. A composition comprising the host cell of claim 3 and an effective carrier.

6. A composition comprising the expression vector of claim 2 and an effective carrier.

7. The composition according to claim 1 wherein said first polynucleotide encoding said α chain and said second polynucleotide encoding said β chain is Vα8.2/Jα49/Cα chain, having the V-J junctional sequences shown in FIG. 1A (SEQ ID NO:1) and Vβ13.6/Dβ1.1/Jβ1.5/Cβ1 having the V-D-J junctional sequences shown in FIG. 1A (SEQ ID NO:3).

8. The composition according to claim 1 wherein said first polynucleotide encoding said α chain and said second polynucleotide encoding said β chain is Vα17/Jα42/Cα having the V-J junctional sequences shown in FIG. 1B (SEQ ID NO:4) and Vβ6.5/Dβ0.1/Jβ0.5/Cβ having the V-D-J junctional sequences shown in FIG. 1B (SEQ ID NO:7).

9. The composition according to claim 1 wherein said first polynucleotide encoding said α chain and said second polynucleotide encoding said β chain is Vα9/Jα16/Cα having the V-J junctional sequences shown in FIG. 1B (SEQ ID NO:5) and Vβ22.1/Dβ2.1/Jβ2.1/Cβ2 having the V-D-J junctional sequences shown in FIG. 1B (SEQ ID NO:8).

10. The composition according to claim 1 wherein said first polynucleotide encoding said α chain and said second polynucleotide encoding said β chain is Vα1/Jα49/Cα having the V-J junctional sequences shown in FIG. 1B (SEQ ID NO:6); and Vβ7.3/Dβ2.6/Jβ2.1/Cβ2 having the V-D-J junctional sequences shown in FIG. 1B (SEQ ID NO:9).

11. The composition according to claim 1 wherein said first polynucleotide encoding said α chain and said second polynucleotide encoding said β chain is Vα25/Jα54/Cα having the V-J junctional sequences shown in FIG. 2 (SEQ ID NO:10) and Vβ3.1/Dβ1.1/Jβ1.1/Cβ1 having the V-D-J junctional sequences shown in FIG. 2 (SEQ ID NO:12).

12. The composition according to claim 1 wherein said first polynucleotide encoding said α chain and said second polynucleotide encoding said β chain is Vα21/Jα42/Cα having the V-J junctional sequences shown in FIG. 2 (SEQ. ID. NO:11) and Vβ7.3/Dβ2.1/Jβ2.7/Cβ2 having the V-D-J junctional sequences shown in FIG. 2 (SEQ. ID. NO.:13).

13. The composition according to claim 1, wherein the T-cell receptor recognizes a melanoma antigen.

14. The T-cell receptor of claim 13 wherein the melanoma antigen is a gp100 or MART-1 antigen.

15. The melanoma antigen of claim 14 wherein said melanoma antigen is MART-1.

16. The MART-1 antigen of claim 14 wherein said MART-1 antigen is AAGIGILTV (SEQ ID NO:28), EAAGIGILTV (SEQ ID NO:29), or AAGIGILTVI (SEQ ID NO:31).

* * * * *

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
        ( A ) LENGTH: 96
        ( B ) TYPE: NUCLEOTIDE
        ( C ) STRANDEDNESS: DOUBLE
        ( D ) TOPOLOGY: UNKNOWN ( x i ) SEQUENCE DESCRIPTION:SEQ ID NO:1:

```
TACTTTTGTG  CAGAGAATAT  GATGAACACC  GGTAACCAGT                         40

TCTATTTTGG  GACAGGGACA  AGTTTGACGG  TCATTCCAAA                         80

TATCCAGAAC  CCTGAC                                                     96
```

( 2 ) INFORMATION FOR SEQ ID NO:2:

( i ) SEQUENCE CHARACTERISTICS:
        ( A ) LENGTH:108
        ( B ) TYPE: NUCLEOTIDE
        ( C ) STRANDEDNESS: DOUBLE
        ( D ) TOPOLOGY: UNKNOWN ( x i ) SEQUENCE DESCRIPTION:SEQ ID NO:2:

```
ATGTATTTCT  GTGCTTATAG  GGGCCTTGGG  GTGGTGCTAC                         40

AAACAAGCTC  ATCTTTGGAA  CTGGCACTCT  GCTTGCTGTC                         80

CAGCCAAGTA  CATATCCAGA  ACCCTGAC                                      108
```

( 2 ) INFORMATION FOR SEQ ID NO:3:

( i ) SEQUENCE CHARACTERISTICS:
        ( A ) LENGTH: 105
        ( B ) TYPE: NUCLEOTIDE
        ( C ) STRANDEDNESS: DOUBLE
        ( D ) TOPOLOGY: UNKNOWN ( x i ) SEQUENCE DESCRIPTION:SEQ ID NO:3:

```
TACTTCTGTG  CCAGCCGACC  TACTATAACG  GTCCCGTATA                         40

GCAATCAGCC  CCAGCATTTT  GGTGATGGGA  CTCGACTCTC                         80

CATCCTAGAG  GACCTGAACA  AGGTG                                         105
```

( 2 ) INFORMATION FOR SEQ ID NO:4:

( i ) SEQUENCE CHARACTERISTICS:
        ( A ) LENGTH: 98
        ( B ) TYPE: NUCLEOTIDE
        ( C ) STRANDEDNESS: DOUBLE ( D ) TOPOLOGY: UNKNOWN ( x i ) SEQUENCE DESCRIPTION:SEQ ID NO:4:

| | | | | |
|---|---|---|---|---|
| ACCTACTTCT | GTGCAGCAAG | CAAGGGAGGA | AGCCAAGGAA | 40 |
| ATCTCATCTT | TGGAAAAGGC | ACTAAACTCT | CTGTAAACCA | 80 |
| AATATCCAGA | ACCCTGAC | | | 98 |

( 2 ) INFORMATION FOR SEQ ID NO:5:

( i ) SEQUENCE CHARACTERISTICS:
        ( A ) LENGTH: 93
        ( B ) TYPE: NUCLEOTIDE
        ( C ) STRANDEDNESS: DOUBLE
        ( D ) TOPOLOGY: UNKNOWN ( x i ) SEQUENCE DESCRIPTION:SEQ ID NO:5:

| | | | | |
|---|---|---|---|---|
| ATGTATTACT | GTGCTCTAAT | CCCAGGAGGC | CAGAAGCTGC | 40 |
| TCTTTGCAAG | GGGGACCATG | TTAAAGGTGG | ATCTTAATAT | 80 |
| CCAGAACCCT | GAC | | | 93 |

( 2 ) INFORMATION FOR SEQ ID NO:6:

( i ) SEQUENCE CHARACTERISTICS:
        ( A ) LENGTH: 93
        ( B ) TYPE: NUCLEOTIDE
        ( C ) STRANDEDNESS: DOUBLE
        ( D ) TOPOLOGY: UNKNOWN ( x i ) SEQUENCE DESCRIPTION:SEQ ID NO:6:

| | | | | |
|---|---|---|---|---|
| GAGTACTTCT | GTGCTGTGGG | TGCCACCGGT | AACCAGTTCT | 40 |
| ATTTTGGGAC | AGGGACAAGT | TTGACGGTCA | TTCCAAATAT | 80 |
| CCAGAACCCT | GAC | | | 93 |

( 2 ) INFORMATION FOR SEQ ID NO:7:

( i ) SEQUENCE CHARACTERISTICS:
        ( A ) LENGTH: 108
        ( B ) TYPE: NUCLEOTIDE
        ( C ) STRANDEDNESS: DOUBLE
        ( D ) TOPOLOGY: UNKNOWN ( x i ) SEQUENCE DESCRIPTION:SEQ ID NO:7:

| | | | | |
|---|---|---|---|---|
| ATGTATCTCT | GTGCCAGCAG | CTTAGTAGTC | TGGGACAGGG | 40 |
| GTGGTAATCA | GCCCCAGCAT | TTTGGTGATG | GGACTCGACT | 80 |
| CTCCATCCTA | GAGGACCTGA | ACAAGGTG | | 108 |

( 2 ) INFORMATION FOR SEQ ID NO:8:

( i ) SEQUENCE CHARACTERISTICS:
        ( A ) LENGTH: 102
        ( B ) TYPE: NUCLEOTIDE
        ( C ) STRANDEDNESS: DOUBLE
        ( D ) TOPOLOGY: UNKNOWN ( x i ) SEQUENCE DESCRIPTION:SEQ ID NO:8:

| | | | | |
|---|---|---|---|---|
| ATGTACTTCT | GTGCCGCTGG | GGAGACTAGC | GGGGTGTCGT | 40 |
| ACAATGAGCA | GTTCTTCGGG | CCAGGACAC | GGCTCACCGT | 80 |
| GCTAGAGGAC | CTGAAAAACG | TG | | 102 |

( 2 ) INFORMATION FOR SEQ ID NO:9:

( i ) SEQUENCE CHARACTERISTICS:
  ( A ) LENGTH: 99
  ( B ) TYPE: NUCLEOTIDE
  ( C ) STRANDEDNESS: DOUBLE
  ( D ) TOPOLOGY: UNKNOWN ( x i ) SEQUENCE DESCRIPTION:SEQ ID NO:9:

| | | | | |
|---|---|---|---|---|
| CTGTATCTCT | GTGCCAGCAG | CCAAGATCTC | CTGAGTTGGG | 40 |
| ATGAGCAGTT | CTTCGGGCCA | GGGACACGGC | TCACCGTGCT | 80 |
| AGAGGACCTG | AAAAACGTG | | | 99 |

( 2 ) INFORMATION FOR SEQ ID NO:10:

( i ) SEQUENCE CHARACTERISTICS:
    ( A ) LENGTH: 93
    ( B ) TYPE: NUCLEOTIDE
    ( C ) STRANDEDNESS: DOUBLE
    ( D ) TOPOLOGY: UNKNOWN ( x i ) SEQUENCE DESCRIPTION:SEQ ID NO:10:

| | | | | |
|---|---|---|---|---|
| ATCTACTTCT | GTGCTGGCCC | GGGTAGCAAC | TATAAACTGA | 40 |
| CATTTGGAAA | AGGAACTCTC | TTAACCGTGA | ATCCAAATAT | 80 |
| CCAGAACCCT | GAC | | | 93 |

( 2 ) INFORMATION FOR SEQ ID NO:11:

( i ) SEQUENCE CHARACTERISTICS:
    ( A ) LENGTH: 99
    ( B ) TYPE: NUCLEOTIDE
    ( C ) STRANDEDNESS: DOUBLE
    ( D ) TOPOLOGY: UNKNOWN ( x i ) SEQUENCE DESCRIPTION:SEQ ID NO:11:

| | | | | |
|---|---|---|---|---|
| GTGTACTTCT | GTGCCGCATA | TTATGGAGGA | AGCCAAGGAA | 40 |
| ATCTCATCTT | TGGAAAAGGC | ACTAAACTCT | CTGTTAAACC | 80 |
| AAATATCCAG | AACCCTGAC | | | 99 |

( 2 ) INFORMATION FOR SEQ ID NO:12:

( i ) SEQUENCE CHARACTERISTICS:
    ( A ) LENGTH: 96
    ( B ) TYPE: NUCLEOTIDE
    ( C ) STRANDEDNESS: DOUBLE
    ( D ) TOPOLOGY: UNKNOWN ( x i ) SEQUENCE DESCRIPTION:SEQ ID NO:12:

| | | | | |
|---|---|---|---|---|
| ATGTACCTCT | GTGCCAGCAG | TTTTGAAGGA | TTGGGCACTG | 40 |
| AAGCTTTCTT | TGGACAAGGC | ACCAGACTCA | CAGTTGTAGA | 80 |
| GGACCTGAAC | AAGGTG | | | 96 |

( 2 ) INFORMATION FOR SEQ ID NO:13:

( i ) SEQUENCE CHARACTERISTICS:
    ( A ) LENGTH: 99
    ( B ) TYPE: NUCLEOTIDE
    ( C ) STRANDEDNESS: DOUBLE
    ( D ) TOPOLOGY: UNKNOWN ( x i ) SEQUENCE DESCRIPTION:SEQ ID NO:13:

| | | | | |
|---|---|---|---|---|
| CTGTATCTCT | GTGCCAGCAG | CCAAGAGGGA | CTAGCGGGAG | 40 |
| CGTCGCAGTA | CTTCGGGCCG | GGCACCAGGC | TCACGGTCAC | 80 |

```
AGAGGACCTG AAAAACGTG                                                          99
```

( 2 ) INFORMATION FOR SEQ ID NO:14:

( i ) SEQUENCE CHARACTERISTICS:
        ( A ) LENGTH: 32
        ( B ) TYPE: AMINO ACID
        ( C ) STRANDEDNESS: UNKNOWN
        ( D ) TOPOLOGY: UNKNOWN ( x i ) SEQUENCE DESCRIPTION:SEQ ID NO:14:

```
Tyr  Phe  Cys  Ala  Glu  Asn  Met  Met  Asn  Thr  Gly  Asn
 1                  5                        10

Gln  Phe  Tyr  Phe  Gly  Thr  Gly  Thr  Ser  Leu  Thr  Val
              15                       20

Ile  Pro  Asn  Ile  Gln  Asn  Pro  Asp
 25                      30
```

( 2 ) INFORMATION FOR SEQ ID NO:15:

( i ) SEQUENCE CHARACTERISTICS:
        ( A ) LENGTH: 36
        ( B ) TYPE: AMINO ACID
        ( C ) STRANDEDNESS: UNKNOWN
        ( D ) TOPOLOGY: UNKNOWN ( x i ) SEQUENCE DESCRIPTION:SEQ ID NO:15:

```
Met  Tyr  Phe  Cys  Ala  Tyr  Arg  Gly  Leu  Gly  Val  Val
 1                  5                        10

Leu  Gln  Thr  Ser  Ser  Ser  Leu  Glu  Leu  Ala  Leu  Cys
              15                       20

Leu  Leu  Ser  Ser  Gln  Val  His  Ile  Gln  Asn  Pro  Asp
 25                      30                            35
```

( 2 ) INFORMATION FOR SEQ ID NO:16:

( i ) SEQUENCE CHARACTERISTICS:
        ( A ) LENGTH: 35
        ( B ) TYPE: AMINO ACID
        ( C ) STRANDEDNESS: UNKNOWN
        ( D ) TOPOLOGY: UNKNOWN ( x i ) SEQUENCE DESCRIPTION:SEQ ID NO:16:

```
Tyr  Phe  Cys  Ala  Ser  Arg  Pro  Thr  Ile  Thr  Val  Pro
 1                  5                        10

Tyr  Ser  Asn  Gln  Pro  Gln  His  Phe  Gly  Asp  Gly  Thr
              15                       20

Arg  Leu  Ser  Ile  Leu  Glu  Asp  Leu  Asn  Lys  Val
 25                      30                       35
```

( 2 ) INFORMATION FOR SEQ ID NO:17:

( i ) SEQUENCE CHARACTERISTICS:
        ( A ) LENGTH: 33
        ( B ) TYPE: AMINO ACID
        ( C ) STRANDEDNESS: UNKNOWN
        ( D ) TOPOLOGY: UNKNOWN ( x i ) SEQUENCE DESCRIPTION:SEQ ID NO:17:

```
Thr  Tyr  Phe  Cys  Ala  Ala  Ser  Lys  Gly  Gly  Ser  Gln
 1                  5                        10

Gly  Asn  Leu  Ile  Phe  Gly  Lys  Gly  Thr  Lys  Leu  Ser
              15                       20
```

Val Lys Pro Asn Ile Gln Asn Pro Asp
25                  30

( 2 ) INFORMATION FOR SEQ ID NO:18:

( i ) SEQUENCE CHARACTERISTICS:
        ( A ) LENGTH: 31
        ( B ) TYPE: AMINO ACID
        ( C ) STRANDEDNESS: UNKNOWN
        ( D ) TOPOLOGY: UNKNOWN ( x i ) SEQUENCE DESCRIPTION:SEQ ID NO:18:

Met Tyr Tyr Cys Ala Leu Ile Pro Gly Gly Gln Lys
1                5                    10

Leu Leu Phe Ala Arg Gly Thr Met Leu Lys Val Asp
             15                  20

Leu Asn Ile Gln Asn Pro Asp
25                  30

( 2 ) INFORMATION FOR SEQ ID NO:19:

( i ) SEQUENCE CHARACTERISTICS:
        ( A ) LENGTH: 31
        ( B ) TYPE: AMINO ACID
        ( C ) STRANDEDNESS: UNKNOWN
        ( D ) TOPOLOGY: UNKNOWN ( x i ) SEQUENCE DESCRIPTION:SEQ ID NO:19:

Glu Tyr Phe Cys Ala Val Gly Ala Thr Gly Asn Gln
1                5                    10

Phe Tyr Phe Gly Thr Gly Thr Ser Leu Thr Val Ile
             15                  20

Pro Asn Ile Gln Asn Pro Asp
25                  30

( 2 ) INFORMATION FOR SEQ ID NO:20:

( i ) SEQUENCE CHARACTERISTICS:
        ( A ) LENGTH: 36
        ( B ) TYPE: AMINO ACID
        ( C ) STRANDEDNESS: UNKNOWN
        ( D ) TOPOLOGY: UNKNOWN ( x i ) SEQUENCE DESCRIPTION:SEQ ID NO:20:

Met Tyr Leu Cys Ala Ser Ser Leu Val Val Trp Asp
1                5                    10

Arg Gly Gly Asn Gln Pro Gln His Phe Gly Asp Gly
             15                  20

Thr Arg Leu Ser Ile Leu Glu Asp Leu Asn Lys Val
25                  30                      35

( 2 ) INFORMATION FOR SEQ ID NO:21:

( i ) SEQUENCE CHARACTERISTICS:
        ( A ) LENGTH: 34
        ( B ) TYPE: AMINO ACID
        ( C ) STRANDEDNESS: UNKNOWN
        ( D ) TOPOLOGY: UNKNOWN ( x i ) SEQUENCE DESCRIPTION:SEQ ID NO:21:

Met Tyr Phe Cys Ala Ala Gly Glu Thr Ser Gly Val
1                5                    10

Ser Tyr Asn Glu Gln Phe Phe Gly Pro Gly Thr Arg
             15                  20

```
Leu Thr Val Leu Glu Asp Leu Lys Asn Val
 25                  30
```

( 2 ) INFORMATION FOR SEQ ID NO:22:

( i ) SEQUENCE CHARACTERISTICS:
        ( A ) LENGTH: 33
        ( B ) TYPE: AMINO ACID
        ( C ) STRANDEDNESS: UNKNOWN
        ( D ) TOPOLOGY: UNKNOWN ( x i ) SEQUENCE DESCRIPTION:SEQ ID NO:22:

```
Leu Tyr Leu Cys Ala Ser Ser Gln Asp Leu Leu Ser
 1               5                   10
Trp Asp Glu Gln Phe Phe Gly Pro Gly Thr Arg Leu
             15                  20
Thr Val Leu Glu Asp Leu Lys Asn Val
 25                  30
```

( 2 ) INFORMATION FOR SEQ ID NO:23:

( i ) SEQUENCE CHARACTERISTICS:
        ( A ) LENGTH: 31
        ( B ) TYPE: AMINO ACID
        ( C ) STRANDEDNESS: UNKNOWN
        ( D ) TOPOLOGY: UNKNOWN ( x i ) SEQUENCE DESCRIPTION:SEQ ID NO:23:

```
Ile Tyr Phe Cys Ala Gly Pro Gly Ser Asn Tyr Lys
 1               5                   10
Leu Thr Phe Gly Lys Gly Thr Leu Leu Thr Val Asn
             15                  20
Pro Trp Ile Gln Asn Pro Asp
 25                  30
```

( 2 ) INFORMATION FOR SEQ ID NO:24:

( i ) SEQUENCE CHARACTERISTICS:
        ( A ) LENGTH: 33
        ( B ) TYPE: AMINO ACID
        ( C ) STRANDEDNESS: UNKNOWN
        ( D ) TOPOLOGY: UNKNOWN ( x i ) SEQUENCE DESCRIPTION:SEQ ID NO:24:

```
Val Tyr Phe Cys Ala Ala Tyr Tyr Gly Gly Ser Gln
 1               5                   10
Gly Trp Leu Ile Phe Gly Lys Gly Thr Lys Leu Ser
             15                  20
Val Lys Pro Asn Ile Gln Asn Pro Asp
 25                  30
```

( 2 ) INFORMATION FOR SEQ ID NO:25:

( i ) SEQUENCE CHARACTERISTICS:
        ( A ) LENGTH: 32
        ( B ) TYPE: AMINO ACID
        ( C ) STRANDEDNESS: UNKNOWN
        ( D ) TOPOLOGY: UNKNOWN ( x i ) SEQUENCE DESCRIPTION:SEQ ID NO:25:

```
Met Tyr Leu Cys Ala Ser Ser Phe Glu Gly Leu Gly
 1               5                   10
Thr Glu Ala Phe Phe Gly Gln Gly Thr Arg Leu Thr
             15                  20
```

Val Val Glu Asp Leu Asn Lys Val
25                  30

(2) INFORMATION FOR SEQ ID NO:26:

(i) SEQUENCE CHARACTERISTICS:
        (A) LENGTH: 33
        (B) TYPE: AMINO ACID
        (C) STRANDEDNESS: UNKNOWN
        (D) TOPOLOGY: UNKNOWN (xi) SEQUENCE DESCRIPTION:SEQ ID NO:26:

Leu Tyr Leu Cys Ala Ser Ser Gln Glu Gly Leu Ala
1               5                   10

Gly Ala Ser Gln Tyr Phe Gly Pro Gly Thr Arg Leu
        15              20

Thr Val Thr Glu Asp Leu Lys Trp Val
25                  30

(2) INFORMATION FOR SEQ ID NO:27:

(i) SEQUENCE CHARACTERISTICS:
        (A) LENGTH: 9
        (B) TYPE: AMINO ACID
        (C) STRANDEDNESS: UNKNOWN
        (D) TOPOLOGY: UNKNOWN (xi) SEQUENCE DESCRIPTION:SEQ ID NO:27:

Thr Thr Ala Glu Glu Ala Ala Gly Ile
1               5

(2) INFORMATION FOR SEQ ID NO:28:

(i) SEQUENCE CHARACTERISTICS:
        (A) LENGTH: 9
        (B) TYPE: AMINO ACID
        (C) STRANDEDNESS: UNKNOWN
        (D) TOPOLOGY: UNKNOWN (xi) SEQUENCE DESCRIPTION:SEQ ID NO:28:

Ala Ala Gly Ile Gly Ile Leu Thr Val
1               5

(2) INFORMATION FOR SEQ ID NO:29:

(i) SEQUENCE CHARACTERISTICS:
        (A) LENGTH: 10
        (B) TYPE: AMINO ACID
        (C) STRANDEDNESS: UNKNOWN
        (D) TOPOLOGY: UNKNOWN (xi) SEQUENCE DESCRIPTION:SEQ ID NO:29:

Glu Ala Ala Gly Ile Gly Ile Leu Thr Val
1               5                   10

(2) INFORMATION FOR SEQ ID NO:30:

(i) SEQUENCE CHARACTERISTICS:
        (A) LENGTH: 9
        (B) TYPE: AMINO ACID
        (C) STRANDEDNESS: UNKNOWN
        (D) TOPOLOGY: UNKNOWN (xi) SEQUENCE DESCRIPTION:SEQ ID NO:30:

Ile Leu Thr Val Ile Leu Gly Val Leu
1               5

( 2 ) INFORMATION FOR SEQ ID NO:31:

( i ) SEQUENCE CHARACTERISTICS:
        ( A ) LENGTH: 10
        ( B ) TYPE: AMINO ACID
        ( C ) STRANDEDNESS: UNKNOWN
        ( D ) TOPOLOGY: UNKNOWN ( x i ) SEQUENCE DESCRIPTION:SEQ ID NO:31:

```
Ala  Ala  Gly  Ile  Gly  Ile  Leu  Thr  Val  Ile
 1              5                        10
```

( 2 ) INFORMATION FOR SEQ ID NO:32:

( i ) SEQUENCE CHARACTERISTICS:
        ( A ) LENGTH: 10
        ( B ) TYPE: AMINO ACID
        ( C ) STRANDEDNESS: UNKNOWN
        ( D ) TOPOLOGY: UNKNOWN ( x i ) SEQUENCE DESCRIPTION:SEQ ID NO:32:

```
Leu  Leu  Asp  Gly  Thr  Ala  Thr  Leu  Arg  Leu
 1              5                        10
```

( 2 ) INFORMATION FOR SEQ ID NO:33:

( i ) SEQUENCE CHARACTERISTICS:
        ( A ) LENGTH: 9
        ( B ) TYPE: AMINO ACID
        ( C ) STRANDEDNESS: UNKNOWN
        ( D ) TOPOLOGY: UNKNOWN ( x i ) SEQUENCE DESCRIPTION:SEQ ID NO:33:

```
Tyr  Leu  Glu  Pro  Gly  Pro  Val  Thr  Ala
 1              5
```

( 2 ) INFORMATION FOR SEQ ID NO:34:

( i ) SEQUENCE CHARACTERISTICS:
        ( A ) LENGTH: 18
        ( B ) TYPE: NUCLEOTIDE
        ( C ) STRANDEDNESS: SINGLE
        ( D ) TOPOLOGY: UNKNOWN ( x i ) SEQUENCE DESCRIPTION:SEQ ID NO:34:

CCTCAGCTGG ACCACAGC                      18

( 2 ) INFORMATION FOR SEQ ID NO:35:

( i ) SEQUENCE CHARACTERISTICS:
        ( A ) LENGTH: 18
        ( B ) TYPE: NUCLEOTIDE
        ( C ) STRANDEDNESS: SINGLE
        ( D ) TOPOLOGY: UNKNOWN ( x i ) SEQUENCE DESCRIPTION:SEQ ID NO:35:

GGCAGACAGG ACCCCTTG                      18

( 2 ) INFORMATION FOR SEQ ID NO:36:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: UNKNOWN ( x i ) SEQUENCE DESCRIPTION:SEQ ID NO:36:

CTCGAGGTTC AGCCATGCTC CTGG                24

( 2 ) INFORMATION FOR SEQ ID NO:37:

( i ) SEQUENCE CHARACTERISTICS:
        ( A ) LENGTH: 20
        ( B ) TYPE: NUCLEOTIDE
        ( C ) STRANDEDNESS: SINGLE
        ( D ) TOPOLOGY: UNKNOWN ( x i ) SEQUENCE DESCRIPTION:SEQ ID NO:37:

GATGGCGGAG GCAGTCTCTG                                    20

( 2 ) INFORMATION FOR SEQ ID NO:38:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: UNKNOWN ( x i ) SEQUENCE DESCRIPTION:SEQ ID NO:38:

CTCGAGAGCA TGGGCTGCAG GCTG                               24

( 2 ) INFORMATION FOR SEQ ID NO:39:

( i ) SEQUENCE CHARACTERISTICS:
        ( A ) LENGTH: 32
        ( B ) TYPE: NUCLEOTIDE
        ( C ) STRANDEDNESS: SINGLE
        ( D ) TOPOLOGY: UNKNOWN ( x i ) SEQUENCE DESCRIPTION:SEQ ID NO:39:

AAAGGATCCG AGCTAGCCTC TGGAATCCTT TC                      32